US010844131B2

(12) United States Patent
Cohen et al.

(10) Patent No.: US 10,844,131 B2
(45) Date of Patent: Nov. 24, 2020

(54) ANTI-CD40 ANTIBODY

(71) Applicant: AbbVie Biotherapeutics Inc., Redwood City, CA (US)

(72) Inventors: Diane Sau Mun Cohen, San Jose, CA (US); Diane Hollenbaugh, Mountain View, CA (US); Shiming Ye, Palo Alto, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 16/559,504

(22) Filed: Sep. 3, 2019

(65) Prior Publication Data

US 2020/0010558 A1    Jan. 9, 2020

Related U.S. Application Data

(60) Division of application No. 16/036,691, filed on Jul. 16, 2018, now Pat. No. 10,400,041, and a division of application No. 15/606,227, filed on May 26, 2017, now Pat. No. 10,519,243, said application No. 16/036,691 is a division of application No. 15/901,560, filed on Feb. 21, 2018, now Pat. No. 10,023,645, which is a continuation of application No. 15/606,227, filed on May 26, 2017, now Pat. No. 10,519,243.

(60) Provisional application No. 62/342,417, filed on May 27, 2016.

(51) Int. Cl.
*A61K 39/395* (2006.01)
*C07K 16/28* (2006.01)
*A61K 39/00* (2006.01)

(52) U.S. Cl.
CPC ...... *C07K 16/2878* (2013.01); *C07K 16/2818* (2013.01); *A61K 2039/505* (2013.01); *A61K 2039/507* (2013.01); *A61K 2039/54* (2013.01); *C07K 2317/24* (2013.01); *C07K 2317/33* (2013.01); *C07K 2317/524* (2013.01); *C07K 2317/56* (2013.01); *C07K 2317/565* (2013.01); *C07K 2317/70* (2013.01); *C07K 2317/71* (2013.01); *C07K 2317/732* (2013.01); *C07K 2317/74* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 7,618,633 | B2  | 11/2009 | Bedian |            |
|-----------|-----|---------|--------|------------|
| 9,266,956 | B2  | 2/2016  | Zhang  |            |
| 10,023,645| B1* | 7/2018  | Cohen  | C07K 16/2878 |
| 10,400,041| B2* | 9/2019  | Cohen  | C07K 16/2818 |
| 10,519,243| B2* | 12/2019 | Cohen  | C07K 16/2878 |
| 2009/0074711 | A1 | 3/2009 | Glennie |          |
| 2009/0311268 | A1 | 12/2009 | Thomas |           |
| 2014/0120103 | A1 | 5/2014 | Zhang   |           |
| 2014/0377253 | A1 | 12/2014 | Harding |          |

FOREIGN PATENT DOCUMENTS

| EP | 1707627 A1 | 10/2006 |
| EP | 2889377 A1 | 7/2015 |
| WO | 2005123780 A2 | 12/2005 |
| WO | 2014144960 A2 | 9/2014 |
| WO | 2015091853 A2 | 6/2015 |
| WO | 2016069919 A1 | 10/2015 |

OTHER PUBLICATIONS

Lewis et al., 2011 "Proapoptotic signaling activity of the anti-CD40 monoclonal antibody dacetuzumab circumvents multiple oncogenic transformation events and chemosensitizes NHL cells," Leukemia 25:1007-16.
Alderson et al., 1993 "CD40 expression by human monocytes: regulation by cytokines and activation of monocytes by the ligand for CD40," J Exp Med 178(2):669-674.
Armitage et al., 1993 "CD40 ligand is a T cell growth factor," Eur J Immunol 23(9):2326-2331.
Banchereau et al., 1995 "Functional CD40 antigen on B cells, dendritic cells and fibroblasts," Adv Exp Med Biol 378:79-83.
Banchereau et al., 1998 "Dendritic cells and the control of immunity," Nature 392(6673):245-252.
Bishop, 2012 "The Power of Monoclonal Antibodies as Agents of Discovery: CD40 Revealed as a B Lymphocyte Costimulator," J Immunol 188:4127-4129.
Bensinger et al., 2012 "A phase 1 study of lucatumumab, a fully human anti-CD40 antagonist monoclonal antibody administered intravenously to patients with relapsed or refractory multiple myeloma," Br J Haematol 159:58-66.
Bourgeois et al., 2002 "A role for CD40 expression on CD8+ T cells in the generation of CD8+ T cell memory," Science 297:2060-2063.
Burington et al., "CD40 Pathway Activation Status Predicts Response to CD40 Therapy in Diffuse Large B Cell Lymphoma," Sci Transl Med 3(74):1-12 (pp. 1-14).
Ellmark et al., 2016 "Selective FcγR engagement by human agonistic anti-CD40 antibodies," Transl Cancer Res 5 (Suppl 4):S839-S841.
French et al., 1999 "CD40 antibody evokes a cytotoxic T-cell response that eradicates lymphoma and bypasses T-cell help," Nat Med 5(5):548-553.
Gladue et al., 2011 "The CD40 agonist antibody CP-870,893 enhances dendritic cell and B-cell activity and promotes anti-tumor efficacy in SCID-hu mice," Cancer Immunol Immunother 60(7):1009-1017.
Hollenbaugh et al., 1995 "Expression of Functional CD40 by Vascular Endothelial Cells," J Exp Med 182(1):33-40.

(Continued)

*Primary Examiner* — Phillip Gambel
(74) *Attorney, Agent, or Firm* — Dechert LLP

(57) ABSTRACT

The present disclosure provides novel anti-CD40 antibodies, compositions including the new antibodies, nucleic acids encoding the antibodies, and methods of making and using the same.

9 Claims, 20 Drawing Sheets

Specification includes a Sequence Listing.

(56) References Cited

OTHER PUBLICATIONS

Johnson et al., 2005 "Clinical and Biological Effects of an Agonist Anti-CD40 Antibody: A Cancer Research UK Phase I Study," Clin Cancer Res 21(6):1321-1328.
Law et al., 2005 "Preclinical Antilymphoma Activity of a Humanized Anti-CD40 Monoclonal Antibody, SGN-40," Cancer Res 65(18):8331-8338.
Ledbetter et al., 1987 "Augmentation of normal and malignant B cell proliferation by monoclonal antibody to the B cell-specific antigen BP50 (CDW40)," J Immunol 138(3):788-794.
Li et al., 2011 "Inhibitory Fcγ receptor engagement drives adjuvant and anti-tumor activities of agonistic CD40 antibodies," Science 333(6045):1030-1034.
Mackay et al., 1997 "Protective immunity induced by tumor vaccines requires interaction between CD40 and its ligand, CD154," Cancer Res 57(13):2569-2574.
Maldonado et al., 2010 "How tolerogenic dendritic cells induce regulatory T cells," Adv Immunol 108:111-165.
Mangsbo et al., 2015 "The Human Agonistic CD40 Antibody ADC-1013 Eradicates Bladder Tumors and Generates T-cell-Dependent Tumor Immunity," Clin Cancer Res 21(5):1115-1126.
Miller et al., 2015 "The Journey from Discoveries in Fundamental Immunology to Cancer Immunotherapy," Cancer Cell 27(4):439-449.
Moran et al., 2013 "The TNFRs OX40, 4-1BB, and CD40 as targets for cancer immunotherapy," Curr Opin Immunol 25(2):1-12.
Paulie et al., 1985 "A p50 surface antigen restricted to human urinary bladder carcinomas and B lymphocytes," Cancer Immunol Immunother 20(1):23-28.
Shalapour et al., 2015 "Immunity, inflammation, and cancer: an eternal fight between good and evil," J Clin Invest 125(9):3347-3355.
Shen et al., 2014 "IL-35-producing B cells are critical regulators of immunity during autoimmune and infectious diseases," Nature 507(7492):366-370 (23 pages).
Sotomayor et al., 1999 "Conversion of tumor-specific CD4+ T cell tolerance to T-cell priming through in vivo ligation of CD40," Nat Med 5(7):780-787.
Stamenkovic et al., 1989 "A B-lymphocyte activation molecule related to the nerve growth factor receptor and induced by cytokines in carcinomas," EMBO J 8(5):1403 1410.
Van Mierlo et al., 2002 "CD40 stimulation leads to effective therapy of CD40(−) tumors through induction of strong systemic cytotoxic T lymphocyte immunity," Proc Natl Acad Sci USA 99(8):5561-5566.
Vonderheide et al., 2013 "Agonistic CD40 Antibodies and Cancer Therapy," Clin Cancer Res 19(5):1035-1043.
White et al., 2011 "Interaction with FcγRIIB Is Critical for the Agonistic Activity of Anti-CD40 Monoclonal Antibody," J Immunol 187:1754-1763.

* cited by examiner

CD40 Receptor (SEQ ID NO:40) (from EMBO J, 8(5), 1403-1410 (1989))

```
           10         20         30         40         50
    MVRLPLQCVL WGCLLTAVHP EPPTACREKQ YLINSQCCSL CQPGQKLVSD
           60         70         80         90        100
    CTEFTETECL PCGESEFLDT WNRETHCQH  KYCDPNLGLR VQQKGTSETD
          110        120        130        140        150
    TICTCEEGWH CTSEACESCV LHRSCSPGFG VKQIATGVSD TICEPCPVGF
          160        170        180        190        200
    FSNVSSAFEK CHPWTSCETK DLVVQQAGTN KTDVVCGPQD RLRALVVIPI
          210        220        230        240        250
    IFGILFAILL VLVFIKKVAK KPTNKAPHPK QEPQEINFPD DLPGSNTAAP
          260        270
    VQETLHGCQP VTQEDGKESR ISVQERQ
```

CD40 Ligand (SEQ ID NO:41) (from FEBS Letters, 315 (3), 259-266 (1993))

```
           10         20         30         40         50
    MIETYNQTSP RSAATGLPIS MKIFMYLLTV FLITQMIGSA LFAVYLHRRL
           60         70         80         90        100
    DKIEDERNLH EDFVFMKTIQ RCNTGERSLS LLNCEEIKSQ FEGFVKDIML
          110        120        130        140        150
    NKEETKKENS FEMQKGDQNP QIAAHVISEA SSKTTSVLQW AEKGYYTMSN
          160        170        180        190        200
    NLVTLENGKQ LTVKRQGLYY IYAQVTFCSN REASSQAPFI ASLCLKSPGR
          210        220        230        240        250
    FERILLRAAN THSSAKPCGQ QSIHLGGVFE LQPGASVFVN VTDPSQVSHG
          260
    TGFTSFGLLK L
```

FIG. 1

Mouse anti-human CD40 Antibody Domains
Variable domains (CDRs in bold)

muAb1 V$_H$ (SEQ ID NO: 101)
QVQLQQPGAELVKPGASVKMSCKASGYTFTSYWITWVKQRPGQGLEWIG**EINPGSGS
TNYNEKFKSKATLTVDTSSSTAYMQLSSLTSEDSAVYYCARNRGTGDY**WGQGTTLTVSS muAb1 V$_L$ (SEQ ID NO: 151)
DVVMTQTPLSLPVSLGDQASISCRSSQSLVHSYGNTYLHWYLQKPGQSPKFLIY**KVSNR
ISGVPDRLSGSGSGTDFTLKISRVEPEDLGVYFCSQSTHVPYT**FGGGTKLEIK muAb2 V$_H$ (SEQ ID NO: 102)
QVQLQQSGAELMKPGASAKLSCKATGYTFTGYWIQWVKQRPGHGLEWIG**EILPGGD
HTKYNEKFRGKATFTSDTSSNTVYMQLSSLTTEDSAIYYCARVGGDY**WGQGTTLVSS muAb2 V$_L$ (SEQ ID NO: 152)
DVVMTQTPLSLPVSLGDQASISCRSSQSLVNSNENTYLHWYLQKPGQSPKLLIY**KVFNR
YSGVPDRFSGSGSGTDFTLKISRVEAEDLGVYFCFQSTHVPWT**FGGGTKLEIK muAb3 V$_H$ (SEQ ID NO: 103)
EVQLQQSGPELVKPGASVKISCKASGYTFTDYYMNWVKQSHGKSLEWIG**DINPNNGG
TSYNQKFKGKATLTVDKSSSTAYMELRSLTSEDSAVYYCARRGGLGRGTYALDY**WGQGTSVTVSS muAb3 V$_L$ (SEQ ID NO: 153)
DIQMTQTTSSLSASLGDRVTISCRASQDISNYLNWYQQKPDGTVKPLIY**YTSRLHLGVP
SRFSGSGSGTDYSLTISNLEQEDIATYFCQQGNTLPLT**FGAGTKLELK

*FIG. 2A*

Mouse anti-human CD40 Antibody Domains
Variable domains (CDRs in bold)

muAb4 V$_H$ (SEQ ID NO: 104)
LVQPGGSLSLSCAASGFTFSDYYMSWVRQPPGKALEWLGFIRNKANGYTTEFSASVKGRFTISRDNSQSILYLQMNALRAEDSATYYCARYGGLRQGWYFDVWGTGTTVTSS muAb4 V$_L$ (SEQ ID NO: 154)
DIQMTQTTSSLSASLGDRVTISCRASQDIRNYLNWYQQKPDGTVKLLIYYTSRLHSGVPSRFSGSGSGTDYSLTISNLEQEDIATYFCQQGKTLPWTFGGGSKLEMK muAb5 V$_H$ (SEQ ID NO: 105)
DVQLQESGPGLVEPSQSLFLTCSVTGYSITTNYNWNWIRQFPGNKLEWMGYIRHDGTN NYNPSLKNRISIIRDTPKNQFFLKLNSVTTEDTAIYFCTRLDYDYWGQGTSVTVSS muAb5 V$_L$ (SEQ ID NO: 155)
DAVMTQTPLSLPVSLGDQASISCRSSQSLENSYGNTFLNWFLQRPGQSPQLLIYRVSNR FCGVPDRFSGSGSGTDFTLKISRVEAEDLGIYFCLQVTHVPYTFGGGTKLEIK muAb6 V$_H$ (SEQ ID NO: 106)
QVQLQQPGAELVRPGSSVKLSCKASGYTFTSYWMHWVKQRPIQGLEWIGNIDPSNGE THYNQKFKDKATLTVDKSSSTAYMQLSSLTSEDSAVYYCARERIYYSGSTYDGYFDVWGTGTTVTVSS muAb6 V$_L$ (SEQ ID NO: 156)
QIVLTQSPAIMSASPGEKVTMTCSASSSLSYMHWYQQKSGTSPKRWIYDTSKLASGVPA RFSGSGSGTSYSLTISSMEAEDAATYYCQQWSSNPWTFGGGTKLEIK muAb7 V$_L$ (SEQ ID NO: 157)
QIVLTQSPAIMSASPGEKVTMTCSASSSLSYMHWYQQKSGTSPKRWIYDTSKLASGVPA RFSGSGSGTSYSLTISSMEGEDGATYYCQQWSSNPWTFGGGTKLEIK

*FIG. 2B*

Mouse anti-human CD40 Antibody Domains
Variable domains (CDRs in bold)

muAb8 V$_H$ (SEQ ID NO: 107)
QVQLQQSGPELVKSGASVKISCKASGYTFTDYYINWVKQRPGQGLEWIGWIFPGSGSV YCNEQFKGQATLTVDRSSSTAYMLLSSLTSEDSAVYFCASSLGKFAYWGQGTLVTVSA muAb8 V$_L$ (SEQ ID NO: 158)
DIVMTQSQKFMSTTVGDRVSITCKASQSVVTAVAWYQQKPGQSPKLLIYSASNRYTGV PDRFTGSGSGTDFALTIRTMQSEDLADYFCQQYSSYPYTFGGGTKLEIK muAb9 V$_H$ (SEQ ID NO: 108)
DVQLQESGPGLVKPSQSLSLTCSVTGYSITSNYYWMNWIRQFPGNKLEWMGYIRYDGSN NYNPSLKNRISITRDTSKNQFFLKLNSVTTEDTATYYCARLDYWGQGTTLTVSS muAb9 V$_L$ (SEQ ID NO: 159)
DAVMTQTPLSLPVSLGDQASISCRSSQSLENTNGNTFLNWFLQKPGQSPQLLIYRVSNR FSGVPDRFSGSGSGTDFTLKISRVEAEDLGVYFCLQVTHVPFTFGSGTKLEIK muAb10 V$_H$ (SEQ ID NO: 109)
DVQLQESGPGLVKPSQSLSLTCSVTGYSITSNYYWMNWIRQFPGNKLEWMGYIRYDGSN NYNPSLKNRISITRDTSKNQFFLRLNSVTTEDTATYYCTRLDYWGQGTTLTVSS muAb10 V$_L$ (SEQ ID NO: 160)
DAVMTQTPLSLPVSLGDQASISCRSSQSLENSNGNTFLNWFLQKPGQSPQLLIYRISNRF SGVPDRFSGSGSGTDFTLKISRVEAEDLGVYFCLQVTHVPFTFGSGTKLEIK

*FIG. 2C*

Humanized anti-human CD40 Antibody Domains
Variable domains (CDRs in bold)

huAb6-1 V$_H$ (SEQ ID NO: 110)
EVQLVQSGAEVKKPGSSVKVSCKASGYTFTSYWMHWVRQAPGQGLEWIGNIDPSNGETHYNQ
KFKDRATLTVDKSTSTAYMELSSLRSEDTAVYYCARERIYYSGSTYDGYFDVWGQGTTVTVSS huAb6-1 V$_L$ (SEQ ID NO: 161)
DIQLTQSPSFLSASVGDRVTITCSASSSLSYMHWYQQKPGKSPKRWIYDTSKLASGVPSRFSGSGS
GTEYTLTISSLQPEDFATYYCQQWSSNPWTFGGGTKVEIK huAb6-2 V$_H$ (SEQ ID NO: 111)
EVQLVQSGAEVKKPGSSVKVSCKASGYTFTSYWMHWVRQAPGQGLEWIGNIDPSNGETHYNQ
KFKDRVTITVDKSTSTAYMELSSLRSEDTAVYYCARERIYYSGSTYDGYFDVWGQGTTVTVSS huAb6-3 V$_H$ (SEQ ID NO: 112)
EVQLVQSGAEVKKPGSSVKVSCKASGYTFTSYWMHWVRQAPGQGLEWIGNIDPSNGETHYAQ
KFQGRVTITVDKSTSTAYMELSSLRSEDTAVYYCARERIYYSGSTYDGYFDVWGQGTTVTVSS huAb8-1 V$_H$ (SEQ ID NO: 113)
EVQLVQSGAEVKKPGSSVKVSCKASGYTFTDYYINWVRQAPGQGLEWIGWIFPGSGSVYCNEQF
KGRATLTVDRSTSTAYMELSSLRSEDTAVYFCASSLGKFAYWGQGTLVTVSS huAb8-1 V$_L$ (SEQ ID NO: 162)
DIQMTQSPSSLSASVGDRVTITCKASQSVVTAVAWYQQKPGKSPKLLIYSASNRYTGVPSRFSGSGS
GTDFTLTISSLQPEDFATYFCQQYSSYPYTFGGGTKVEIK huAb8-2 V$_H$ (SEQ ID NO: 114)
EVQLVQSGAEVKKPGSSVKVSCKASGYTFTDYYINWVRQAPGQGLEWIGWIFPGSGSVYSNEQF
KGRATLTVDRSTSTAYMELSSLRSEDTAVYFCASSLGKFAYWGQGTLVTVSS

*FIG. 2D*

Humanized anti-human CD40 Antibody Domains
Variable domains (CDRs in bold)

huAb8-3 V$_H$ (SEQ ID NO: 115)
EVQLVQSGAEVKKPGSSVKVSCKASGYTFTDYYINWVRQAPGQGLEWIGWIFPGSGSVYCNEQF
KGRVTITVDKSTSTAYMELSSLRSEDTAVYYCASSLGKFAYWGQGTLVTVSS huAb9-1 V$_H$ (SEQ ID NO: 116)
EVQLQESGPGLVKPSETLSLTCTVSGYSITSNYYWNWIRQPPGKGLEWMGYIRYDGSNNYNPSL
KNRITISRDTSKNQFSLKLSSVTAADTAVYYCARLDYWGQGTTVTVSS huAb9-1 V$_L$ (SEQ ID NO: 163)
DAVMTQTPLSLSVTPGQPASISCRSSQSLENTGNTFLNWFLQKPGQSPQLLIYRVSNRFSGVPD
RFSGSGSGTDFTLKISRVEAEDVGVYFCLQVTHVPFTFGQGTKLEIK huAb9-2 V$_H$ (SEQ ID NO: 117)
EVQLQESGPGLVKPSETLSLTCTVSGYSITSNYYWNWIRQPPGKGLEWMGYIRYDGSNNYNPSL
KNRVTISRDTSKNQFSLKLSSVTAADTAVYYCARLDYWGQGTTVTVSS huAb9-3 V$_H$ (SEQ ID NO: 118)
EVQLQESGPGLVKPSETLSLTCTVSGYSISSNYYWNWIRQPPGKGLEWMGYIRYDGSNNYNPSL
KSRVTISRDTSKNQFSLKLSSVTAADTAVYYCARLDYWGQGTTVTVSS huAb9-4 V$_L$ (SEQ ID NO: 164)
DAVMTQTPLSLSVTPGQPASISCRSSQSLENTGNTFLNWYLQKPGQSPQLLIYRVSNRFSGVPD
RFSGSGSGTDFTLKISRVEAEDVGVYYCLQVTHVPFTFGQGTKLEIK

FIG. 2E

Humanized anti-human CD40 Antibody Domains
Variable domains (CDRs in bold)

huAb9-7 V$_H$ (SEQ ID NO: 119)

EVQLVESGGGLVKPGETLSLTCTVSGYSITSNYYYWNWIRQPPGKGLEWMG**YIRYDGSNNYNPSL
KGRVTISRDTSKNQFYLKLSSVTAADTAVYYCARLDY**WGQGTTVTVSS huAb9-8 V$_H$ (SEQ ID NO: 120)

EVQLVESGGGLVQPGGSLRLSCAASGYSITSNYYYWNWIRQPPGKGLEWMG**YIRYDGSNNYNPS
LKGRVTISRDTSKNQLYLKLSSVTAADTAVYYCARLDY**WGQGTLVTVSS huAb9-9 V$_H$ (SEQ ID NO: 121)

EVQLVESGGGLVKPGETLILTCTVSGYDITSNYYYWNWIRQPPGKGLEWMG**YIRYDGSNNYNPSL
KGRVTISRDTSKNQFYLKLSSVTAADTAVYYCARLDY**WGQGTLVTVSS huAb9 rehu VH4 V$_H$ (SEQ ID NO: 122)

QVQLQESGPGLVKPSETLSLTCTVSGYSITSNYYYWNWIRQPPGKGLEWMG**YIRYDGSNNYNPSL
KNRITISRDTSKNQFSLKLSSVTAADTAVYYCARLDY**WGQGTLVTVSS huAb9 rehu VH3 V$_H$ (SEQ ID NO:123)

EVQLVESGGGLVQPGGSLRLSCAASGYSITSNYYYWNWVRQAPGKGLEWMG**YIRYDGSNNYNPS
LKNRITISRDTSKNTFYLQMNSLRAEDTAVYYCARLDY**WGQGTLVTVSS

*FIG. 2F*

Humanized anti-human CD40 Antibody Domains
Variable domains (CDRs in bold)

huAb9-7 V$_L$ (SEQ ID NO: 165)
DAVMTQTPLSLSVTEGQPASISCRSSQSLENTNGNTFLNWYLQKPGQSPQLLIY**RVSNRFSGVPD
RFSGSGSGTDFTLKISRVEAEDVGVYYCLQVTHVPFTFGQGTKLEIK huAb9-9 V$_L$ (SEQ ID NO: 166)
DAVMTQTPLSLAVLPGQPASISCRSSQSLENTNGNTFLNWYLQKPGQSPQLLIY**RVSNRFSGVPD
RFSGSGSGTDFTLKISRVEAEDVGVYYCLQVTHVPFTFGQGTKLEIK huAb9 VK1 V$_L$ (SEQ ID NO: 167)
DIQMTQSPSSLSASVGDRVTITCRSSQSLENTNGNTFLNWYQQKPGKAPKLLIY**RVSNRFSGVPS
RFSGSGSGTDFTLTISSLQPEDFATYYCLQVTHVPFTFGQGTKVEIK huAb9 rehu VK2 V$_L$ (SEQ ID NO: 168)
DAVMTQSPLSLPVTLGEPASISCRSSQSLENTNGNTFLNWFQQKPGQSPRLLIY**RVSNRFSGVPD
RFSGSGSGTDFTLKISRVEAEDVGVYYCLQVTHVPFTFGQGTKLEIK huAb9 rehu VK1 V$_L$ (SEQ ID NO: 169)
DAQMTQSPSSLSASVGDRVTITCRSSQSLENTNGNTFLNWFQQKPGKAPKLLIY**RVSNRFSGVPS
RFSGSGSGTDFTLTISSLQPEDFATYYCLQVTHVPFTFGQGTKLEIK huAb9 A2I V$_L$ (SEQ ID NO: 170)
DIVMTQTPLSLSVTPGQPASISCRSSQSLENTNGNTFLNWYLQKPGQSPQLLIY**RVSNRFSGVPDR
FSGSGSGTDFTLKISRVEAEDVGVYYCLQVTHVPFTFGQGTKLEIK huAb9 A2V V$_L$ (SEQ ID NO: 171)
DVVMTQTPLSLSVTPGQPASISCRSSQSLENTNGNTFLNWYLQKPGQSPQLLIY**RVSNRFSGVPD
RFSGSGSGTDFTLKISRVEAEDVGVYYCLQVTHVPFTFGQGTKLEIK

*FIG. 2G*

ANTI-CD40 ANTIBODY

CROSS REFERENCE TO RELATED APPLICATIONS

This application is a divisional of U.S. application Ser. No. 16/036,691, filed Jul. 16, 2018, now U.S. Pat. No. 10,400,041, issued Sep. 3, 2019, which is a divisional of U.S. application Ser. No. 15/901,560, filed Feb. 21, 2018, now U.S. Pat. No. 10,023,645, issued Jul. 17, 2018, which is a continuation of U.S. application Ser. No. 15/606,227, filed May 26, 2017, now U.S. Pat. No. 10,519,243, issued Dec. 31, 2019, which claims the benefit under 35 U.S.C. § 119(e) of U.S. Provisional Application No. 62/342,417, filed May 27, 2016, the contents of all of which are incorporated herein in their entireties by reference thereto. This application is a divisional of U.S. application Ser. No. 15/606,227, filed May 26, 2017, now U.S. Pat. No. 10,519,243, issued Dec. 31, 2019, which claims the benefit under 35 U.S.C. § 119(e) of U.S. Provisional Application No. 62/342,417, filed May 27, 2016, the contents of all of which are incorporated herein in their entireties by reference thereto.

SEQUENCE LISTING

The instant application contains a Sequence Listing which has been submitted electronically in ASCII format and is hereby incorporated by reference in its entirety. Said ASCII copy, created on Sep. 3, 2019, is named 285C1D1D1 Sequence Listing.txt and is 106,228 bytes in size.

3. TECHNICAL FIELD

The present application pertains to, among other things, novel anti-CD40 antibodies, compositions including the new antibodies, nucleic acids encoding the antibodies, and methods of making and using the same.

4. BACKGROUND

Cancer therapies comprise a wide range of therapeutic approaches, including surgery, radiation, and chemotherapy. While the various approaches allow a broad selection of treatments to be available to the medical practitioner to treat the cancer, existing therapeutics suffer from a number of disadvantages, such as a lack of selectivity of targeting cancer cells over normal, healthy cells, and the development of resistance by the cancer to the treatment.

Recent approaches based on targeted therapeutics, which interfere with cellular processes of cancer cells preferentially over normal cells, have led to chemotherapeutic regimens with fewer side effects as compared to non-targeted therapies such as radiation treatment.

Cancer immunotherapy, in particular the development of agents that activate T cells of the host's immune system to prevent the proliferation of or kill cancer cells, has emerged as a promising therapeutic approach to complement existing standards of care. See, e.g., Miller, et al. Cancer Cell, 27, 439-449 (2015). Such immunotherapy approaches include the development of antibodies used to modulate the immune system to kill cancer cells. For example, anti-PD-1 blocking antibodies pembrolizumab (Keytruda®) and nivolumab (Opdivo®) have been approved in the US and the European Union to treat diseases such as unresectable or metastatic melanoma and metastatic non-small cell lung cancer. Efforts to inhibit immunosuppressive proteins such as CTLA-4 have led to the development and clinical evaluation of anti-CTLA-4 antibodies, such as tremelimumab and ipilimumab (Yervoy®).

There remains a need for alternative approaches and additional cancer treatments to complement existing therapeutic standards of care.

5. SUMMARY

Human CD40 (SEQ ID NO:40) is a tumor necrosis factor (TNF) receptor superfamily member (TNF superfamily member 5) expressed on antigen-presenting cells such as B cells, dendritic cells (DC), and monocytes, and nonimmune cells, including certain types of tumor cells. When activated by human CD40 ligand (SEQ ID NO:41), human CD40 activates antigen-presenting cells and induces responses from both innate and adaptive immune systems. Agonistic CD40 agents can be used to induce the immune system to prevent proliferation of and/or kill tumor cells, and thus provide effective therapeutic treatment of solid tumors.

The present disclosure provides anti-CD40 antibodies and binding fragments thereof that specifically bind to human CD40 (SEQ ID NO:40). The amino acid sequences of exemplary CDRs, as well as the amino acid sequence of the $V_H$ and $V_L$ regions of the heavy and light chains of exemplary anti-CD40 antibodies are provided in the Detailed Description below.

The $V_H$ and $V_L$ chains of the anti-CD40 antibodies described herein afford an allosteric agonistic receptor response that can activate human CD40 in the presence or absence of CD40 ligand (CD40L), without competing with the CD40L-CD40 binding interaction. Moreover, the present anti-CD40 antibodies, by interacting with CD40, can enhance CD40L binding to CD40.

The anti-CD40 antibodies may include modifications and/or mutations that alter the properties of the antibodies, such as increase half-life, increase or decrease ADCC, or increase agonistic activity, as is known in the art.

Nucleic acids comprising nucleotide sequences encoding the anti-CD40 antibodies of the disclosure are provided herein, as are vectors comprising nucleic acids. Additionally, prokaryotic and eukaryotic host cells transformed with a vector comprising a nucleotide sequence encoding a disclosed anti-CD40 antibody are provided herein, as well as eukaryotic (such as mammalian) host cells engineered to express the nucleotide sequences. Methods of producing antibodies, by culturing host cells and recovering the antibodies are also provided, and discussed further in the Detailed Description below.

In another aspect, the present disclosure provides compositions including the anti-CD40 antibodies described herein. The compositions generally comprise one or more anti-CD40 antibody as described herein, and/or salts thereof, and one or more excipients, carriers or diluents.

The present disclosure provides methods of treating subjects, such as human subjects, diagnosed with a solid tumor with an anti-CD40 antibody. The method generally involves administering to the subject an amount of an anti-CD40 antibody described herein effective to provide therapeutic benefit. The subject may be diagnosed with any one of a number of solid tumors that may be newly diagnosed, relapsed, or relapsed and refractory. An anti-CD40 antibody is typically administered as an intravenous infusion or intratumoral injection at doses ranging from about 0.001 mg/kg to about 4 mg/kg. An anti-CD40 antibody is typically administered as an intravenous infusion or intratumoral injection twice a week, once a week, once every two weeks, once every three weeks, once every four weeks, once every five weeks, once every six weeks, once every seven weeks, or once every eight weeks.

The anti-CD40 antibodies may be administered as single therapeutic agents (monotherapy) or adjunctive to or with other therapeutic agents typically, but not necessarily, those used for the treatment of a solid tumor. Therapeutic agents typically will be used at their approved dose, route of administration, and frequency of administration, but may be used at lower dosages.

The anti-CD40 antibodies may be administered via a variety of routes or modes of administration, including but not limited to, intravenous infusion and/or injection, subcutaneous injection, and intratumoral injection. The amount administered will depend upon the route of administration, the dosing schedule, the type of cancer being treated, the stage of the cancer being treated, and other parameters such as the age and weight of the patient, as is well known in the art. Specific exemplary dosing schedules expected to provide therapeutic benefit are provided in the detailed description.

Based on data presented herein, it is expected that the anti-CD40 antibodies described herein will provide therapeutic benefit to subjects diagnosed with a solid tumor.

6. BRIEF DESCRIPTION OF THE FIGURES

FIG. 1 shows the amino acid sequences of human CD40 receptor (SEQ ID NO:40) and human CD40 ligand (SEQ ID NO:41).

FIGS. 2A-2G provide amino acid sequences for $V_H$ and $V_L$ of exemplary mouse and humanized anti-CD40 antibodies. FIG. 2A shows the $V_H$ and $V_L$ amino acid sequences for muAb1 through muAb3; FIG. 2B shows the $V_H$ and $V_L$ amino acid sequences for muAb4 through muAb7; FIG. 2C shows the $V_H$ and $V_L$ amino acid sequences for muAb8 through muAb10; FIG. 2D shows the $V_H$ and $V_L$ amino acid sequences for humanized antibodies of muAb6 and muAb8; FIG. 2E shows the $V_H$ and $V_L$ amino acid sequences for humanized antibodies of muAb8 and muAb9; FIG. 2F shows the $V_H$ and $V_L$ amino acid sequences for further humanized antibodies of muAb9; and FIG. 2G shows the $V_H$ and $V_L$ amino acid sequences for additional humanized antibodies of muAb9.

FIG. 3 provides the results of competition experiments on human CD40 between CD40L and exemplary anti-CD40 antibodies. Upper left shows exemplary anti-CD40 antibodies that compete with CD40L; upper right shows antibodies that do not significantly compete with CD40L; lower left shows antibodies that enhance CD40-CD40L interaction; lower right shows effects of anti-CD40 antibody huAb9 A2I and CP-870,893. Y-axis depicts optical density (OD) at 650 nm; x-axis depicts antibody dose ("Sample") in µg/mL.

FIG. 4 shows the binding of fluorochrome-conjugated human CD40 at a fixed concentration of 1 µg/mL on Jurkat cells expressing human CD40L in the presence of increasing amounts of antibody huAb9 A2I, CP-870,893, human IgG$_1$ ("huIgG1") isotype or human IgG$_2$ ("huIgG2") isotype. Y-axis depicts mean fluorescence intensity ("MFI") representing the binding; x-axis depicts antibody dose ("Sample") in µg/mL.

FIGS. 5A-5B show the effects of an antibody dose ("Sample") at 3 µg/mL or media only on NFκB signal from HEK293 blue CD40 NFκB reporter cells mixed with Jurkat D1.1 cells (1:1 ratio). Antibody huAb9 A2I, CP-870,893, human IgG$_1$ ("huIgG1") isotype or human IgG$_2$ ("huIgG2") isotype, or media only, was added to the individual sample.

FIG. 5A depicts the NFκB signal in cultures containing CD40L negative ("CD40L-") Jurkat D1.1 cells. FIG. 5B depicts the NFκB signal in cultures containing CD40L positive ("CD40L+") Jurkat D1.1 cells. Y-axis depicts OD at 625 nm; x-axis depicts antibody or media only treatment ("Sample").

FIGS. 6A-6B show the binding of antibody doses ("Sample") in µg/mL of huAb9-5 with wild type huIgG$_1$, or with V273Y or V273E variant, or CP-870,893, in CHO cells expressing CD16F, CD16V, CD32a, CD32b, or CD64. FIG. 6A shows binding of an anti-CD40 antibody on CHO cells expressing CD16F (upper left), CD16V (upper right), CD32a (lower left), or CD32b (lower right). FIG. 6B shows binding of an anti-CD40 antibody on CHO cells expressing CD64. Y-axis depicts mean fluorescence intensity (MFI) representing the binding; x-axis depicts antibody dose ("Sample") in µg/mL.

FIG. 7 shows the antibody-dependent cell-mediated cytotoxicity (ADCC) of constant region variants V273E or V273Y for antibody huAb9-5 as compared with huAb9-5 with the wild type human IgG$_1$ in RL cells. Y-axis depicts percent cytotoxicity in RL cells; x-axis depicts antibody dose ("Sample") in µg/mL.

FIG. 8 shows the effect of antibody huAb6-1 (upper left), huAb9-5 (lower left), huAb8-1 (upper right) with wild type human IgG$_1$, or a constant region variant V273E or V273Y, on B cell proliferation. Lower right graph shows B cell proliferation effects of huAb9 A2I with human IgG$_1$ V273E variant or CP-870,893. Y-axis depicts B cell proliferation in counts per minute (CPM); x-axis depicts antibody dose ("Sample") in µg/mL.

FIG. 9 shows the effect of antibody huAb6-1 (upper left), huAb9-5 (lower left) and huAb8-1 (upper right) with wild type human IgG$_1$, or a constant region variant V273E or V273Y, on dendritic cell (DC) activation as measured by IL-12p70 production in pg/mL. Lower right graph shows DC activation of huAb9 A2I with human IgG$_1$ V273E variant or CP-870,893. Y-axis depicts IL-12p70 in pg/mL; x-axis depicts antibody dose ("Sample") in µg/mL.

7. DETAILED DESCRIPTION

Figure 3:
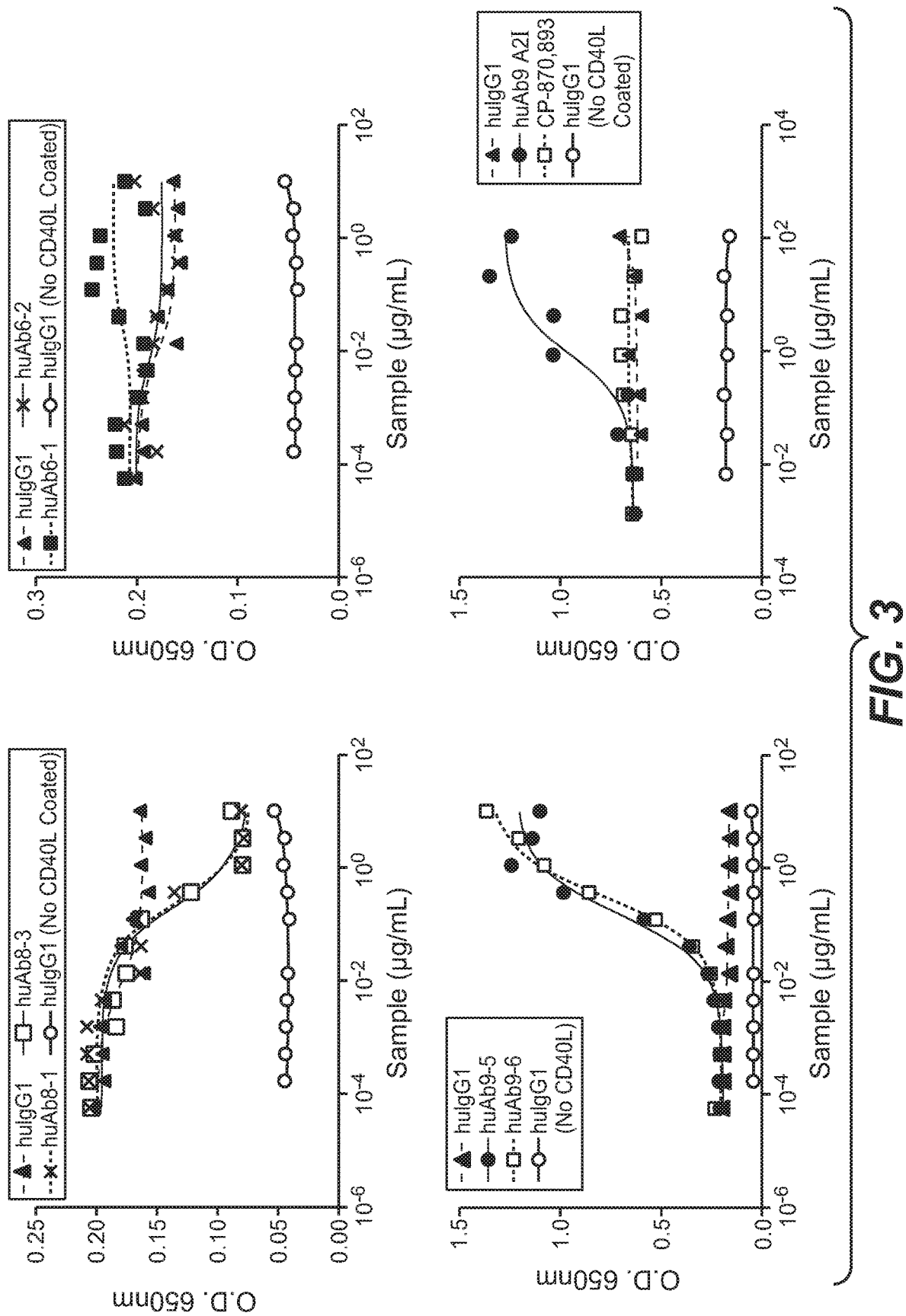

The present disclosure concerns antibodies and fragments that specifically bind human CD40 (SEQ ID NO:40), compositions comprising the antibodies, polynucleotides encoding anti-CD40 antibodies, host cells capable of producing the antibodies, methods and compositions useful for making the antibodies and binding fragments, and various methods of using the same.

As will be appreciated by skilled artisans, antibodies are "modular" in nature. Throughout the disclosure, various specific embodiments of the various "modules" composing the antibodies are described. As specific non-limiting examples, various specific embodiments of $V_H$ CDRs, $V_H$ chains, $V_L$ CDRs and $V_L$ chains are described. It is intended that all of the specific embodiments may be combined with each other as though each specific combination were explicitly described individually.

7.1. Abbreviations

The antibodies, binding fragments, ADCs and polynucleotides described herein are, in many embodiments, described by way of their respective polypeptide or polynucleotide sequences. Unless indicated otherwise, polypeptide sequences are provided in N→C orientation; polynucleotide sequences in 5'→3' orientation. For polypeptide sequences, the conventional three or one-letter abbreviations for the genetically encoded amino acids may be used, as noted in TABLE 1, below.

TABLE 1

Encoded Amino Acid Abbreviations

| Amino Acid | Three Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

Encoded Amino Acid Classes

| Class | Amino Acids |
|---|---|
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

The abbreviations used for the various exemplary antibodies disclosed herein are provided in TABLE 3, below:

TABLE 3

Antibody Abbreviations

| Clone/Name | Abbreviation | $V_H$ Sequence (FIGS. 2A-2G) | | $V_L$ Sequence (FIGS. 2A-2G) | |
|---|---|---|---|---|---|
| AD163.9.3 | muAb1 | muAb1 $V_H$ | SEQ ID NO: 101 | muAb1 $V_L$ | SEQ ID NO: 151 |
| AD166.4.4 | muAb2 | muAb2 $V_H$ | SEQ ID NO: 102 | muAb2 $V_L$ | SEQ ID NO: 152 |
| AD175.14.11 | muAb3 | muAb3 $V_H$ | SEQ ID NO: 103 | muAb3 $V_L$ | SEQ ID NO: 153 |
| AD163.10.7 | muAb4 | muAb4 $V_H$ | SEQ ID NO: 104 | muAb4 $V_L$ | SEQ ID NO: 154 |
| AD165.1.2 | muAb5 | muAb5 $V_H$ | SEQ ID NO: 105 | muAb5 $V_L$ | SEQ ID NO: 155 |
| AD163.162.1 | muAb6 | muAb6 $V_H$ | SEQ ID NO: 106 | muAb6 $V_L$ | SEQ ID NO: 156 |
| AD163.27.12 | muAb7 | muAb6 $V_H$ | SEQ ID NO: 106 | muAb7 $V_L$ | SEQ ID NO: 157 |
| AD163.7.2 | muAb8 | muAb8 $V_H$ | SEQ ID NO: 107 | muAb8 $V_L$ | SEQ ID NO: 158 |
| AD164.14.6 | muAb9 | muAb9 $V_H$ | SEQ ID NO: 108 | muAb9 $V_L$ | SEQ ID NO: 159 |
| AD164.76.3 | muAb10 | muAb10 $V_H$ | SEQ ID NO: 109 | muAb10 $V_L$ | SEQ ID NO: 160 |
| Humanized muAb6 #1 | huAb6-1 | huAb6-1 $V_H$ | SEQ ID NO: 110 | huAb6-1 $V_L$ | SEQ ID NO: 161 |
| Humanized muAb6 #2 | huAb6-2 | huAb6-2 $V_H$ | SEQ ID NO: 111 | huAb6-1 $V_L$ | SEQ ID NO: 161 |
| Humanized muAb6 #3 | huAb6-3 | huAb6-3 $V_H$ | SEQ ID NO: 112 | huAb6-1 $V_L$ | SEQ ID NO: 161 |
| Humanized muAb8 #1 | huAb8-1 | huAb8-1 $V_H$ | SEQ ID NO: 113 | huAb8-1 $V_L$ | SEQ ID NO: 162 |
| Humanized muAb8 #2 | huAb8-2 | huAb8-2 $V_H$ | SEQ ID NO: 114 | huAb8-1 $V_L$ | SEQ ID NO: 162 |
| Humanized muAb8 #3 | huAb8-3 | huAb8-3 $V_H$ | SEQ ID NO: 115 | huAb8-1 $V_L$ | SEQ ID NO: 162 |
| Humanized muAb9 #1 | huAb9-1 | huAb9-1 $V_H$ | SEQ ID NO: 116 | huAb9-1 $V_L$ | SEQ ID NO: 163 |
| Humanized muAb9 #2 | huAb9-2 | huAb9-2 $V_H$ | SEQ ID NO: 117 | huAb9-1 $V_L$ | SEQ ID NO: 163 |
| Humanized muAb9 #3 | huAb9-3 | huAb9-3 $V_H$ | SEQ ID NO: 118 | huAb9-1 $V_L$ | SEQ ID NO: 163 |
| Humanized muAb9 #4 | huAb9-4 | huAb9-1 $V_H$ | SEQ ID NO: 116 | huAb9-4 $V_L$ | SEQ ID NO: 164 |
| Humanized muAb9 #5 | huAb9-5 | huAb9-2 $V_H$ | SEQ ID NO: 117 | huAb9-4 $V_L$ | SEQ ID NO: 164 |
| Humanized muAb9 #6 | huAb9-6 | huAb9-3 $V_H$ | SEQ ID NO: 118 | huAb9-4 $V_L$ | SEQ ID NO: 164 |
| Humanized muAb9 #7 | huAb9-7 | huAb9-7 $V_H$ | SEQ ID NO: 119 | huAb9-7 $V_L$ | SEQ ID NO: 165 |
| Humanized muAb9 #8 | huAb9-8 | huAb9-8 $V_H$ | SEQ ID NO: 120 | huAb9-7 $V_L$ | SEQ ID NO: 165 |
| Humanized muAb9 #9 | huAb9-9 | huAb9-9 $V_H$ | SEQ ID NO: 121 | huAb9-9 $V_L$ | SEQ ID NO: 166 |
| Rehumanized muAb9 version #1 | huAb9 rehu#1 | huAb9 rehuVH4 $V_H$ | SEQ ID NO: 122 | huAb9 VK1 $V_L$ | SEQ ID NO: 167 |

TABLE 3-continued

Antibody Abbreviations

| Clone/Name | Abbreviation | $V_H$ Sequence (FIGS. 2A-2G) | | $V_L$ Sequence (FIGS. 2A-2G) | |
|---|---|---|---|---|---|
| Rehumanized muAb9 version #2 | huAb9 rehu#2 | huAb9 rehuVH4 $V_H$ | SEQ ID NO: 122 | huAb9 rehuVK2 $V_L$ | SEQ ID NO: 168 |
| Rehumanized muAb9 version #3 | huAb9 rehu#3 | huAb9 rehuVH3 $V_H$ | SEQ ID NO: 123 | huAb9 rehuVK1 $V_L$ | SEQ ID NO: 169 |
| Humanized muAb9 A2I | huAb9 A2I | huAb9-2$V_H$ | SEQ ID NO: 117 | huAb9A2I $V_L$ | SEQ ID NO: 170 |
| Humanized muAb9 A2V | huAb9 A2V | huAb9-2$V_H$ | SEQ ID NO: 117 | huAb9A2V $V_L$ | SEQ ID NO: 171 |

7.2. Definitions

Unless otherwise defined herein, scientific and technical terms used in connection with the present disclosure shall have the meanings that are commonly understood by those of ordinary skill in the art.

7.3. Anti-CD40 Antibodies and Binding Fragments

In one aspect, the disclosure concerns antibodies and/or binding fragments thereof that specifically bind human CD40 receptor (also known as tumor necrosis factor receptor superfamily member 5, TNFRSFS, Bp50, and CD40L receptor).

As used herein, the term "antibody" (Ab) refers to an immunoglobulin molecule that specifically binds to a particular antigen—here, CD40. In some embodiments, the anti-CD40 antibodies of the disclosure bind to human CD40 and thereby modulate, e.g., activate, the immune system. The resulting immune system response inhibits proliferation of cells such as tumor cells, and in some instances are cytotoxic to the tumor cells. Anti-CD40 antibodies of the disclosure comprise complementarity determining regions (CDRs), also known as hypervariable regions, in both the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

The antibodies of the disclosure may be polyclonal, monoclonal, genetically engineered, and/or otherwise modified in nature, including but not limited to chimeric antibodies, humanized antibodies, human antibodies, primatized antibodies, single chain antibodies, etc. In various embodiments, the antibodies comprise all or a portion of a constant region of an antibody. In some embodiments, the constant region is an isotype selected from: IgA (e.g., $IgA_1$ or $IgA_2$), IgD, IgE, IgG (e.g., $IgG_1$, $IgG_2$, $IgG_3$ or $IgG_4$), and IgM. In specific embodiments, the anti-CD40 antibodies described herein comprise an $IgG_1$. In other embodiments, the anti-CD40 antibodies comprise an $IgG_2$. In yet other embodiments, the anti-CD40 antibodies comprise an $IgG_4$. As used herein, the "constant region" of an antibody includes the natural constant region, allotypes or natural variants, such as D356E and L358M, or A431G in human $IgG_1$. See, e.g., Jefferis and Lefranc, MAbs, 1(4): 332-338 (July-August 2009).

The light constant region of an anti-CD40 antibody may be a kappa (κ) light region or a lambda (λ) region. A λ light region can be any one of the known subtypes, e.g., $λ_1$, $λ_2$, $λ_3$, or $λ_4$. In some embodiments, the anti-CD40 antibody comprises a kappa (κ) light region.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-CD40 antibodies in humans, chimeric, primatized, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585, 089; 5,693,761; 5,693,762; and 6,180,370 to Queen et al.;

EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

"Human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as LakePharma, Inc. (Belmont, Calif.) or Creative BioLabs (Shirley, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

"Primatized antibodies" comprise monkey variable regions and human constant regions. Methods for producing primatized antibodies are known in the art. See, e.g., U.S. Pat. Nos. 5,658,570; 5,681,722; and 5,693,780.

Anti-CD40 antibodies of the disclosure include full-length (intact) antibody molecules that are capable of specifically binding CD40, e.g., human CD40 (SEQ ID NO:40).

Also disclosed are anti-CD40 binding fragments that are capable of specifically binding human CD40. Examples of antibody binding fragments include by way of example and not limitation, Fab, Fab', F(ab')$_2$, Fv fragments, single chain Fv fragments and single domain fragments.

A Fab fragment contains the constant and variable domains of the light chain and the first constant domain (CH1) and the variable domain of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_2$ fragments lack the Fc fragment of an intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antibody binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for target binding.

"Single domain fragments" are composed of a single $V_H$ or $V_L$ domains which exhibit sufficient affinity to human CD40. In a specific embodiment, the single domain fragment is a camelized fragment (See, e.g., Riechmann, 1999, Journal of Immunological Methods 231:25-38).

The anti-CD40 antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using Ambryx technology (See, e.g., Wolfson, 2006, Chem. Biol. 13(10):1011-2).

The anti-CD40 antibodies or binding fragments may be antibodies or fragments whose sequences have been modified to alter at least one constant region-mediated biological effector function. For example, in some embodiments, an anti-CD40 antibody may be modified to reduce at least one constant region-mediated biological effector function relative to the unmodified antibody, e.g., reduced binding to one or more of the Fc receptors (FcγR) such as FcγRI, FcγRIIA, FcγRIIB, FcγRIIIA and/or FcγRIIIB. FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

The anti-CD40 antibody or binding fragment described herein include antibodies that have been modified to acquire or improve at least one constant region-mediated biological effector function relative to an unmodified antibody, e.g., to enhance FcγR interactions (See, e.g., US Patent Appl. No. 2006/0134709). For example, an anti-CD40 antibody of the disclosure can have a constant region that binds FcγRI, FcγRIIA, FcγRIIB, FcγRIIIA and/or FcγRIIIB with greater affinity than the corresponding wild type constant region.

Thus, antibodies of the disclosure may have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (also known as "M3," shown in FIG. 4 of U.S. Pat. No. 5,834,597) in which residues 234 and 237 (using EU numbering) are substituted with alanines. A mutant 3 (also known as "M3") variation may be used in a number of antibody isotypes, e.g., IgG$_2$.

In some embodiments, the anti-CD40 antibodies of the disclosure have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

The anti-CD40 antibodies of the disclosure can comprise modified (or variant) CH2 domains or entire Fc domains that include amino acid substitutions that increase binding to FcγRIIB and/or reduced binding to FcγRIIIA as compared to the binding of a corresponding wild-type CH2 or Fc region. Variant CH2 or variant Fc domains have been described in U.S. Patent Appl. No. 2014/0377253. A variant CH2 or variant Fc domain typically includes one or more substitutions at position 263, position 266, position 273, and position 305, wherein the numbering of the residues in the Fc domain is that of the EU index as in Kabat. In some embodiments, the anti-CD40 antibodies comprise one or more substitutions selected from V263L, V266L, V273C, V273E, V273F, V273L, V273M, V273S, V273Y, V305K, and V305W, relative to the wild-type CH2 domain. In specific embodiments, the one or more substitutions of the CH2 domain are selected from V263L, V273E, V273F, V273M, V273S, and V273Y, relative to the CH2 domain of a human IgG$_1$. For example, the one or more substitutions of an IgG$_1$ CH2 domain can be V273E. In another specific embodiment, the anti-CD40 antibody of the disclosure comprises a variant IgG$_1$ CH2 region comprising the amino acid substitution V263L.

Other examples of variant CH2 or variant Fc domains that can afford increased binding to FcγRIIB and/or reduced binding to FcγRIIIA as compared to the binding of a corresponding wild-type CH2 or Fc region include those found in Vonderheide, et al. Clin. Cancer Res., 19(5), 1035-1043 (2013), such as S267E or S267E/L328F in human IgG$_1$.

In some embodiments, the anti-CD40 antibodies or binding fragments include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-CD40 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. An exemplary substitution known to modify Fc effector function is the Fc substitution M428L, which can occur in combination with the Fc substitution T250Q. Additional specific combinations of suitable amino acid substitutions are identified in Table 1 of U.S. Pat. No. 7,217,797. Such mutations increase binding to FcRn, which protects the antibody from degradation and increases its half-life.

An anti-CD40 antibody may have one or more amino acids inserted into one or more of its CDRs, for example as described in Jung and Plückthun, 1997, Protein Engineering 10:9, 959-966; Yazaki et al., 2004, Protein Eng. Des Sel. 17(5):481-9. Epub 2004 Aug. 17; and U.S. Pat. Appl. No. 2007/0280931.

Anti-CD40 antibodies with affinity for human CD40 may be desirable for therapeutic and diagnostic uses. Accordingly, the present disclosure contemplates antibodies having binding affinity to human CD40. In specific embodiments, the anti-CD40 antibodies that bind human CD40 with an affinity of at least about 1000 nM, but may exhibit higher affinity, for example, at least about 900 nM, 800 nM, 700 nM, 600 nM, 500 nM, 400 nM, 300 nM, 250 nM, 200 nM, 150 nM, 100 nM, 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind human CD40 with an affinity in the range of about 1 pM to about 1000 nM, or an affinity ranging between any of the foregoing values.

Affinity of anti-CD40 antibodies for human CD40 can be determined using techniques well known in the art or described herein, such as for example, but not by way of limitation, ELISA, isothermal titration calorimetry (ITC), surface plasmon resonance, or fluorescent polarization assay.

Anti-CD40 antibodies generally comprise a heavy chain comprising a variable region (V$_H$) having three complementarity determining regions ("CDRs") referred to herein (in N→C order) as V$_H$ CDR #1, V$_H$ CDR #2, and V$_H$ CDR #3, and a light chain comprising a variable region (V$_L$) having three complementarity determining regions referred to herein (in N→C order) as V$_L$ CDR #1, V$_L$ CDR #2, and V$_L$ CDR #3. The amino acid sequences of exemplary CDRs, as well as the amino acid sequence of the V$_H$ and V$_L$ regions of the heavy and light chains of exemplary anti-CD40 are provided herein. Specific embodiments of anti-CD40 antibodies include these exemplary CDRs and/or V$_H$ and/or V$_L$ sequences, as well as antibodies that compete for binding human CD40 with such antibodies.

In some embodiments, the amino acid sequences of the CDRs of an anti-CD40 antibody are selected from the following sequences:

| CDR | Sequence (N→C) | Identifier |
|---|---|---|
| V$_H$ CDR#1: | GYTFTSYWIT | (SEQ ID NO: 1) |
| | GYTFTGYWIQ | (SEQ ID NO: 2) |
| | GYTFTDYYMN | (SEQ ID NO: 3) |
| | GFTFSDYYMS | (SEQ ID NO: 4) |
| | GYSITTNYNWN | (SEQ ID NO: 5) |
| | GYTFTSYWMH | (SEQ ID NO: 6) |
| | GYTFTDYYIN | (SEQ ID NO: 7) |
| | GYSITSNYYWN | (SEQ ID NO: 8) |

-continued

| CDR | Sequence (N→C) | Identifier |
|---|---|---|
| | GYSISSNYYWN | (SEQ ID NO: 9) |
| | GYDITSNYYWN | (SEQ ID NO: 10) |
| $V_H$ CDR#2: | EINPGSGSTNYNEKFKS | (SEQ ID NO: 11) |
| | EILPGGDHTKYNEKFRG | (SEQ ID NO: 12) |
| | DINPNNGGTSYNQKFKG | (SEQ ID NO: 13) |
| | FIRNKANGYTTEFSASVKG | (SEQ ID NO: 14) |
| | YIRHDGTNNYNPSLKN | (SEQ ID NO: 15) |
| | NIDPSNGETHYNQKFKD | (SEQ ID NO: 16) |
| | WIFPGSGSVYCNEQFKG | (SEQ ID NO: 17) |
| | YIRYDGSNNYNPSLKN | (SEQ ID NO: 18) |
| | NIDPSNGETHYAQKFQG | (SEQ ID NO: 19) |
| | WIFPGSGSVYSNEQFKG | (SEQ ID NO: 20) |
| | YIRYDGSNNYNPSLKS | (SEQ ID NO: 21) |
| | YIRYDGSNNYNPSLKG | (SEQ ID NO: 22) |
| $V_H$ CDR#3: | NRGTGDY | (SEQ ID NO: 31) |
| | VGGDY | (SEQ ID NO: 32) |
| | RGGLGRGTYALDY | (SEQ ID NO: 33) |
| | YGGLRQGWYFDV | (SEQ ID NO: 34) |
| | LDY | (SEQ ID NO: 35) |
| | ERIYYSGSTYDGYFDV | (SEQ ID NO: 36) |
| | SLGKFAY | (SEQ ID NO: 37) |
| $V_L$ CDR#1: | RSSQSLVHSYGNTYLH | (SEQ ID NO: 51) |
| | RSSQSLVNSNENTYLH | (SEQ ID NO: 52) |
| | RASQDISNYLN | (SEQ ID NO: 53) |
| | RASQDIRNYLN | (SEQ ID NO: 54) |
| | RSSQSLENSYGNTFLN | (SEQ ID NO: 55) |
| | SASSSLSYMH | (SEQ ID NO: 56) |
| | KASQSVVTAVA | (SEQ ID NO: 57) |
| | RSSQSLENTNGNTFLN | (SEQ ID NO: 58) |
| | RSSQSLENSNGNTFLN | (SEQ ID NO: 59) |
| $V_L$ CDR#2: | KVSNRIS | (SEQ ID NO: 61) |
| | KVFNRYS | (SEQ ID NO: 62) |
| | YTSRLHL | (SEQ ID NO: 63) |
| | YTSRLHS | (SEQ ID NO: 64) |
| | RVSNRFC | (SEQ ID NO: 65) |
| | DTSKLAS | (SEQ ID NO: 66) |
| | SASNRYT | (SEQ ID NO: 67) |
| | RVSNRFS | (SEQ ID NO: 68) |
| | RISNRFS | (SEQ ID NO: 69) |
| $V_L$ CDR#3: | SQSTHVPYT | (SEQ ID NO: 81) |
| | FQSTHVPWT | (SEQ ID NO: 82) |
| | QQGNTLPLT | (SEQ ID NO: 83) |
| | QQGKTLPWT | (SEQ ID NO: 84) |
| | LQVTHVPYT | (SEQ ID NO: 85) |
| | QQWSSNPWT | (SEQ ID NO: 86) |
| | QQYSSYPYT | (SEQ ID NO: 87) |
| | LQVTHVPFT | (SEQ ID NO: 88) |

In some embodiments, each CDR of an anti-CD40 antibody, independently of the others, is selected to correspond in sequence to the respective CDR of an antibody provided in TABLE 3. In some embodiments, an anti-CD40 antibody is an IgG, and has a $V_H$ and $V_L$ corresponding in sequence to the $V_H$ and $V_L$ of an antibody provided in TABLE 3.

In some embodiments, an anti-CD40 antibody comprises a $V_H$ chain corresponding in sequence to any one of SEQ ID NOS:101, 102, 103, 104, 105, 106, 107, 108, or 109; and a $V_L$ chain corresponding in sequence to any one of SEQ ID NOS:151, 152, 153, 154, 155, 156, 157, 158, 159, or 160. In some embodiments, an anti-CD40 antibody comprises a $V_H$ chain corresponding in sequence to SEQ ID NO:101 and a $V_L$ chain corresponding in sequence to SEQ ID NO:151. In some embodiments, an anti-CD40 antibody comprises a $V_H$ chain corresponding in sequence to SEQ ID NO:102 and a $V_L$ chain corresponding in sequence to SEQ ID NO:152. In some embodiments, an anti-CD40 antibody comprises a $V_H$ chain corresponding in sequence to SEQ ID NO:103 and a $V_L$ chain corresponding in sequence to SEQ ID NO:153. In some embodiments, an anti-CD40 antibody comprises a $V_H$ chain corresponding in sequence to SEQ ID NO:104 and a $V_L$ chain corresponding in sequence to SEQ ID NO:154. In some embodiments, an anti-CD40 antibody comprises a $V_H$ chain corresponding in sequence to SEQ ID NO:105 and a $V_L$ chain corresponding in sequence to SEQ ID NO:155. In some embodiments, an anti-CD40 antibody comprises a $V_H$ chain corresponding in sequence to SEQ ID NO:106 and a $V_L$ chain corresponding in sequence to SEQ ID NO:156. In some embodiments, an anti-CD40 antibody and comprises a $V_H$ chain corresponding in sequence to SEQ ID NO:106 and a $V_L$ chain corresponding in sequence to SEQ ID NO:157. In some embodiments, an anti-CD40 antibody and comprises a $V_H$ chain corresponding in sequence to SEQ ID NO:107 and a $V_L$ chain corresponding in sequence to SEQ ID NO:158. In some embodiments, an anti-CD40 antibody and comprises a $V_H$ chain corresponding in sequence to SEQ ID NO:108 and a $V_L$ chain corresponding in sequence to SEQ ID NO:159. In some embodiments, an anti-CD40 antibody comprises a $V_H$ chain corresponding in sequence to SEQ ID NO:109 and a $V_L$ chain corresponding in sequence to SEQ ID NO:160.

Specific exemplary embodiments of anti-CD40 antibodies with the above CDRs are described herein. In some embodiments, an anti-CD40 antibody has the CDRs of SEQ ID NOS: 1, 11, 31, 51, 61, and 81. In some embodiments, an anti-CD40 antibody has the CDRs of SEQ ID NOS: 2, 12, 32, 52, 62, and 82. In some embodiments, an anti-CD40 antibody has the CDRs of SEQ ID NOS: 3, 13, 33, 53, 63, and 83. In some embodiments, an anti-CD40 antibody has the CDRs of SEQ ID NOS: 4, 14, 34, 54, 64, and 84. In some embodiments, an anti-CD40 antibody has the CDRs of SEQ ID NOS: 5, 15, 35, 55, 65, and 85. In some embodiments, an anti-CD40 antibody has the CDRs of SEQ ID NOS: 6, 16, 36, 56, 66, and 86. In some embodiments, an anti-CD40 antibody has the CDRs of SEQ ID NOS: 6, 19, 36, 56, 66, and 86. In some embodiments, an anti-CD40 antibody has the CDRs of SEQ ID NOS: 7, 17, 37, 57, 67, and 87. In some embodiments, an anti-CD40 antibody has the CDRs of SEQ ID NOS: 7, 20, 37, 57, 67, and 87. In some embodiments, an anti-CD40 antibody has the CDRs of SEQ ID NOS: 8, 18, 35, 58, 68, and 88. In some embodiments, an anti-CD40 antibody has the CDRs of SEQ ID NOS: 9, 21, 35, 58, 68, and 88. In some embodiments, an anti-CD40 antibody has the CDRs of SEQ ID NOS: 10, 22, 35, 58, 68, and 88.

In some embodiments, an anti-CD40 antibody is suitable for administration to humans. In a specific embodiment, the anti-CD40 antibody is humanized. In another specific embodiment, the amino acid sequences of the CDRs of the anti-CD40 antibody are selected from:

| CDR | Sequence (N→C) | Identifier |
|---|---|---|
| $V_H$ CDR#1: | GYTFTSYWMH | (SEQ ID NO: 6) |
| | GYTFTDYYIN | (SEQ ID NO: 7) |
| | GYSITSNYYWN | (SEQ ID NO: 8) |
| | GYSISSNYYWN | (SEQ ID NO: 9) |
| | GYDITSNYYWN | (SEQ ID NO: 10) |
| $V_H$ CDR#2: | WIFPGSGSVYCNEQFKG | (SEQ ID NO: 17) |
| | YIRYDGSNNYNPSLKN | (SEQ ID NO: 18) |
| | NIDPSNGETHYAQKFQG | (SEQ ID NO: 19) |
| | WIFPGSGSVYSNEQFKG | (SEQ ID NO: 20) |
| | YIRYDGSNNYNPSLKS | (SEQ ID NO: 21) |
| | YIRYDGSNNYNPSLKG | (SEQ ID NO: 22) |

-continued

| CDR | Sequence (N→C) | Identifier |
|---|---|---|
| V$_H$ CDR#3: | LDY | (SEQ ID NO: 35) |
|  | ERIYYSGSTYDGYFDV | (SEQ ID NO: 36) |
|  | SLGKFAY | (SEQ ID NO: 37) |
| V$_L$ CDR#1: | SASSSLSYMH | (SEQ ID NO: 56) |
|  | KASQSVVTAVA | (SEQ ID NO: 57) |
|  | RSSQSLENTNGNTFLN | (SEQ ID NO: 58) |
| V$_L$ CDR#2: | DTSKLAS | (SEQ ID NO: 66) |
|  | SASNRYT | (SEQ ID NO: 67) |
|  | RVSNRFS | (SEQ ID NO: 68) |
| V$_L$ CDR#3: | QQWSSNPWT | (SEQ ID NO: 86) |
|  | QQYSSYPYT | (SEQ ID NO: 87) |
|  | LQVTHVPFT | (SEQ ID NO: 88) |

In some embodiments, an anti-CD40 antibody comprises a V$_H$ chain corresponding in sequence to any one of SEQ ID NOS:110, 111, 112, 113, 114, 115, 116, 117, 118, 119, 120, 121, 122, or 123; and a V$_L$ chain corresponding in sequence to any one of SEQ ID NOS:161, 162, 163, 164, 165, 166, 167, 168, 169, 170, or 171. In some embodiments, an anti-CD40 antibody comprises a V$_H$ chain corresponding in sequence to SEQ ID NO:110 and a V$_L$ chain corresponding in sequence to SEQ ID NO:161. In some embodiments, an anti-CD40 antibody comprises a V$_H$ chain corresponding in sequence to SEQ ID NO:111 and a V$_L$ chain corresponding in sequence to SEQ ID NO:161. In some embodiments, an anti-CD40 antibody comprises a V$_H$ chain corresponding in sequence to SEQ ID NO:112 and a V$_L$ chain corresponding in sequence to SEQ ID NO:161. In some embodiments, an anti-CD40 antibody comprises a V$_H$ chain corresponding in sequence to SEQ ID NO:113 and a V$_L$ chain corresponding in sequence to SEQ ID NO:162. In some embodiments, an anti-CD40 antibody comprises a V$_H$ chain corresponding in sequence to SEQ ID NO:114 and a V$_L$ chain corresponding in sequence to SEQ ID NO:162. In some embodiments, an anti-CD40 antibody comprises a V$_H$ chain corresponding in sequence to SEQ ID NO:115 and a V$_L$ chain corresponding in sequence to SEQ ID NO:162. In some embodiments, an anti-CD40 antibody comprises a V$_H$ chain corresponding in sequence to SEQ ID NO:116 and a V$_L$ chain corresponding in sequence to SEQ ID NO:163. In some embodiments, an anti-CD40 antibody comprises a V$_H$ chain corresponding in sequence to SEQ ID NO:117 and a V$_L$ chain corresponding in sequence to SEQ ID NO:163. In some embodiments, an anti-CD40 antibody comprises a V$_H$ chain corresponding in sequence to SEQ ID NO:118 and a V$_L$ chain corresponding in sequence to SEQ ID NO:163. In some embodiments, an anti-CD40 antibody comprises a V$_H$ chain corresponding in sequence to SEQ ID NO:116 and a V$_L$ chain corresponding in sequence to SEQ ID NO:164. In some embodiments, an anti-CD40 antibody comprises a V$_H$ chain corresponding in sequence to SEQ ID NO:117 and a V$_L$ chain corresponding in sequence to SEQ ID NO:164. In some embodiments, an anti-CD40 antibody comprises a V$_H$ chain corresponding in sequence to SEQ ID NO:119 and a V$_L$ chain corresponding in sequence to SEQ ID NO:165. In some embodiments, an anti-CD40 antibody comprises a V$_H$ chain corresponding in sequence to SEQ ID NO:120 and a V$_L$ chain corresponding in sequence to SEQ ID NO:165. In some embodiments, an anti-CD40 antibody comprises a V$_H$ chain corresponding in sequence to SEQ ID NO:121 and a V$_L$ chain corresponding in sequence to SEQ ID NO:166. In some embodiments, an anti-CD40 antibody comprises a V$_H$ chain corresponding in sequence to SEQ ID NO:117 and a V$_L$ chain corresponding in sequence to SEQ ID NO:167. In some embodiments, an anti-CD40 antibody comprises a V$_H$ chain corresponding in sequence to SEQ ID NO:117 and a V$_L$ chain corresponding in sequence to SEQ ID NO:168. In some embodiments, an anti-CD40 antibody comprises a V$_H$ chain corresponding in sequence to SEQ ID NO:117 and a V$_L$ chain corresponding in sequence to SEQ ID NO:169. In some embodiments, an anti-CD40 antibody comprises a V$_H$ chain corresponding in sequence to SEQ ID NO:117 and a V$_L$ chain corresponding in sequence to SEQ ID NO:170. In some embodiments, an anti-CD40 antibody comprises a V$_H$ chain corresponding in sequence to SEQ ID NO:117 and a V$_L$ chain corresponding in sequence to SEQ ID NO:171. In some embodiments, an anti-CD40 antibody comprises a V$_H$ chain corresponding in sequence to SEQ ID NO:118 and a V$_L$ chain corresponding in sequence to SEQ ID NO:164. In some embodiments, an anti-CD40 antibody comprises a V$_H$ chain corresponding in sequence to SEQ ID NO:122 and a V$_L$ chain corresponding in sequence to SEQ ID NO:167. In some embodiments, an anti-CD40 antibody comprises a V$_H$ chain corresponding in sequence to SEQ ID NO:122 and a V$_L$ chain corresponding in sequence to SEQ ID NO:168. In some embodiments, an anti-CD40 antibody comprises a V$_H$ chain corresponding in sequence to SEQ ID NO:123 and a V$_L$ chain corresponding in sequence to SEQ ID NO:169.

In some embodiments, the anti-CD40 antibodies compete for binding human CD40 in in vitro assays with a reference antibody. In some embodiments, the anti-CD40 antibodies compete for binding human CD40 on cells expressing human CD40. The reference antibody may be any of the anti-CD40 antibodies described herein. In some embodiments, the reference antibody is an antibody provided in TABLE 3. In specific embodiments, the reference antibody is selected from antibody AD163.9.3 ("muAb1"); antibody AD166.4.4 ("muAb2"); antibody AD175.14.11 ("muAb3"); antibody AD163.10.7 ("muAb4"); antibody AD165.1.2 ("muAb5"); antibody AD163.162.1 ("muAb6"); antibody AD163.27.12 ("muAb7"); antibody AD163.7.2 ("muAb8"); antibody AD164.14.6 ("muAb9"); and antibody AD164.76.2 ("muAb10"). In some embodiments, the reference antibody is a humanized version of an antibody provided in TABLE 3. In some embodiments, the reference antibody is a humanized version of muAb6, muAb8, or muAb9. In a specific embodiment, the reference antibody is huAb9-2. In another embodiment, the reference antibody is huAb9-5. In another specific embodiment, the reference antibody is huAb9 A2I.

Post-translational modifications to the sequences of an anti-CD40 antibody may occur, such as cleavage of one or more (e.g., 1, 2, 3, or more) amino acid residues on the C-terminal end of the antibody heavy chain.

In some embodiments, an anti-CD40 antibody comprises a heavy chain according to any one of SEQ ID NOS: 130-135, and a light chain according to SEQ ID NOS: 140-142. In certain embodiments, an anti-CD40 antibody comprises a heavy chain according to SEQ ID NOS: 130 or 131, and a light chain according to SEQ ID NO: 140. In certain embodiments, an anti-CD40 antibody comprises a heavy chain according to SEQ ID NOS: 132 or 133, and a light chain according to SEQ ID NO: 140. In certain embodiments, an anti-CD40 antibody comprises a heavy chain according to SEQ ID NOS: 134 or 135, and a light chain according to SEQ ID NO: 140. In certain embodiments, an anti-CD40 antibody comprises a heavy chain according to SEQ ID NOS: 132 or 133, and a light chain according to SEQ ID NO: 141. In certain embodiments, an anti-CD40 antibody comprises a heavy chain according to SEQ ID NOS: 132 or 133, and a light chain according to SEQ ID NO: 142.

The anti-CD40 antibodies described herein generally bind specifically to human CD40. Cross reactivity of the antibodies for binding to CD40 from other species, for example, from monkey, e.g., cynomolgus monkey, may offer advantages, such as the ability to test in monkey animal models for biological activity. Such animal model testing may be used to screen anti-CD40 antibodies to select for properties, e.g., favorable pharmacokinetics. In some embodiments, the anti-CD40 antibodies bind to cynomolgus CD40.

Assays for competition include, but are not limited to, a radioactive material labeled immunoassay (RIA), an enzyme-linked immunosorbent assay (ELISA), a sandwich ELISA, fluorescence activated cell sorting (FACS) assays, and surface plasmon resonance assays.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing human CD40 are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("conc$_{80\%}$") under the assay conditions (e.g., a specified density of cells) is first determined, and a competition assay carried out with 10× conc$_{80\%}$ of unlabeled test antibody and conc$_{80\%}$ of labeled reference antibody.

The inhibition can be expressed as an inhibition constant, or $K_i$, which is calculated according to the following formula:

$$K_i = IC_{50}/(1+[\text{reference }Ab\text{ concentration}]/K_d),$$

where IC$_{50}$ is the concentration of test antibody that yields a 50% reduction in binding of the reference antibody and $K_d$ is the dissociation constant of the reference antibody, a measure of its affinity for human CD40. Antibodies that compete with anti-CD40 antibodies disclosed herein can have a $K_i$ from 10 pM to 1000 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

The anti-CD40 antibodies described herein are capable of agonizing human CD40 (SEQ ID NO:40) by activating human CD40 via at least two mechanisms of action. In some embodiments, an anti-CD40 antibody binds human CD40 in the absence of CD40L (SEQ ID NO:41), and enhances the signaling of human CD40. In some embodiments, an anti-CD40 antibody binds the human CD40L-CD40 bound complex, and enhances the signaling of human CD40. In some embodiments, an anti-CD40 antibody competes for binding human CD40 (SEQ ID NO:40) with a control antibody selected from a humanized antibody listed in TABLE 3, and activates human CD40 independent of human CD40 ligand (SEQ ID NO:41), i.e., in the absence or presence of CD40L.

The effect of the anti-CD40 antibodies on human CD40-CD40L interaction can be determined by assays known in the art, such as the CD40L competitive assay described in Example 2. A ratio of an OD$_{450}$ measured in samples containing anti-CD40 antibodies to an OD$_{450}$ taken from isotype control antibody samples (an "OD$_{450}$ ratio") can be used to determine the effect of an anti-CD40 antibody on human CD40L binding to human CD40. A OD$_{450}$ ratio of 1 indicates no effect; less than 1 indicates competition with CD40L; greater than 1 indicates an enhancement of CD40L binding with CD40. In some embodiments, the anti-CD40 antibody increases (i.e., enhances) binding of human CD40L (SEQ ID NO:41) to human CD40 (SEQ ID NO:40) as determined by OD$_{450}$ ratio. An enhancement of CD40L binding to CD40 by OD$_{450}$ ratio is at least about 1.2, such as about 1.3, 1.4, 1.5, 1.6, 1.7, 1.8, 1.9, 2.0, 2.2, 2.4, 2.5, 2.6, 2.8, 3.0 or greater.

A specific assay and assay conditions useful for assessing whether an antibody competes for binding human CD40 with a reference antibody as described herein is provided in Example 2. Antibody competition can be determined by a surface plasmon resonance assay as described in Example 2, or in competitive binding protocol described in Section 8.4.3.

While an agonistic anti-CD40 antibody activates the immune system to exert an antitumor effect, broad systemic immune activation across all cell types may lead to undesired side effects. Accordingly, in some embodiments, an anti-CD40 antibody activates a dendritic cell-mediated immune response selectively over a B-cell immune response as compared to a reference anti-CD40 antibody. In some embodiments, the reference anti-CD40 antibody is CP-870,893. In some embodiments, an anti-CD40 antibody has a similar activity, e.g., a production of IL-12p70 at a given dose, within about 200%, such as within about 180%, 150%, 130%, 110%, 100%, 90%, 80%, 70%, 60%, 50%, 40%, 30%, 25%, 20%, 15%, 10%, or about 5%, in activating a dendritic cell as compared to the production of IL-12p70 at the same dose of a reference anti-CD40 antibody in the assay described in Section 8.1.3. In some embodiments, an anti-CD40 antibody has a lower potency in activating a B cell as compared to a reference anti-CD40 antibody. The B cell EC50 ratio of the anti-CD40 antibody to the reference anti-CD40 antibody can be greater than about 1.5, such as about 2, 3, 4, 5, 6, 8, 10, 15, 20, 30, 40, 50 or greater, in the assay described in Section 8.5.3. In some embodiments, an anti-CD40 antibody has a similar activity in activating a dendritic cell and a lower potency in activating a B cell as compared to a reference anti-CD40 antibody.

7.4. Polynucleotides Encoding the Anti-CD40 Antibodies, Expression Systems and Methods of Making the Antibodies The present disclosure encompasses nucleic acid molecules encoding immunoglobulin light and heavy chain genes for anti-CD40 antibodies, vectors comprising such nucleic acids, and host cells capable of producing the anti-CD40 antibodies of the disclosure.

An anti-CD40 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, NY, 1989), Current Protocols in Molecular Biology (Ausubel, F. M. et al., eds., Greene Publishing Associates, 1989) and in U.S. Pat. No. 4,816,397.

To generate nucleic acids encoding such anti-CD40 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-CD40 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2, CH3 and, optionally, CH4). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence (Gly4~Ser)$_3$ (SEQ ID NO:200), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-CD40 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-CD40 antibody-related light or heavy chain sequences, the expression vector can already carry antibody constant region sequences. For example, one approach to converting the anti-CD40 monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-CD40 antibody of this disclosure.

Recombinant DNA technology can also be used to remove some or all of the DNA encoding either or both of the light and heavy chains that is not necessary for binding to human CD40. The molecules expressed from such truncated DNA molecules are also encompassed by the antibodies of the disclosure.

For recombinant expression of an anti-CD40 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-CD40 antibody, further alterations or mutations can be introduced into the coding sequence, for example to generate nucleic acids encoding antibodies with different CDR sequences, antibodies with reduced affinity to the Fc receptor, or antibodies of different subclasses.

The anti-CD40 antibodies of the disclosure can also be produced by chemical synthesis (e.g., by the methods described in Solid Phase Peptide Synthesis, $2^{nd}$ ed., 1984 The Pierce Chemical Co., Rockford, Ill.). Variant antibodies can also be generated using a cell-free platform (See, e.g., Chu et al., Biochemia No. 2, 2001 (Roche Molecular Biologicals) and Murray et al., 2013, Current Opinion in Chemical Biology, 17:420-426).

Once an anti-CD40 antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-CD40 antibodies of the present disclosure can be fused to heterologous polypeptide sequences described herein or otherwise known in the art to facilitate purification.

Once isolated, the anti-CD40 antibody can, if desired, be further purified, e.g., by high performance liquid chromatography (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

7.5. Pharmaceutical Compositions

The anti-CD40 antibodies described herein may be in the form of compositions comprising the antibody and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a subject, e.g., a human subject, i.e., patient). The pharmaceutical composition can be administered to a subject by a variety of routes such as orally, transdermally, subcutaneously, intranasally, intravenously, intramuscularly, intratumorally, intrathecally, topically or locally. The most suitable route for administration in any given case will depend on the particular antibody, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an anti-CD40 antibody described herein per dose. The quantity of anti-CD40 antibody included in a unit dose will depend on the disease being treated, as well as other factors as are well known in the art. Such unit dosages may be in the form of a lyophilized dry powder containing an amount of antibody suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of the anti-CD40 antibody suitable for a single administration.

The pharmaceutical compositions may also be supplied in bulk form containing quantities of anti-CD40 antibody suitable for multiple administrations.

Pharmaceutical compositions may be prepared for storage as lyophilized formulations or aqueous solutions by mixing an antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), phosphate buffers (e.g., phosphoric acid-monosodium phosphate mixture, phosphoric acid-disodium phosphate mixture, monosodium phosphate-disodium phosphate mixture, etc.), gluconate buffers (e.g., gluconic acid-sodium gluconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, fumarate buffers, histidine buffers and trimethylamine salts such as 2-amino-2-hydroxymethyl-propane-1,3-diol (i.e., Tris, THAM, or tris(hydroxymethyl)aminomethane) can be used.

Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, leucine, 2-phenylalanine, glutamic acid, threonine, etc., organic sugars or sugar alcohols, such as lactose, trehalose, stachyose, mannitol, sorbitol, xylitol, ribitol, myoinositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (e.g., peptides of 10 residues or fewer); hydrophilic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 weight % per weight of anti-CD40 antibody.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), poloxamers (184, 188 etc.), and pluronic polyols. Non-ionic surfactants may be present in a range of about 0.05 mg/mL to about 1.0 mg/mL.

A specific exemplary embodiment of an aqueous composition suitable for administration via intravenous infusion comprises 10 mg/mL of anti-CD40 antibody, 15 mM histidine buffer, pH 6.0, 8.0% (w/v) sucrose, and 0.05% (w/v) polysorbate 80. In certain embodiments, the anti-CD40 antibody is any one of the humanized antibodies described in TABLE 3. The composition may be in the form of a lyophilized powder that, upon reconstitution with 2.0 mL sterile water or other solution suitable for injection or infusion (for example, 0.9% saline, Ringer's solution, lactated Ringer's solution, etc.) provides the above aqueous composition. The composition, or other embodiments of compositions, may also be in the form of a syringe or other device suitable for injection and/or infusion pre-filled with a quantity of composition suitable for a single administration of the anti-CD40 antibody.

7.6. Methods of Use 7.6.1. Therapeutic Benefit

Data provided herein demonstrate that anti-CD40 antibodies described herein that agonize CD40 in the presence of tumor cells exert potent anti-tumor activity against these solid tumors in vivo. Accordingly, the anti-CD40 antibodies, binding fragments, and/or pharmaceutical compositions comprising the anti-CD40 antibodies may be used therapeutically to treat solid tumors.

Generally, the methods involve administering to a human patient having a solid tumor an effective amount of an anti-CD40 antibody that agonizes CD40, and kills and/or reduces proliferation of tumor cells to provide therapeutic benefit. Solid tumors that may be treated with the anti-CD40 antibody include, but are not limited to, adrenal cancers, bone cancers, brain cancers, breast cancers, colorectal cancers, esophageal cancers, eye cancers, gastric cancers, head and neck cancers, kidney cancers, liver cancers, lung cancers (e.g., non-small cell lung cancer, mesothelioma), head and neck cancers (e.g., squamous cell carcinoma of the head and neck), lymphomas (e.g., B cell lymphomas), melanomas (e.g., advanced malignant melanoma, cutaneous melanoma), oral cancers, ovarian cancers, penile cancers, prostate cancers, pancreatic cancers, skin cancers, testicular cancers, thyroid cancers, uterine cancers, and vaginal cancers. In some embodiments, the solid tumor is head and neck cancer, lung cancer, melanoma or pancreatic cancer.

The cancer may be newly diagnosed and naïve to treatment, or may be relapsed, refractory, or relapsed and refractory, or a metastatic form of a solid tumor. Indeed, in vivo data in mouse PC3 prophylactic models (FIG. 12) show that the anti-CD40 antibodies are effective in reducing tumor size in comparison to dosing with isotype antibody.

Without wishing to be limited by theory, it is believed that an anti-CD40 antibody activates the immune system by agonizing CD40. The subsequent immune response then exerts an antitumor effect on adjacent tumor cells, without regard to CD40 expression levels. Accordingly, an anti-CD40 antibody of the disclosure is expected to be effective against CD40-positive or CD40-negative solid tumors.

An anti-CD40 antibody of the disclosure may be administered alone (monotherapy) or adjunctive to, or with, other anti-cancer therapies and/or targeted or non-targeted anti-cancer agents. Whether administered as monotherapy or adjunctive to, or with, other therapies or agents, an amount of anti-CD40 antibody is administered such that the overall treatment regimen provides therapeutic benefit.

By therapeutic benefit is meant that the use of anti-CD40 antibodies to treat cancer in a patient results in any demonstrated clinical benefit compared with no therapy (when appropriate) or to a known standard of care. Clinical benefit can be assessed by any method known to one of ordinary skill in the art. In one embodiment, clinical benefit is assessed based on objective response rate (ORR) (determined using RECIST version 1.1), duration of response (DOR), progression-free survival (PFS), and/or overall survival (OS). In some embodiments, a complete response indicates therapeutic benefit. In some embodiments, a partial response indicates therapeutic benefit. In some embodiments, stable disease indicates therapeutic benefit. In some embodiments, an increase in overall survival indicates therapeutic benefit. In some embodiments, therapeutic benefit may constitute an improvement in time to disease progression and/or an improvement in symptoms or quality of life. In other embodiments, therapeutic benefit may not translate to an increased period of disease control, but rather a markedly reduced symptom burden resulting in improved quality of life. As will be apparent to those of skill in the art, a therapeutic benefit may be observed using the anti-CD40 antibodies alone (monotherapy) or adjunctive to, or with, other anti-cancer therapies and/or targeted or non-targeted anti-cancer agents.

Typically, therapeutic benefit is assessed using standard clinical tests designed to measure the response to a new treatment for cancer. To assess the therapeutic benefits of the anti-CD40 antibodies described herein one or a combination of the following tests can be used: (1) the Response Evaluation Criteria In Solid Tumors (RECIST) version 1.1, (2) the Eastern Cooperative Oncology Group (ECOG) Performance Status, (3) immune-related response criteria (irRC), (4) disease evaluable by assessment of tumor antigens, (5) validated patient reported outcome scales, and/or (6) Kaplan-Meier estimates for overall survival and progression free survival.

Assessment of the change in tumor burden is an important feature of the clinical evaluation of cancer therapeutics. Both tumor shrinkage (objective response) and time to the development of disease progression are important endpoints in cancer clinical trials. Standardized response criteria, known as RECIST (Response Evaluation Criteria in Solid Tumors), were published in 2000. An update (RECIST 1.1) was released in 2009. RECIST criteria are typically used in clinical trials where objective response is the primary study endpoint, as well as in trials where assessment of stable disease, tumor progression or time to progression analyses are undertaken because these outcome measures are based on an assessment of anatomical tumor burden and its change over the course of the trial. TABLE 4 provides the definitions of the response criteria used to determine objective tumor response to a study drug, such as the anti-CD40 antibodies described herein.

TABLE 4

| Response | Criteria |
| --- | --- |
| Complete Response (CR) | Disappearance of all target lesions. Any pathological lymph nodes (whether target or non-target) must have reduction in short axis to <10 mm. |
| Partial Response (PR) | At least a 30% decrease in the sum of diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) | Neither sufficient shrinkage to qualify for PR nor sufficient increase to qualify for PD, taking as reference the smallest sum diameters while on study. |

Secondary outcome measures that can be used to determine the therapeutic benefit of the anti-CD40 antibodies described herein include, Objective Response Rate (ORR), Progression Free Survival (PFS), Overall Survival (OS), Duration of Overall Response (DOR), and Depth of Response (DpR). ORR is defined as the proportion of the participants who achieve a complete response (CR) or partial response (PR). PFS is defined as the time from the first dose date of an anti-CD40 antibody to either disease progression or death, whichever occurs first. OS is defined as the length of time from either the date of diagnosis or the start of treatment for a disease, that patients diagnosed with the disease are still alive. DOR is defined as the time from the participant's initial CR or PR to the time of disease progression. DpR is defined as the percentage of tumor shrinkage observed at the maximal response point compared to baseline tumor load. Clinical endpoints for both ORR and PFS can be determined based on RECIST 1.1 criteria described above.

The ECOG Scale of Performance Status shown in TABLE 5 is used to describe a patient's level of functioning in terms of their ability to care for themselves, daily activity, and physical ability. The scale was developed by the Eastern Cooperative Oncology Group (ECOG), now part of the ECOG-ACRIN Cancer Research Group, and published in 1982.

TABLE 5

| Grade | ECOG Performance Status |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

Another set of criteria that can be used to characterize fully and to determine response to immunotherapeutic agents, such as antibody-based cancer therapies, is the immune-related response criteria (irRC), which was developed for measurement of solid tumors in 2009, and updated in 2013 (Wolchok, et al. Clin. Cancer Res. 2009; 15(23): 7412-7420 and Nishino, et al. Clin. Cancer Res. 2013; 19(14): 3936-3943, each of which is incorporated by reference in its entirety). The updated irRC criteria are typically used to assess the effect of an immunotherapeutic agent, such as an anti-CD40 antibody described herein, on tumor burden, and defines response according to TABLE 6.

TABLE 6

| Response | Criteria |
|---|---|
| Complete Response (CR) | Disappearance of all target lesions in two consecutive observations not less than 4 weeks apart |
| Partial Response (PR) | At least a 30% decrease in the sum of the longest diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). (Note: the appearance of one or more new lesions is not considered progression. The measurement of new lesions is included in the sum of the measurements). |
| Stable Disease (SD) | Neither sufficient shrinkage to qualify for PR nor sufficient increase to qualify for PD, taking as reference the smallest sum diameters while on study. |

One exemplary therapeutic benefit resulting from the use of anti-CD40 antibodies described herein to treat solid tumors, whether administered as monotherapy or adjunctive to, or with, other therapies or agents, is a complete response. Another exemplary therapeutic benefit resulting from the use of anti-CD40 antibodies described herein to treat solid tumors, whether administered as monotherapy or adjunctive to, or with, other therapies or agents, is a partial response.

Validated patient reported outcome scales can also be used to denote response provided by each patient through a specific reporting system. Rather than being disease focused, such outcome scales are concerned with retained function while managing a chronic condition. One non-limiting example of a validated patient reported outcome scale is PROMIS® (Patient Reported Outcomes Measurement Information System) from the United States National Institutes of Health. For example, PROMIS® Physical Function Instrument for adult cancer patients can evaluate self-reported capabilities for the functioning of upper extremities (e.g., dexterity), lower extremities (e.g., walking or mobility), and central regions (e.g., neck, back mobility), and includes routine daily activities, such as running errands.

Kaplan-Meier curves (Kaplan and Meier, J. Am. Stat. Assoc. 1958; 53(282): 457-481) can also be used to estimate overall survival and progression free survival for cancer patients undergoing anti-CD40 antibody therapy in comparison to standard of care.

7.6.2. Adjunctive Therapies

The anti-CD40 antibodies may be used adjunctive to, or with, other agents or treatments having anti-cancer properties. When used adjunctively, the anti-CD40 antibody and other agent(s) may be formulated together in a single, combination pharmaceutical formulation, or may be formulated and administered separately, either on a single coordinated dosing regimen or on different dosing regimens. Agents administered adjunctive to or with the anti-CD40 antibodies will typically have complementary activities to the anti-CD40 antibodies such that the antibodies and other agents do not adversely affect each other.

Agents that may be administered adjunctive to or with an anti-CD40 antibody include, but are not limited to, alkylating agents, angiogenesis inhibitors, antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin (mTor) inhibitors, microRNAs, mitogen-activated extracellular signal-regulated kinase inhibitors, non-steroidal anti-inflammatory drugs (NSAIDs), poly ADP (adenosine diphosphate)-ribose polymerase (PARP) inhibitors, platinum chemotherapeutics, Bruton's tyrosine kinase (BTK) inhibitors (e.g., ibrutinib, acalabrutinib), polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, as well as combinations of one or more of these agents.

Examples of immunologicals include, but are not limited to, interferons, immune checkpoint inhibitors, and other immune-enhancing agents. Interferons include interferon alpha, interferon alpha-2a, interferon alpha-2b, interferon beta, interferon gamma-1a, ACTIMMUNE® (interferon gamma-2b) or interferon gamma-n1, combinations thereof and the like. Immune check point inhibitors include antibodies that target PD-1 (e.g., pembrolizumab and nivolumab), PD-L1 (e.g., durvalumab, atezolizumab, avelumab, MEDI4736, MSB0010718C and MPDL3280A), and CTLA4 (cytotoxic lymphocyte antigen 4; e.g., ipilimumab, tremelimumab). Immune-enhancing agents include anti-OX40 agonist antibodies that activate T cells. In certain embodiments, a humanized anti-CD40 antibody shown in TABLE 3 is administered adjunctive to pembrolizumab. In other certain embodiments, a humanized anti-CD40 antibody shown in TABLE 3 is administered adjunctive to nivolumab.

An anti-CD40 antibody may also be used to enhance the efficacy of radiation therapy. Examples of radiation therapy include external beam radiation therapy, internal radiation therapy (i.e., brachytherapy) and systemic radiation therapy.

7.7. Dosages and Administration Regimens

The amount of anti-CD40 antibodies administered will depend upon a variety of factors, including but not limited to, the particular type of solid tumor treated, the stage of the solid tumor being treated, the mode of administration, the frequency of administration, the desired therapeutic benefit, and other parameters such as the age, weight and other characteristics of the patient, etc. Determination of dosages effective to provide therapeutic benefit for specific modes and frequency of administration is within the capabilities of those skilled in the art.

Dosages effective to provide therapeutic benefit may be estimated initially from in vivo animal models or clinical. Suitable animal models for a wide variety of diseases are known in the art.

The anti-CD40 antibodies disclosed herein may be administered by any route appropriate to the condition to be treated. In some embodiments, the anti-CD40 antibody is any one of the humanized antibodies listed in TABLE 3. An anti-CD40 antibody will typically be administered parenterally, i.e., infusion, subcutaneous, intramuscular, intravenous (IV), intradermal, intrathecal, bolus, intratumoral (IT) injection or epidural ((Shire et al., 2004, *J. Pharm. Sciences* 93(6):1390-1402)). In one embodiment, an anti-CD40 antibody is provided as a lyophilized powder in a vial. The vials may contain 21 mg of anti-CD40 antibody. Prior to administration, the lyophilized powder is reconstituted with sterile water for injection (SWFI) or other suitable medium to provide a solution containing 10 mg/mL anti-CD40 antibody. In some embodiments, the resulting reconstituted solution is further diluted with saline or other suitable medium and administered via an IV infusion twice every 7 days, once every 7 days, once every 14 days, once every 21 days, once every 28 days, once every 35 days, once every 42 days, once every 49 days, or once every 56 days. In some embodiments, for the first cycle, the infusion occurs over 90 minutes. In some embodiments, subsequent infusions are over 60 minutes. In other embodiments, the resulting reconstituted solution is further diluted with saline or other suitable medium and administered via an IT injection twice every 7 days, once every 7 days, once every 14 days, once every 21 days, once every 28 days, once every 35 days, once every 42 days, once every 49 days, or once every 56 days.

In one exemplary embodiment, an anti-CD40 antibody is any one of the humanized antibodies listed in TABLE 3. The anti-CD40 antibody is administered as an IV infusion once every 7 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg.

In another exemplary embodiment, an anti-CD40 antibody is any one of the humanized antibodies listed in TABLE 3. The anti-CD40 antibody is administered as an IV infusion once every 14 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg.

In another exemplary embodiment, an anti-CD40 antibody is any one of the humanized antibodies listed in TABLE 3. The anti-CD40 antibody is administered as an IV infusion once every 28 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg.

In another exemplary embodiment, an anti-CD40 antibody is any one of the humanized antibodies listed in TABLE 3. The anti-CD40 antibody is administered as an IT injection once every 7 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg.

In another exemplary embodiment, an anti-CD40 antibody is any one of the humanized antibodies listed in TABLE 3. The anti-CD40 antibody is administered as an IT injection once every 14 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg.

In another exemplary embodiment, an anti-CD40 antibody is any one of the humanized antibodies listed in TABLE 3. The anti-CD40 antibody is administered as an IT injection once every 28 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg.

When administered adjunctive to or with other agents, such as other chemotherapeutic agents, the anti-CD40 antibodies may be administered on the same schedule as the other agent(s), or on a different schedule. When administered on the same schedule, the anti-CD40 antibody may be administered before, after, or concurrently with the other agent. In some embodiments where an anti-CD40 antibody is administered adjunctive to, or with, standards of care, the anti-CD40 antibody may be initiated prior to commencement of the standard therapy, for example a day, several days, a week, several weeks, a month, or even several months before commencement of standard of care therapy.

In one exemplary embodiment, an anti-CD40 antibody is used adjunctive to nivolumab (OPDIVO®) to treat non-small cell lung cancer. In some embodiments, the anti-CD40 antibody is any one of the humanized antibodies listed in TABLE 3. The anti-CD40 antibody is administered via IV infusion once every 7 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg. Nivolumab is administered by intravenous infusion at a dose of 3 mg/kg over 60 minutes once every two weeks. The adjunctive anti-CD40 antibody/nivolumab therapy is continued until disease progression or no longer tolerated by the patient.

In another exemplary embodiment, an anti-CD40 antibody is used adjunctive to nivolumab (OPDIVO®) to treat non-small cell lung cancer. In some embodiments, the anti-CD40 antibody is any one of the humanized antibodies listed in TABLE 3. The anti-CD40 antibody is administered via IV infusion once every 14 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg. Nivolumab is administered by intravenous infusion at a dose of 3 mg/kg over 60 minutes once every two weeks. The adjunctive anti-CD40 antibody/nivolumab therapy is continued until disease progression or no longer tolerated by the patient.

In another exemplary embodiment, an anti-CD40 antibody is used adjunctive to nivolumab (OPDIVO®) to treat non-small cell lung cancer. In some embodiments, the anti-CD40 antibody is any one of the humanized antibodies listed in TABLE 3. The anti-CD40 antibody is administered via IV infusion once every 28 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg. Nivolumab is administered by intravenous infusion at a dose of 3 mg/kg over 60 minutes once every two weeks. The adjunctive anti-CD40 antibody/nivolumab therapy is continued until disease progression or no longer tolerated by the patient.

In another exemplary embodiment, an anti-CD40 antibody is used adjunctive to nivolumab (OPDIVO®) to treat non-small cell lung cancer. In some embodiments, the anti-CD40 antibody is any one of the humanized antibodies listed in TABLE 3. The anti-CD40 antibody is administered as an IT injection once every 7 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg. Nivolumab is administered by intravenous infusion at a dose of 3 mg/kg over 60 minutes once every two weeks. The adjunctive anti-CD40 antibody/nivolumab therapy is continued until disease progression or no longer tolerated by the patient.

In another exemplary embodiment, an anti-CD40 antibody is used adjunctive to nivolumab (OPDIVO®) to treat non-small cell lung cancer. In some embodiments, the anti-CD40 antibody is any one of the humanized antibodies listed in TABLE 3. The anti-CD40 antibody is administered as an IT injection once every 14 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg. Nivolumab is administered by intravenous infusion at a dose of 3 mg/kg over 60 minutes once every two weeks. The adjunctive anti-CD40 antibody/nivolumab therapy is continued until disease progression or no longer tolerated by the patient.

In another exemplary embodiment, an anti-CD40 antibody is used adjunctive to nivolumab (OPDIVO®) to treat non-small cell lung cancer. In some embodiments, the anti-CD40 antibody is any one of the humanized antibodies listed in TABLE 3. The anti-CD40 antibody is administered as an IT injection once every 28 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg. Nivolumab is administered by intravenous infusion at a dose of 3 mg/kg over 60 minutes once every two weeks. The adjunctive anti-CD40 antibody/nivolumab therapy is continued until disease progression or no longer tolerated by the patient.

In another exemplary embodiment, an anti-CD40 antibody is used adjunctive to pembrolizumab (Keytruda®) to treat non-small cell lung cancer. In some embodiments, the anti-CD40 antibody is any one of the humanized antibodies listed in TABLE 3. The anti-CD40 antibody is administered via IV infusion once every 7 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg. Pembrolizumab is administered by intravenous infusion at a dose of 2 mg/kg over 30 minutes once every three weeks. The adjunctive anti-CD40 antibody/pembrolizumab therapy is continued until disease progression or no longer tolerated by the patient.

In another exemplary embodiment, an anti-CD40 antibody is used adjunctive to pembrolizumab (Keytruda®) to treat non-small cell lung cancer. In some embodiments, the anti-CD40 antibody is any one of the humanized antibodies listed in TABLE 3. The anti-CD40 antibody is administered via IV infusion once every 14 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg. Pembrolizumab is administered by intravenous infusion at a dose of 2 mg/kg over 30 minutes once every three weeks. The adjunctive anti-CD40 antibody/pembrolizumab therapy is continued until disease progression or no longer tolerated by the patient.

In another exemplary embodiment, an anti-CD40 antibody is used adjunctive to pembrolizumab (Keytruda®) to treat non-small cell lung cancer. In some embodiments, the anti-CD40 antibody is any one of the humanized antibodies listed in TABLE 3. The anti-CD40 antibody is administered via IV infusion once every 28 days at 0.005 mg/kg, 0.01 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.2 mg/kg, 2.4 mg/kg, 2.6 mg/kg, 2.8 mg/kg, 3.0 mg/kg, 3.2 mg/kg, 3.4 mg/kg, 3.6 mg/kg, 3.8 mg/kg, or 4.0 mg/kg. Pembrolizumab is administered by intravenous infusion at a dose of 2 mg/kg over 30 minutes once every three weeks. The adjunctive anti-CD40 antibody/pembrolizumab therapy is continued until disease progression or no longer tolerated by the patient.

In another exemplary embodiment, an anti-CD40 antibody is used adjunctive to pembrolizumab (Keytruda®) to treat non-small cell lung cancer. In some embodiments, the anti-CD40 antibody is any one of the humanized antibodies listed in TABLE 3. The anti-CD40 antibody is administered as an IT injection once every 7 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg. Pembrolizumab is administered by intravenous infusion at a dose of 2 mg/kg over 30 minutes once every three weeks. The adjunctive anti-CD40 antibody/pembrolizumab therapy is continued until disease progression or no longer tolerated by the patient.

In another exemplary embodiment, an anti-CD40 antibody is used adjunctive to pembrolizumab (Keytruda®) to treat non-small cell lung cancer. In some embodiments, the anti-CD40 antibody is any one of the humanized antibodies listed in TABLE 3. The anti-CD40 antibody is administered as an IT injection once every 14 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg. Pembrolizumab is administered by intravenous infusion at a dose of 2 mg/kg over 30 minutes once every three weeks. The adjunctive anti-CD40 antibody/pembrolizumab therapy is continued until disease progression or no longer tolerated by the patient.

In another exemplary embodiment, an anti-CD40 antibody is used adjunctive to pembrolizumab (Keytruda®) to treat non-small cell lung cancer. In some embodiments, the anti-CD40 antibody is any one of the humanized antibodies listed in TABLE 3. The anti-CD40 antibody is administered as an IT injection once every 28 days at 0.001 mg/kg, 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.03 mg/kg, 0.04 mg/kg, 0.05 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.8 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, or 2.0 mg/kg. Pembrolizumab is administered by intravenous infusion at a dose of 2 mg/kg over 30 minutes once every three weeks. The adjunctive anti-CD40 antibody/pembrolizumab therapy is continued until disease progression or no longer tolerated by the patient.

As will be appreciated by those of skill in the art, the recommended dosages for the various agents described above may need to be adjusted to optimize patient response and maximize therapeutic benefit.

8. EXAMPLES

The following Examples, which highlight certain features and properties of the exemplary embodiments of the anti-CD40 antibodies described herein are provided for purposes of illustration, and not limitation.

Example 1

Generation of Mouse Anti-Human CD40 Antibodies

Monoclonal antibodies were generated by immunizing Balb/C mice or SJL mice intraperitoneally with mouse 3T12 cells overexpressing human CD40. Spleens were harvested, and splenocytes were fused with the multiple myeloma cell line NS0. Hybridomas were selected using aminopterin. Selected hybridomas expressing anti-CD40 antibodies with agonistic activities were screened and subcloned to isolate individual clones.

To screen for antibodies with agonistic activity, a panel of functional assays was developed, including NFκB pathway stimulation, monocytes activation, dendritic cell (DC) activation and CD40 ligand (CD40L) competition. In these assays, anti-human CD40 G28-5 (mouse IgG1) (Biolegend) was included as positive control and an isotype matched mouse antibody (mIgG1) as negative control.

8.1.1. HEK293 blue CD40 NFκB Reporter Assay

HEK293 blue CD40 cell line (InVivogen) stably expressing human CD40 and a NFκB reporter gene were maintained in DMEM, 10% heat-inactivated fetal bovine serum (FBS), supplemented with 30 µg/mL Blasticidin and 100 µg/mL Zeocin. Activation of CD40 on the surface of HEK293 blue CD40 cells triggers a signaling cascade leading to the activation of NFκB and the subsequent secretion of embryonic alkaline phosphatase (SEAP). Incubation of hybridoma supernatants containing agonistic anti-CD40 with $2.5 \times 10^5$/mL of HEK293 blue CD40 cells stimulated production of SEAP which was measured by a colorimetic enzyme assay. The level of SEAP thus corresponded to the activity of anti-CD40 in the hybridoma supernatants.

8.1.2. Monocyte Activation Assay

The monocyte activity assay was performed using the monocytic cell line THP1-XBlue cells (InVivogen). This cell line stably expresses an NFκB and AP-1-inducible SEAP reporter gene and was maintained in RPMI 1640 with 10% heat-inactivated FBS and 200 µg/mL Zeocin. In the assay, $5 \times 10^5$/mL THP1-XBlue cells were first primed with 40 ng/mL IFNγ for 24 hours, and were subsequently incubated with testing samples for an additional 24 hours. Agonistic anti-CD40-induced SEAP activity was monitored by enzymatic assay.

8.1.3. Primary Dendritic Cell IL-12p70 Production Assay

Anti-CD40 clones were also screened for their ability to activate monocyte-derived dendritic cells (moDC). Activation was monitored by IL-12p70 production. Human peripheral blood mononuclear cells (PBMC) were first isolated on a Ficoll gradient. Briefly, whole blood from healthy human donors, diluted with an equal volume of PBS, was added to a Leucosep (Greiner Bio One) tube, containing Ficoll-Paque Plus below the frit (15 mL). The blood was then centrifuged at 1,000 g for 15 minutes without brake. PBMC were collected and washed once with PBS, centrifuged at 1,300 rpm for 5 minutes at room temperature, and washed once with RPMI 1640. Cells were re-suspended in culture medium (RPMI1640+10% heat-inactivated FBS). Monocytes were subsequently isolated from PBMC with an enrichment kit from StemCell and were cultured in StemSep serum free medium supplemented with 10 ng/mL GM-CSF and 20 ng/mL IL-4 at 37° C., 5% $CO_2$ for 6 days. Fresh GM-CSF and IL-4 were added to the culture at day 3 to help maintain DC differentiation. After 6 days in culture, monocyte-derived immature DC were subject to FACS analysis to verify immature DC phenotype: Lin−, CD80/CD86+, HLA-DR+, or CD11c+. Immature moDC were primed with IFNγ and stimulated with samples containing an anti-CD40 antibody for 48 hours in StemSep serum free medium supplemented with GM-CSF and IL-4. The culture supernatant was harvested and assayed for IL-12p70 production by a commercially available ELISA kit. The screening results and representative activity are summarized in Table 1-1.

Table 1-1 shows the range of agonistic anti-CD40 activity across isolated hybridomas. All of the new clones demonstrated monocyte activation comparable to literature CD40 antibody G28-5 (see, e.g., Bishop, G. A. Journal of Immunology 188, 4127-4129 (2012)). Clones AD166.4.4 and AD175.14.11 demonstrated monocyte activation but did not show dendritic cell activation. The remainder of the clones displayed monocyte activation comparable to G28-5, as well as enhanced dendritic cell activation as compared with G28-5.

TABLE 1-1

Summary of agonistic anti-CD40 clone screen

| Clone | Monocyte activation[1] (THP1-Xblue, $OD_{655}$) | moDC activation (IL-12p70, pg/mL) |
|---|---|---|
| AD163.7.2 | 0.13 | 905.3 |
| AD163.9.3 | 0.19 | 2216.3 |
| AD163.10.7 | 0.16 | 1318.8 |
| AD163.27.12 | 0.12 | 1514.5 |
| AD163.162.1 | 0.11 | 2155.5 |
| AD164.14.6 | 0.15 | 878 |
| AD164.76.3 | 0.16 | 769.8 |
| AD165.1.2 | 0.14 | 719.8 |
| AD166.4.4 | 0.24 | 0 |
| AD175.14.11 | 0.2 | 0 |
| G28-5 | 0.12 | 138.8 |
| muIgG1 | 0.06 | 0 |

[1]Monocyte activation is SEAP activity released from THP1-XBlue cells recorded at $OD_{655}$ The cDNA sequences encoding the heavy and light chain variable regions often monoclonal antibodies were cloned from hybridomas AD163.9.3, AD166.4.4, AD175.14.11, AD163.10.7, AD165.1.2, AD163.162.1, AD163.27.12, AD163.7.2, AD164.14.6, and AD164.76.3, respectively, using standard PCR techniques and were sequenced using standard DNA sequencing techniques. The full corresponding antibody amino acid sequences encoded by the DNA are shown in FIGS. 2A-2C.

Example 2

Epitope Classification of Mouse Anti-Human CD40 Antibodies

BIAcore analysis and an ELISA method were used to classify mouse anti-human CD40 agonistic antibodies based on their ability to compete with each other or CD40 ligand (CD40L) for binding to CD40.

BIAcore analysis was performed using a BIAcore T100 instrument at 12° C. A goat anti-mouse Fc antibody (Pierce, cat #31170) was first immobilized on CM5 sensor chip followed by capture of the first test antibody on the surface. After blocking by 50 µg/mL of mouse isotype antibody cocktail, the flow cells were injected with the soluble form of the extracellular domain of human CD40 (Creative BioMart, cat # CD402221H). Subsequently, the second test antibody or CD40L (PeproTech, cat #0308145) was injected to measure their binding to the complex of CD40 and the first test antibody. As shown in Table 2-1, the anti-CD40 antibodies of the disclosure were classified into three epitope groups. Epitope group 1 was exemplified by AD163.7.2 ("muAb8") and AD175.14.11 ("muAb3"), which blocked CD40L binding to CD40. Epitope group 2 was determined from clones AD163.162.1 ("muAb6") and AD163.27.12 ("muAb7"), which did not compete with CD40L or to antibodies in epitope group 1. The third epitope group was exemplified by clones AD163.9.3 ("muAb1"), AD166.4.4 ("muAb2"), and AD165.1.2 ("muAb5"), which did not compete with CD40L binding to CD40, but did compete with antibodies in epitope groups 1 and 2.

TABLE 2-1

Epitope classification by BIAcore analysis

| first antibody | second antibody | | | | | | | |
|---|---|---|---|---|---|---|---|---|
| | muAb6 | muAb1 | muAb2 | muAb7 | muAb5 | muAb8 | muAb3 | CD40L |
| muAb6 | — | X | X | X | X | Y | Y | Y |
| muAb1 | X | — | X | X | X | X | X | Y |
| muAb2 | X | X | — | X | X | X | X | Y |
| muAb7 | X | X | X | — | X | Y | Y | Y |
| muAb5 | X | X | X | X | — | X | X | Y |
| muAb8 | Y | X | X | Y | X | — | X | X |
| muAb3 | Y | X | X | Y | X | X | — | X |

X: second antibody unable to bind;
Y: simultaneous binding

An ELISA assay was developed to measure the effects of the anti-CD40 antibodies on the human CD4O-CD40L interaction. Briefly, a CD40-human Fc (huFc) fusion protein (Creative BioMart) was mixed with an anti-CD40 antibody or an isotype control antibody and added to 96-well plates coated with HA-tagged CD40L (R&D Systems). The binding of the CD40-huFc complex to the plate-bound CD40L was detected by HRP conjugated anti-human Fc antibody (Jackson ImmunoResearch). After development with TMB (3,3',5, 5'-tetramethylbenzidine) substrate, the plates were read at $OD_{450}$.

The effect of the anti-CD40 antibodies on CD40-CD40L interaction was determined by calculating the ratio of the $OD_{450}$ in the samples containing anti-CD40 antibodies to the $OD_{450}$ in the sample containing the isotype control antibody ("$OD_{450}$ ratio"). $OD_{450}$ ratios of ≤0.1 showed inhibition of human CD40L binding to human CD40. $OD_{450}$ ratios between 0.1 and 1 showed partial inhibition of CD40L binding to CD40. $OD_{450}$ ratios >1 showed enhanced binding of human CD40L to human CD40, thereby enhancing CD40 signaling.

The data are summarized in Table 2-2. Antibodies muAb8 and muAb3 blocked CD40 binding to CD40L exhibited a ratio less than 0.1. Antibodies muAb6 and muAb7 showed a ratio around 0.5, suggesting a modest effect on CD40-CD40L interaction. Antibodies muAb1, muAb2, muAb4, muAb5, muAb9, and muAb10 exhibited an $OD_{450}$ ratio of about 1 or greater than 1, indicating either no effect or an effect that promoted CD40 binding to CD40L.

TABLE 2-2

Competition with CD40 for CD40L Binding

| Antibody | $OD_{450}$ with anti-CD40 antibody | $OD_{450}$ Ratio |
|---|---|---|
| muAb8 | 0.066 | 0.08 |
| muAb3 | 0.068 | 0.09 |
| muAb7 | 0.328 | 0.41 |
| muAb6 | 0.455 | 0.57 |
| muAb1 | 1.779 | 2.22 |
| muAb4 | 1.343 | 1.68 |
| muAb9 | 1.883 | 2.35 |
| muAb10 | 2.107 | 2.63 |
| muAb5 | 0.989 | 1.24 |
| muAb2 | 1.025 | 1.28 |

Example 3

Humanization of Mouse Anti-Human CD40 Antibodies

Humanization of the antibody V region was carried out as outlined by Queen, C. et al. (Proc. Natl. Acad. Sci. USA, 1989; 86:10029-10033). The canonical structures of the CDRs were determined according to Huang et al. (Methods, 2005; 36:35-42). Human variable germline sequences with the same or most similar CDR canonical structures were identified, and appropriate human $V_H$, $V_L$, and J segment sequences were selected to provide the frameworks for the anti-CD40 variable region. At framework positions in which the computer model suggested significant contact with the CDRs, the amino acids from the murine anti-CD40 V regions were substituted for the original human framework amino acids (back-mutations). The constant regions of human $IgG_1$ with natural variants D356E and L358M in the heavy chain, and a kappa light chain were used unless otherwise specified. Full amino acid sequences of the $V_H$ and $V_L$ regions of the humanized antibodies are shown in FIGS. 2D-2G.

Anti-CD40 clone AD163.162.1 ("muAb6") was humanized according to the method described above. The humanized versions of muAb6 were huAb6-1, huAb6-2 and huAb6-3. Antibody huAb6-1 carried $V_H$ (SEQ ID NO: 110) framework back-mutations: M48I, V67A, I69L, and A71V. Antibody huAb6-2 carried $V_H$ (SEQ ID NO: 111) framework back-mutations M48I and A71V. Antibody huAb6-3 carried $V_H$ (SEQ ID NO: 112) framework back-mutations M48I and A71V, as well as $V_H$ CDR germlining changes N60A, K64Q and D65G to increase identity to human germline sequence. Antibodies huAb6-1, huAb6-2 and huAb6-3 carried $V_L$ (SEQ ID NO: 161) framework back-mutations: A43S, L46R, L47W and F71Y.

The humanized versions of anti-CD40 clone AD163.7.2 ("muAb8") were huAb8-1, huAb8-2 and huAb8-3 (FIGS. 2D-2E). Antibody huAb8-1 carried $V_H$ (SEQ ID NO: 113) framework back-mutations: M48I, V67A, I69L, A71V, K73R, Y91F, and R94S. Antibody huAb8-2 carried $V_H$ (SEQ ID NO: 114) framework back-mutations: M48I, V67A, I69L, A71V, K73R, Y91F, and R94S; as well as $V_H$ CDR C59S mutation. Antibody huAb8-3 carried $V_H$ (SEQ ID NO: 115) framework back-mutations: M48I, A71V and R94S. Antibodies huAb8-1, huAb8-2 and huAb8-3 all carried $V_L$ (SEQ ID NO: 162) framework back-mutations: A43S, and Y87F.

Anti-CD40 clone AD164.14.6 ("muAb9") was humanized to provide huAb9-1, huAb9-2, huAb9-3, huAb9-4, huAb9-5 and huAb9-6. Antibodies huAb9-1 and huAb9-4 displayed $V_H$ (SEQ ID NO: 116) framework back-mutations: I48M, V67I and V71R. Antibodies huAb9-2 and huAb9-5 carried $V_H$ (SEQ ID NO: 117) framework back-mutations: I48M and V71R. Antibodies huAb9-3 and huAb9-6 carried $V_H$ (SEQ ID NO: 118) framework back-mutations: I48M and V71R, as well as additional two CDR germline changes T30S and N65S to improve identity to human germline sequence. Antibodies huAb9-1, huAb9-2 and huAb9-3 carried $V_L$ (SEQ ID NO: 163) framework back-mutations: I2A, Y36F and Y87F. Antibodies huAb9-4, huAb9-5 and huAb9-6 carried $V_L$ (SEQ ID NO: 164) framework back-mutation I2A. Clone AD164.14.6 was further modified to remove a signal peptide cleavage site found at the second position of the light chain, by reverting the framework back-mutation I2A of the $V_L$. Antibodies huAb9 A2I and huAb9 A2V carried $V_H$ (SEQ ID NO:117) and $V_L$ containing framework revert mutations A2I (SEQ ID NO:170) and A2V (SEQ ID NO:171), respectively, prevented the formation of an undesired cleavage product.

Humanized antibodies in the present Example were generated with a human IgG1 heavy chain constant region and kappa light chain constant region. The C-terminal lysine may be partially cleaved by post-translational processing after protein expression of the human IgG1 heavy chain. Accordingly, huAb9-5 had a heavy chain according to SEQ ID NOS:130 or 131 and a light chain according to SEQ ID NO:140. Antibody huAb9-5 also was produced with V273E and V273Y amino acid mutations in the heavy chain constant region, corresponding to a heavy chain according to SEQ ID NOS:132 or 133 and SEQ ID NOS:134 or 135, respectively, and a light chain according to SEQ ID NO:140. Antibodies huAb9 A2I and huAb9 A2V were generated with a human IgG1 V273E heavy chain constant region. Accordingly, huAb9 A2I had a heavy chain according to SEQ ID NOS:132 or 133 and a light chain according to SEQ ID NO:141. Analogously, huAb9 A2V had a heavy chain according to SEQ ID NOS:132 or 133 and a light chain according to SEQ ID NO:142.

Example 4

Characterization of the Humanized Anti-Human CD40 Antibodies

To ensure the humanized anti-CD40 antibodies retained the agonistic and other desired properties of the parental murine antibodies, a panel of characterization assays was performed to determine NFκB activation, CD40 binding kinetics, species cross-reactivity and epitope classes of the humanized antibodies of the disclosure.

8.4.1. NFκB Activation

NFκB activation by humanized anti-CD40 antibody of the invention was evaluated in HEK293 blue CD40 NFκB reporter cells. The activation was represented as SEAP (secreted embryonic alkaline phosphatase) reporter gene activity measured at $OD_{655}$. The maximal $OD_{655}$ measured and the concentration for half-maximal activation (EGO are summarized in Table 4-1.

TABLE 4-1

NFκB activation in HEK293 blue CD40 NFκB reporter cells

| Humanized antibody | $EC_{50}$ (µg/mL) | Maximal activation ($OD_{655}$) |
| --- | --- | --- |
| huAb6-1 | 1.09 | 0.26 |
| huAb6-2 | 1.21 | 0.20 |
| huAb6-3 | 4.31 | 0.32 |
| huAb8-1 | 0.14 | 0.45 |
| huAb8-3 | 0.07 | 0.46 |
| huAb9-1 | 0.19 | 0.26 |
| huAb9-2 | 0.29 | 0.27 |
| huAb9-3 | 0.18 | 0.27 |
| huAb9-4 | 5.55 | 0.61 |
| huAb9-5 | 1.13 | 0.67 |
| huAb9-6 | 5.95 | 0.54 |

8.4.2. CD40 Binding Kinetics and Species Cross-Reactivity

The binding affinities of the disclosed humanized anti-CD40 antibodies were analyzed by both BIAcore and flow cytometry analysis.

CD40 binding kinetics was analyzed by BIAcore assay with a BIAcore T200 instrument. Briefly, a goat anti-mouse Fc antibody (Pierce, cat #31170) or goat anti-human Fc (Pierce, cat #31125) was immobilized on a CM5 sensor chip, followed by capture of the anti-CD40 antibodies on the test surface. Subsequently, the soluble form of the extracellular domain of human CD40 (Creative BioMart, cat # CD402221H) or cynomolgus (cyno) CD40 (Creative BioMart, cat # CD40-8824C) was injected, and the binding and dissociation were measured.

Surface plasmon resonance data indicated that humanized huAb8-1, huAb9-5, huAb9 A2I, and huAb9 A2V antibodies retained similar binding affinities ($K_D$) as that of their parental clones AD163.7.2 ("muAb8") or clone AD164.14.6 ("muAb9"), and showed similar binding to human or cynomolgus CD40 (Table 4-2).

TABLE 4-2

| | Affinity measured by BIAcore* | | | | | |
| --- | --- | --- | --- | --- | --- | --- |
| | Human CD40 | | | Cynomolgus CD40 | | |
| Antibody | $k_a$ (1/Ms) | $k_d$ (1/s) | $K_D$ (M) | $k_a$ (1/Ms) | $k_d$ (1/s) | $K_D$ (M) |
| muAb6 | 7.6E+04 | 4.8E−03 | 6.3E−08 | Not determined | | |
| muAb7 | 7.5E+04 | 4.8E−03 | 6.4E−08 | Not determined | | |
| muAb8 | 1.0E+06 | 4.2E−03 | 4.1E−09 | Not determined | | |
| muAb3 | 6.9E+04 | 1.2E−02 | 1.7E−07 | Not determined | | |
| muAb1 | 4.7E+05 | 1.6E−02 | 3.5E−08 | Not determined | | |
| muAb2 | 2.8E+06 | 9.6E−03 | 3.5E−09 | Not determined | | |
| muAb4 | 2.3E+06 | 1.7E−01 | 7.6E−08 | Not determined | | |
| muAb5 | 2.3E+06 | 2.0E−03 | 8.8E−10 | Not determined | | |

TABLE 4-2-continued

| | Affinity measured by BIAcore* | | | | | |
|---|---|---|---|---|---|---|
| | Human CD40 | | | Cynomolgus CD40 | | |
| Antibody | $k_a$ (1/Ms) | $k_d$ (1/s) | $K_D$ (M) | $k_a$ (1/Ms) | $k_d$ (1/s) | $K_D$ (M) |
| muAb10 | 2.6E+06 | 3.4E−02 | 1.3E−08 | Not determined | | |
| muAb9 | 2.8E+06 | 5.2E−02 | 1.9E−08 | Not determined | | |
| huAb8-1 | 7.7E+05 | 2.3E−03 | 3.0E−09 | 1.0E+06 | 7.1E−03 | 7.1E−09 |
| huAb9-5 | 1.7E+06 | 2.6E−02 | 1.5E−08 | 1.8E+06 | 2.4E−02 | 1.3E−08 |
| huAb9 A2I | 1.3E+06 | 2.2E−01 | 1.7E−07 | 1.7E+06 | 2.5E−01 | 1.5E−07 |
| huAb9 A2V | 1.5E+06 | 2.6E−01 | 1.7E−07 | 1.9E+06 | 2.7E−01 | 1.4E−07 |

*Numbers refer to scientific notation, e.g., 3.0E−09 = $3.0 \times 10^{-9}$.

The humanized anti-CD40 antibodies were also evaluated for binding to cell-surface CD40 on HEK293 cells stably transfected with human or cynomolgus CD40, as well as B cells derived from cynomolgus or human PBMC. Humanized anti-CD40 antibodies were incubated with HEK293 transfectants for 15 minutes on ice, and the binding was detected with a fluorescence-conjugated anti-human secondary antibody (Jackson ImmunoResearch). FACS analysis of the cells confirmed that the humanized antibodies bound to human and cynomolgus CD40 stable cell lines. In contrast, no binding was observed in similar experiments performed with mouse, rat or dog CD40.

The anti-CD40 antibodies were also assessed for their ability to bind to primary human and cynomolgus CD40-expressing cells. PBMCs isolated from human or cynomolgus blood were incubated with anti-CD40 antibodies conjugated to the fluorescence dye CF640R. After FACS analysis, the data were analyzed by FlowJo (FlowJo, LLC) software. These results demonstrated that the humanized antibodies bound to primary CD40-positive cells derived from both human and cynomolgus PBMC.

8.4.3. Epitope Classification

Flow cytometry analysis and an ELISA method were used to classify humanized agonistic anti-CD40 antibodies based on their ability to compete with each other or CD40 ligand (CD40L) for binding to CD40.

A flow cytometry analysis was developed to assess whether an antibody competes for binding human CD40 with another antibody. In this assay, CP-870,893, prepared from a fully human IgG$_2$ anti-human CD40 antibody clone 21.4.1 (see, Gladue, R P. et al., Cancer Immunol. Immunother. 2011; 60:1009-17 and U.S. Pat. No. 7,618,633), was used as the reference antibody. The heavy and light chains, respectively, of CP-870,893 were:

(SEQ ID NO: 181)
QVQLVQSGAEVKKPGASVKVSCKASGYTFTGYYMHWVRQAPGQGLEWMGW

INPDSGGTNYAQKFQGRVTMTRDTSISTAYMELNRLRSDDTAVYYCARDQ

PLGYCTNGVCSYFDYWGQGTLVTVSSASTKGPSVFPLAPCSRSTSESTAA

LGCLVKDYFPEPVTVSWNSGALTSGVHTFPAVLQSSGLYSLSSVVTVPSS

NFGTQTYTCNVDHKPSNTKVDKTVERKCCVECPPCPAPPVAGPSVFLFPP

KPKDTLMISRTPEVTCVVVDVSHEDPEVQFNWYVDGVEVHNAKTKPREEQ

FNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTP

PMLDSDGSFFLYSKLTVDKSRWQQGNVFSCSVMHEALHNHYTQKSLSLSP

GK,
and (SEQ ID NO: 182)
DIQMTQSPSSVSASVGDRVTITCRASQGIYSWLAWYQQKPGKAPNLLIYT

ASTLQSGVPSRFSGSGSGTDFTLTISSLQPEDFATYYCQQANIFPLTFGG

GTKVEIKRTVAAPSVFIFPPSDEQLKSGTASVVCLLNNFYPREAKVQWKV

DNALQSGNSQESVTEQDSKDSTYSLSSTLTLSKADYEKFIKVYACEVTHQ

GLSSPVTKSFNRGEC.

All anti-CD40 human or humanized antibodies, including huAb6-1, huAb8-1, huAb9 A2I, and CP-870,893, were labeled with Alexa Fluor (AF)-488. Each fluorescence-labeled antibody with fixed concentration at 1 µg/mL was separately mixed with increasing amount of other unlabeled anti-CD40 antibodies ranging from 0.5 ng/mL up to 50 µg/mL, and incubated with HEK293 cells stably expressing human CD40. The binding of fluorescence-labeled antibody was then monitored by flow cytometry.

The competitive antibodies identified by dose-dependent reduction of mean fluorescence intensity (MFI) and non-competitive antibodies identified by constant MFI were summarized in Table 4-3. While huAb6-1 did not compete for binding human CD40 with huAb8-1, both huAb9 A2I and the CP-870,893 competed with huAb6-1 and huAb8-1. Additionally, huAb9 A2I and CP-870,893 competed with each other.

TABLE 4-3

| Epitope classification by flow cytometry analysis | | | | |
|---|---|---|---|---|
| | second antibody | | | |
| first antibody | huAb6-1 | huAb8-1 | huAb9 A2I | CP-870,893 |
| huAb6-1 | — | Y | X | X |
| huAb8-1 | Y | — | X | X |
| huAb9 A2I | X | X | — | X |
| CP-870,893 | X | X | X | — |

X: mutually competitive;
Y: mutually non-competitive

Epitope classification of the humanized antibodies of the invention was also confirmed by an ELISA assay measuring the binding of anti-CD40 antibody and CD40 complex to plate-bound CD40L as described in Example 2. In this assay, CP-870,893 as prepared above was used as a reference anti-CD40 antibody. Increasing amounts of anti-CD40 antibodies or human IgG$_1$ (huIgG$_1$) control antibody were incubated with 1 µg/mL of CD40-huFc fusion protein, and added to a plate coated with CD40L. As shown in FIG. 3, humanized antibodies huAb8-1 and huAb8-3 blocked interaction of CD40 and CD40L (upper left); huAb6-1 and huAb6-2 showed minimal effect on CD4O-CD40L interaction (upper right); and huAb9-5 and huAb9-6 promoted CD40 binding to CD40L (lower left). Humanized antibody huAb9 A2I also promoted CD40 binding to CD40L as compared to CP-870,893, which showed minimal effect on CD40-CD40L interaction (lower right).

Figure 4:
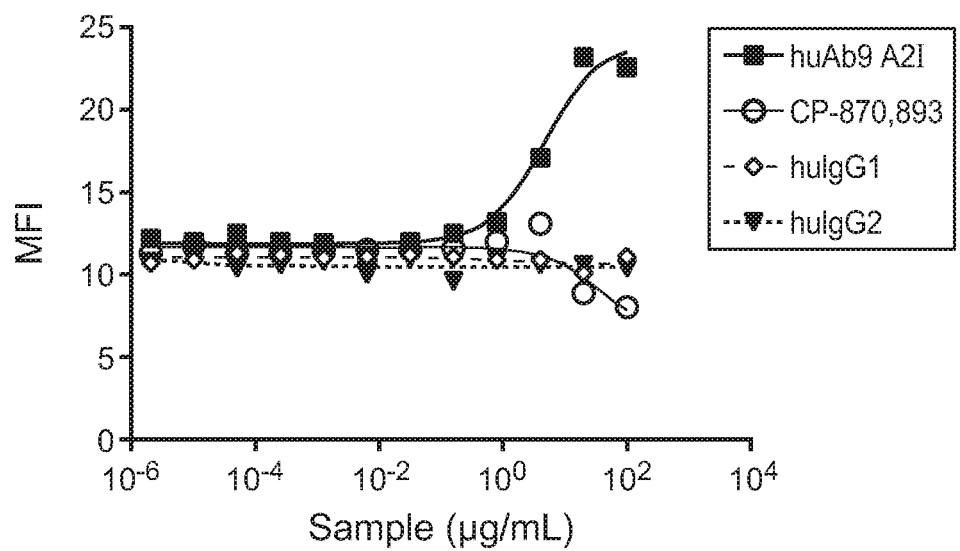

The results were consistent with those obtained in a flow cytometry based assay with cells expressing CD40L (FIG. 4). CD40L+ Jurkat cells were incubated with fluorochrome Alexa Fluor 488-conjugated soluble human CD40 protein at a constant concentration of 1 µg/mL. The binding of fluorochrome-conjugated CD40 to Jurkat cell surface CD40L was measured by flow cytometry analysis in the presence of humanized antibody huAb9 A2I and reference anti-CD40 antibody CP-870,893. Enhanced fluorescence intensity was detected upon increased amount of huAb9 A2I in the sample, but not with reference antibody CP-870,893. These results suggested that huAb9 A2I promoted CD40 binding to CD40L+ Jurkat cells while the reference CP-870,893 did not.

Figure 5A:
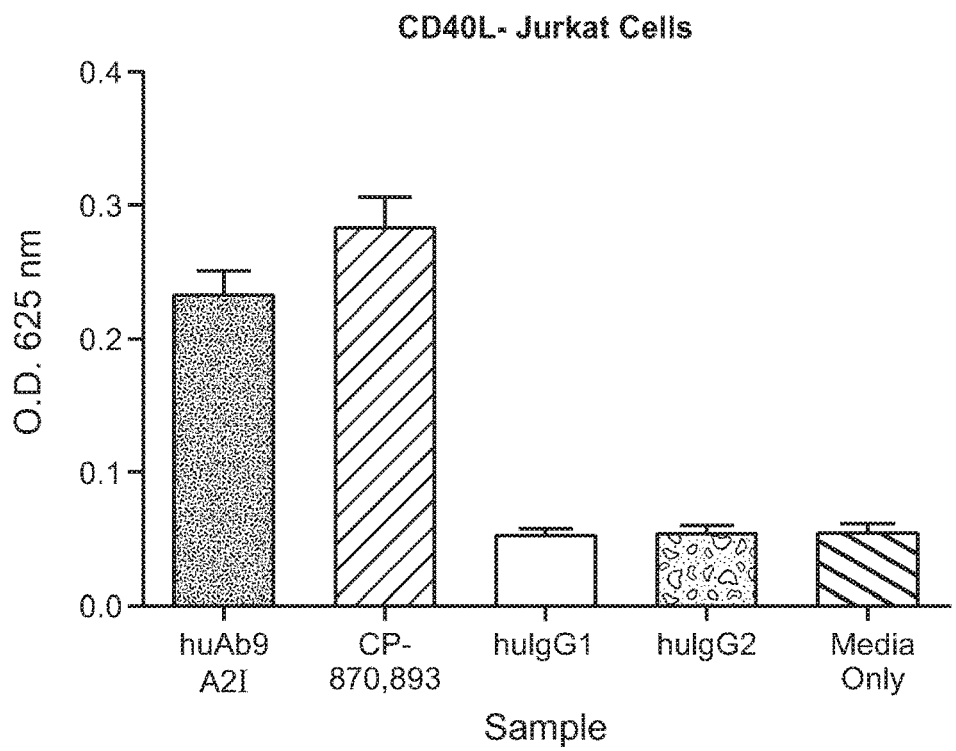
Figure 5B:
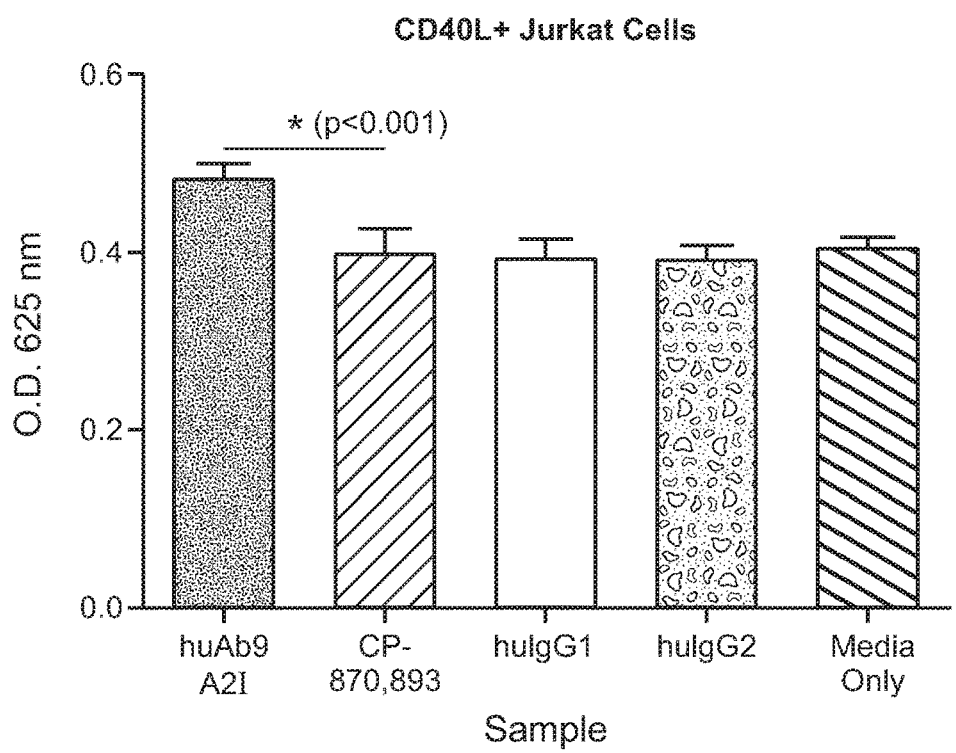

The functional impact of huAb9 A2I on CD40 signaling driven by CD40L was also determined in an assay comprising both CD40 and CD40L expressing cells. CD40-expressing cells (HEK293 blue CD40 NFκB reporter cells described in Section 8.1.1) were mixed with CD40L– or CD40L+ Jurkat cells at the ratio of 1:1, and incubated with either huAb9 A2I, CP-870,893 or control antibody at 3 µg/mL. The CD40 signaling was measured by SEAP reporter activity through a colorimetric assay as described in Section 8.4.1. When CD40 reporter cells were co-cultured with CD40L– Jurkat cells (FIG. 5A), CD40 signaling was significantly enhanced only after addition of either huAb9 A2I or CP-870,893, but not with treatment of control antibody or with no addition. Although both antibodies activated CD40, huAb9 A2I was not significantly more potent than CP-870,893 in stimulating CD40 under these conditions. When CD40 reporter cells were co-cultured with CD40L+ Jurkat cells (FIG. 5B), cell surface CD40L activated CD40 as indicated by SEAP reporter activity. Treatment with CP-870,893 did not further enhance CD40 activity signaling with SEAP reporter activity similar to the control huIgG1 or huIgG2 isotype, or no antibody (media only) treatment. In contrast, treatment with huAb9 A2I further increased CD40 signaling with reporter activity significantly greater than CP-870,893 and the control treatments (p<0.001).

These data indicated that when cell surface CD40 was activated by a saturated amount of cell surface CD40L, huAb9 A2I further enhanced CD40 activation by effecting greater downstream NFκB signaling as compared with an equivalent amount of known anti-CD40 antibody CP-870,893.

Example 5

Fc Region Variants of Anti-CD40 Antibodies

Greater agonistic activity of CD40 can be achieved through modifying the Fc region to enhance FcγRIIB binding (Li and Ravetch, Science, 2011; 333:1030-1034; and White, et al., J. Immunol, 2011; 187:1754-1763). Two mutations, V273E and V273Y, at position 273 in the human IgG1 constant region were introduced into the humanized anti-CD40 antibodies huAb6-1, huAb8-1, huAb9-5, and huAb9 A2I. The impact of the Fc mutations on binding to Fcγ receptors was monitored by FACS analysis and by antibody-dependent cell-mediated cytotoxicity (ADCC). The agonistic activities of humanized anti-CD40 with Fc modification were monitored through activation of NF-κB reporter, B cells, monocyte-derived DC and T cells.

8.5.1. Fcγ Receptor Binding and ADCC Function

Figure 6A:
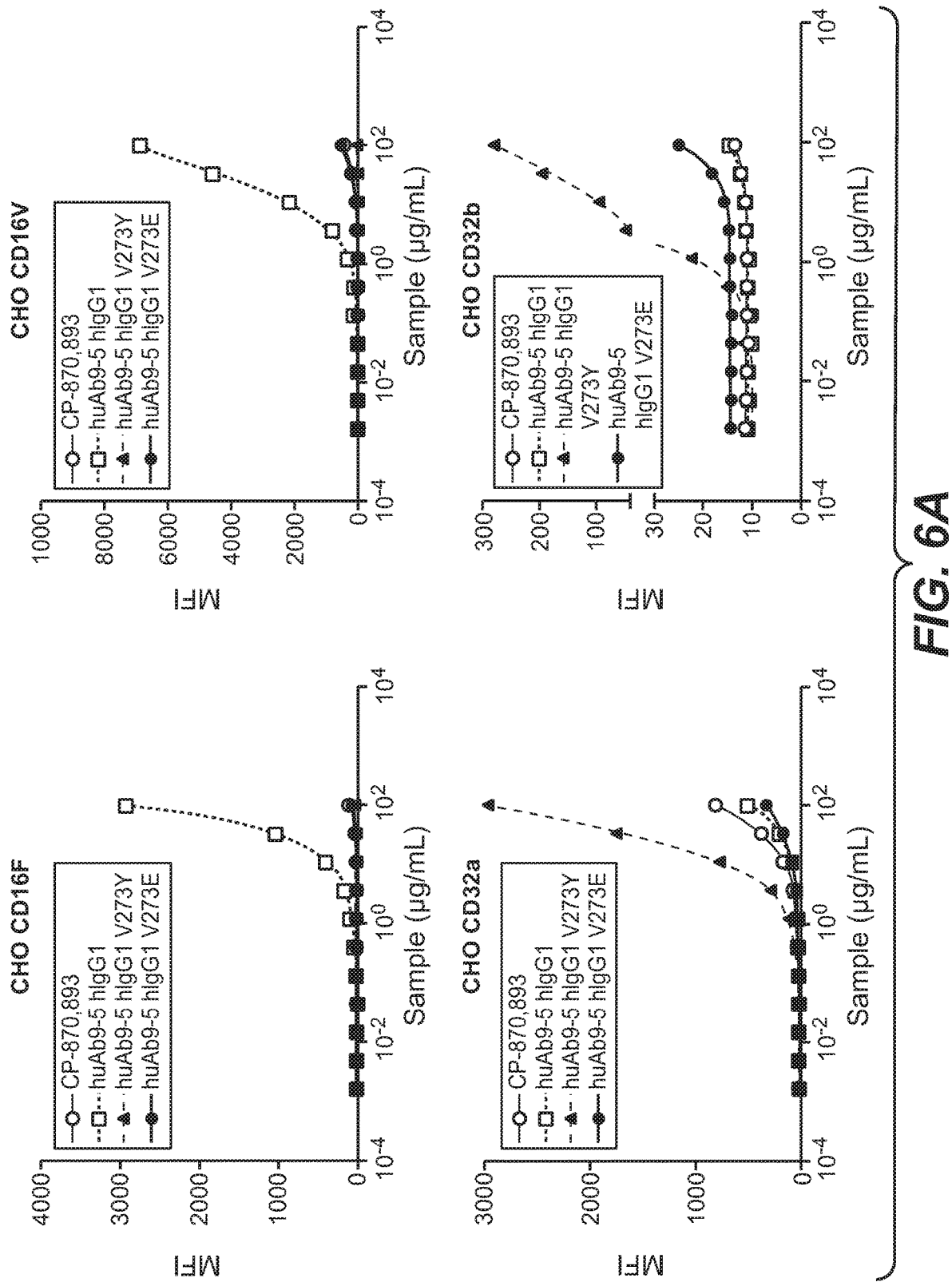
Figure 6B:
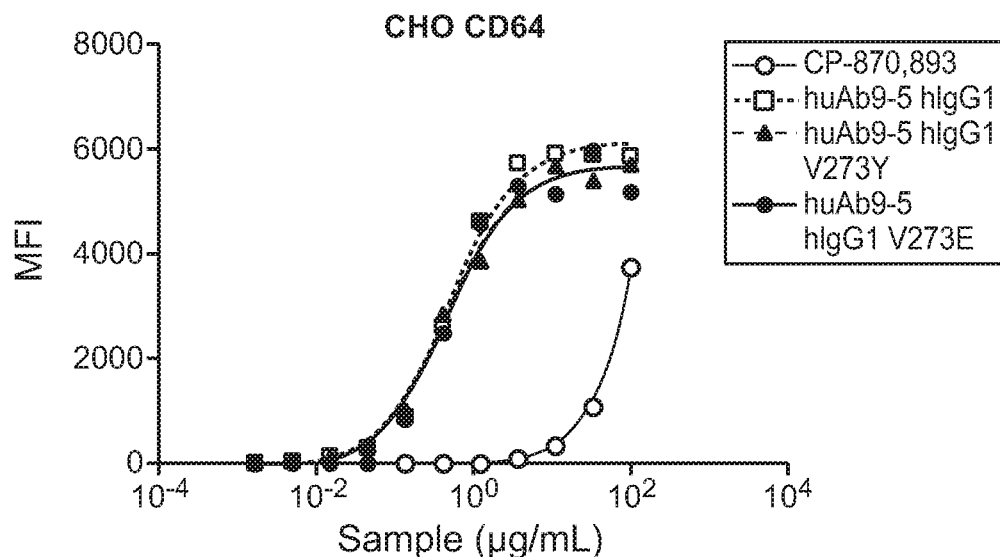

Increasing amounts of anti-CD40 human IgG$_1$ antibodies and their Fc variants were incubated with CHO cells stably expressing different human Fcγ receptors, including FcγRI (CD64), FcγRIIA (CD32a), FcγRIIB (CD32b), and FcγRIIIA (CD16) with either F or V polymorphism. The binding was detected with a fluorescence-conjugated anti-human F(ab')$_2$ specific secondary antibody (Jackson ImmunoResearch). The mutations V273E or V273Y reduced binding to FcγRIIIA (CD16F or V) while maintaining FcγRI (CD64) binding, and enhancing FcγRIIA (CD32a) or FcγRIIB (CD32b) binding (FIGS. 6A-6B).

Figure 7:
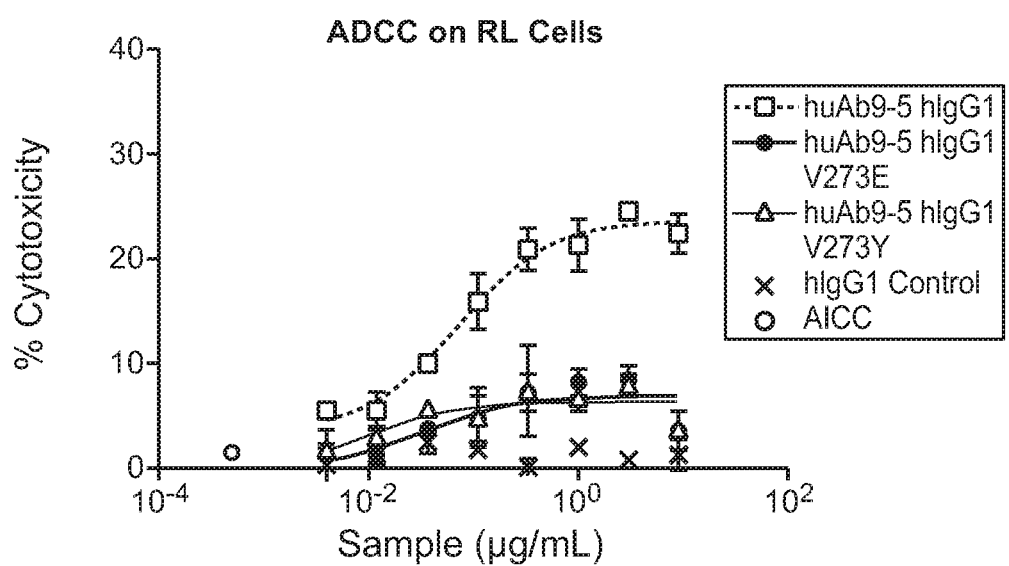

The ADCC of the Fc variants of the humanized anti-CD40 antibodies was measured using a standard protocol (Law et al., 2005, Cancer Res. 65:8331-8). In an illustrative example, ADCC was reduced with constant region variants V273E or V273Y as compared with wild type IgG$_1$ for antibody huAb9-5 in RL cells (FIG. 7).

8.5.2. Enhanced Agonistic Activity Upon FcγR Binding

To evaluate the impact of Fcγ receptor binding on agonistic activity of anti-CD40, huAb9 A2I with huIgG$_1$ V273E mutation was used to treat HEK293 blue CD40 NFκB reporter cells co-cultured with CHO cells stably expressing different human Fcγ receptors, and NKκB activity was monitored. As shown in Table 5-1, agonistic activity of CP-870,893 in stimulating NKκB activation was independent of Fcγ receptor binding, while agonistic activity of huAb9 A2I was found to be dependent on Fcγ receptor binding. The potency of huAb9 A2I was ten-fold higher in stimulating NKκB activity when reporter cells were co-cultured with CHO cells expressing CD32a, CD32b or CD64 than when co-cultured with CHO cells without Fcγ receptor expression, or expressing CD16V or CD16F.

TABLE 5-1

| | NFκB activity (EC$_{50}$, nM) | |
|---|---|---|
| CHO (FcγR) | huAb9 A2I (huIgG$_1$ V273E) | CP-870,893 (huIgG$_2$) |
| FcγR negative | 0.72 | 0.03 |
| CD16F | 0.39 | 0.03 |
| CD16V | 0.30 | 0.02 |
| CD32a | 0.08 | 0.02 |
| CD32b | 0.07 | 0.02 |
| CD64 | 0.01 | 0.02 |

8.5.3. Fc Variants on B Cell Proliferation

Figure 8:
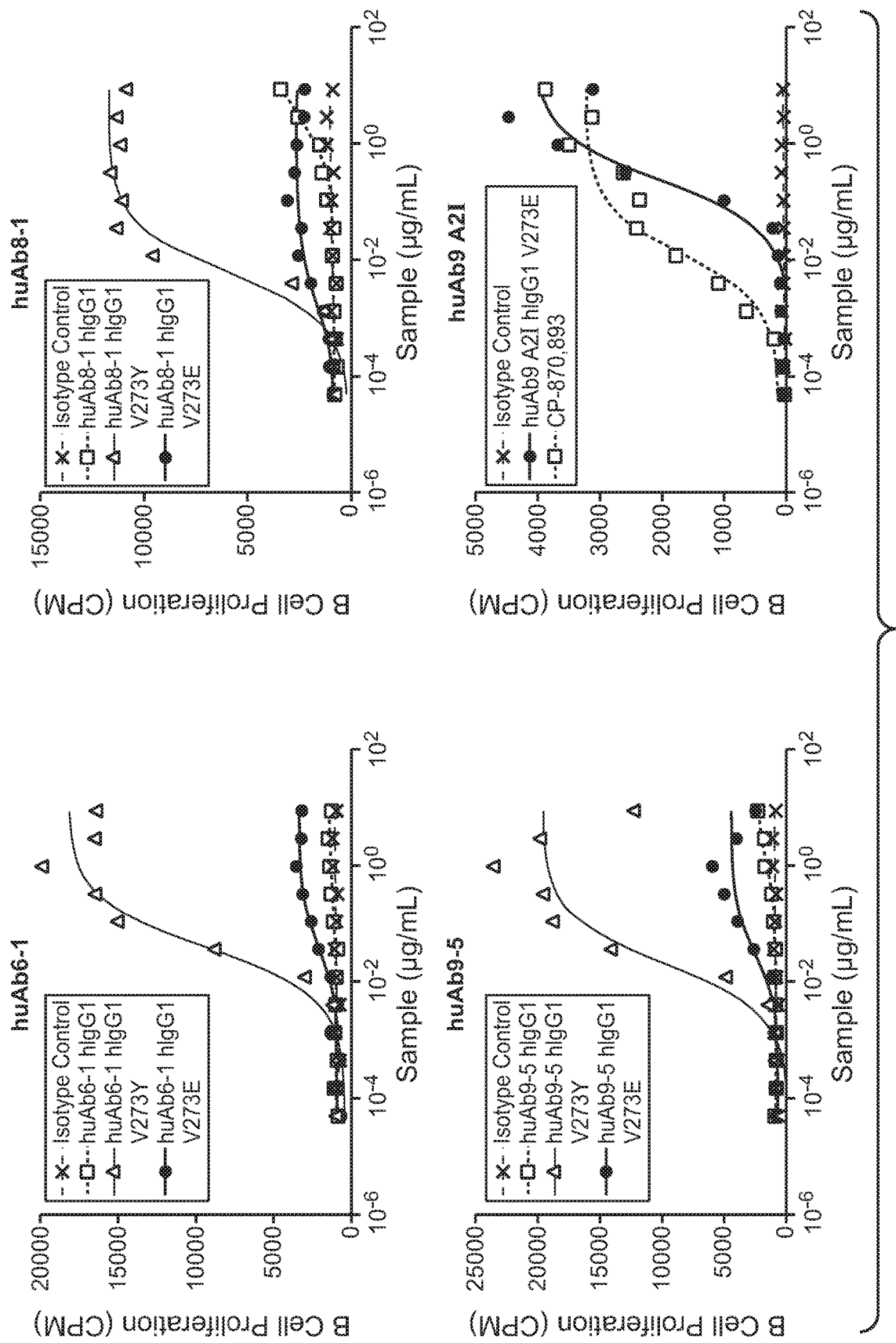

The impact of Fc V273E or V273Y mutation on agonistic activity of anti-CD40 was also evaluated with B cell proliferation assay. In this assay, human B cells were enriched by B cell enrichment kit (StemCell Technologies) through negative selection. The purified B cells were seeded into 96 well plates at 5×10$^5$/ml, 200 µL per well in AIM-V serum free medium (GIBCO). Serially diluted anti-CD40 antibodies were added and cultured with B cells for 6 days. In the last 16 hours of culture, 1 µCi of H$^3$TdR were added to each well of the culture and B cell proliferation was determined by H$^3$TdR incorporation. The radioactivity associated with H³TdR incorporation was recorded by a scintillation counter as count per minute (CPM). Compared to the corresponding human IgG1 wild-type antibodies, the anti-CD40 (huAb6-1, huAb8-1 and huAb9-5) human IgG1 Fc variants V273E and V273Y showed enhanced B cell activation (FIG. 8). However, when compared to CP-870,893, huAb9 A2I (human IgG$_1$ V273E) showed about ten-fold lower potency in stimulating B cell proliferation (lower right graph).

8.5.4. Fc Variants on DC IL-12p70 Production

Figure 9:
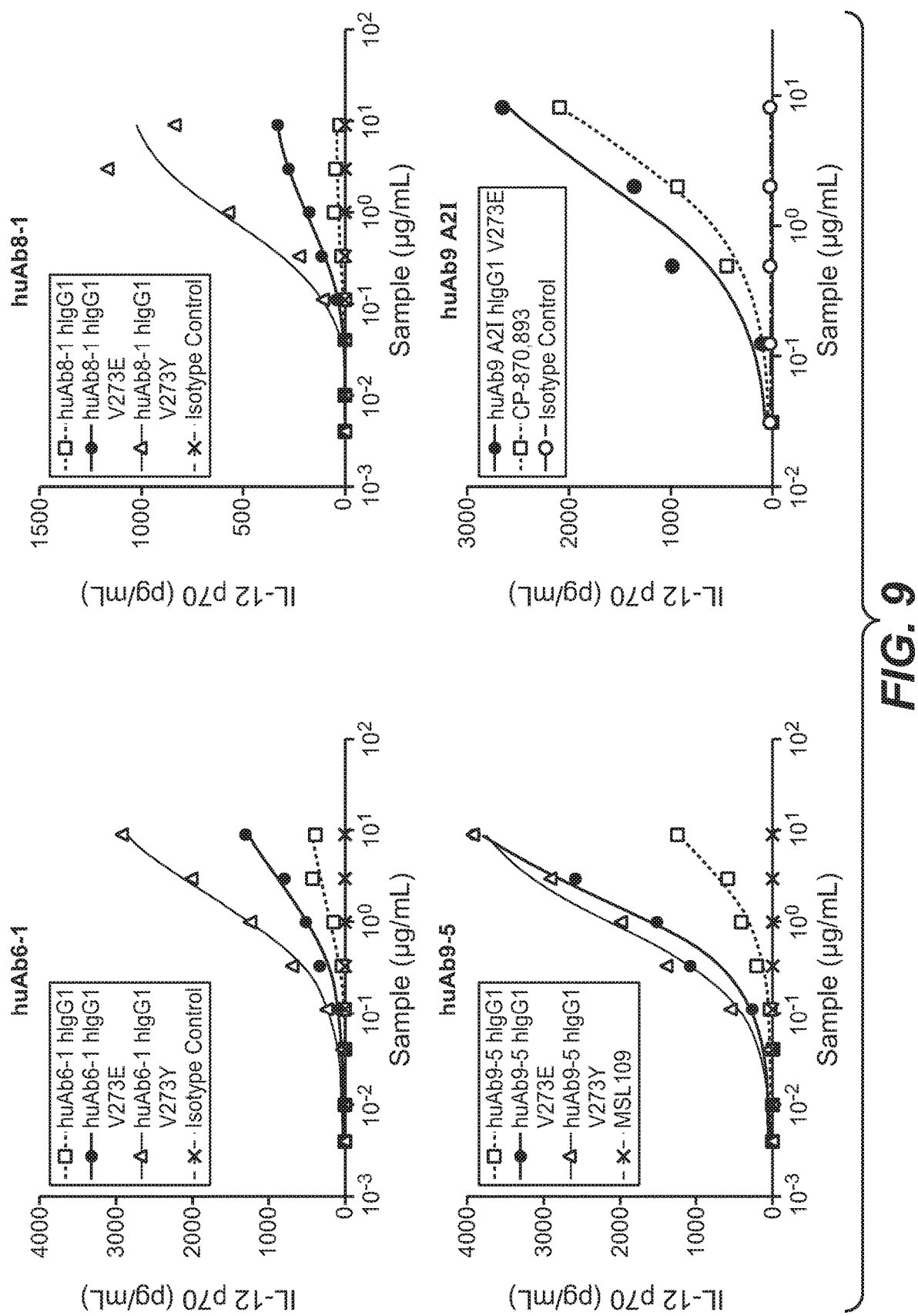

The impact of Fc V273E or V273Y mutation on agonistic activity of anti-CD40 was further evaluated with DC activation assay using IL-12p70 as read-out. In this assay, immature DCs were first derived from monocytes purified from human PBMC and treated with IL4 and GM-CSF. DC maturation and IL-12p70 production were induced by anti-CD40 after priming with IFNγ. The V273E or V273Y Fc mutated versions enhanced potency on DC activation by enhancing IL-12p70 production. As illustrated in FIG. 9, huAb6-1 (upper left), huAb8-1 (upper right), and huAb9-5 (lower left) with huIgG$_1$ Fc variants V273E or V273Y showed increased IL-12p70 production as compared with their corresponding antibodies having wild type huIgG$_1$. For huAb6-1 and huAb8-1, the variant with huIgG$_1$ V273Y mutation was more effective at enhancing in vitro IL-12p70 production than the one with the V273E mutation. For huAb9-5, variants with huIgG$_1$ V273E or V273Y showed similar potency. In the case of huAb9 A2I (lower right graph), the variant with huIgG$_1$ V273E mutation demonstrated similar potency as CP-870,893 in stimulating DC to produce IL-12p70.

8.5.5. Fc Variants on T Cell Activation in Allogeneic DC and T Cell Co-Culture

To demonstrate anti-CD40 could drive T cell activation through stimulating antigen presenting cells such as DC, anti-CD40 Fc variants were tested in allogeneic DC and T cell co-culture. In this assay, dendritic cells (5×10³) were first derived from monocytes using the method described above, then mixed with 1×10⁵ T cells purified from a different donor. Various amounts of anti-CD40 antibody huAb6-1, huAb8-1, or huAb9-5 with either the wild-type human IgG$_1$ constant region or their Fc variants V273Y were added to the DC and T cell co-culture. After 4 days incubation, supernatants were collected and IFN-γ was measured by ELISA.

Figure 10:
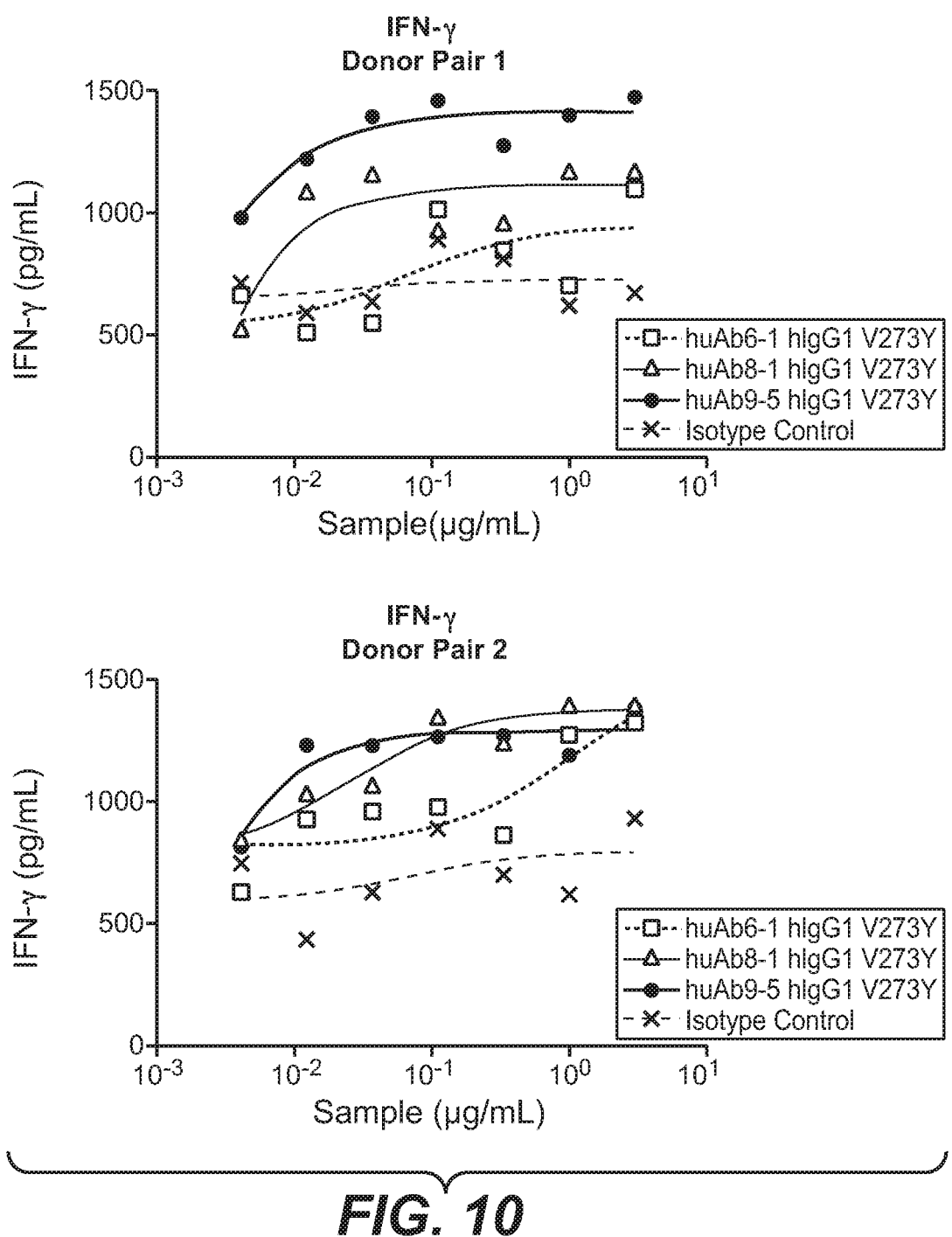
FIG. 10 shows the effect of a V273Y variant of huAb6-1, huAb8-1, or huAb9-5 on DC and T-cell co-cultures as measured by interferon-gamma (IFN-γ) production in pg/mL.

FIG. 10 illustrates exemplary antibodies that showed enhanced IFN-γ production in the co-culture with cells from two different donor-pairs. In each instance, the V273Y variants of huAb6-1, huAb8-1, and huAb9-5 demonstrated T cell activation as evidenced by significant increases in IFN-γ as compared with an isotype control huIgG$_1$ antibody.

Example 6

In Vivo Antitumor Activity Of Anti-CD40 Antibodies

The humanized anti-CD40 antibodies huAb6-1, huAb9-5, and huAb9 A2I with wild-type human IgG$_1$ or Fc variants were assessed for their ability to inhibit tumor growth in NSG mice bearing the prostate PC3 tumors in the presence of human immune cells.

Figure 11:
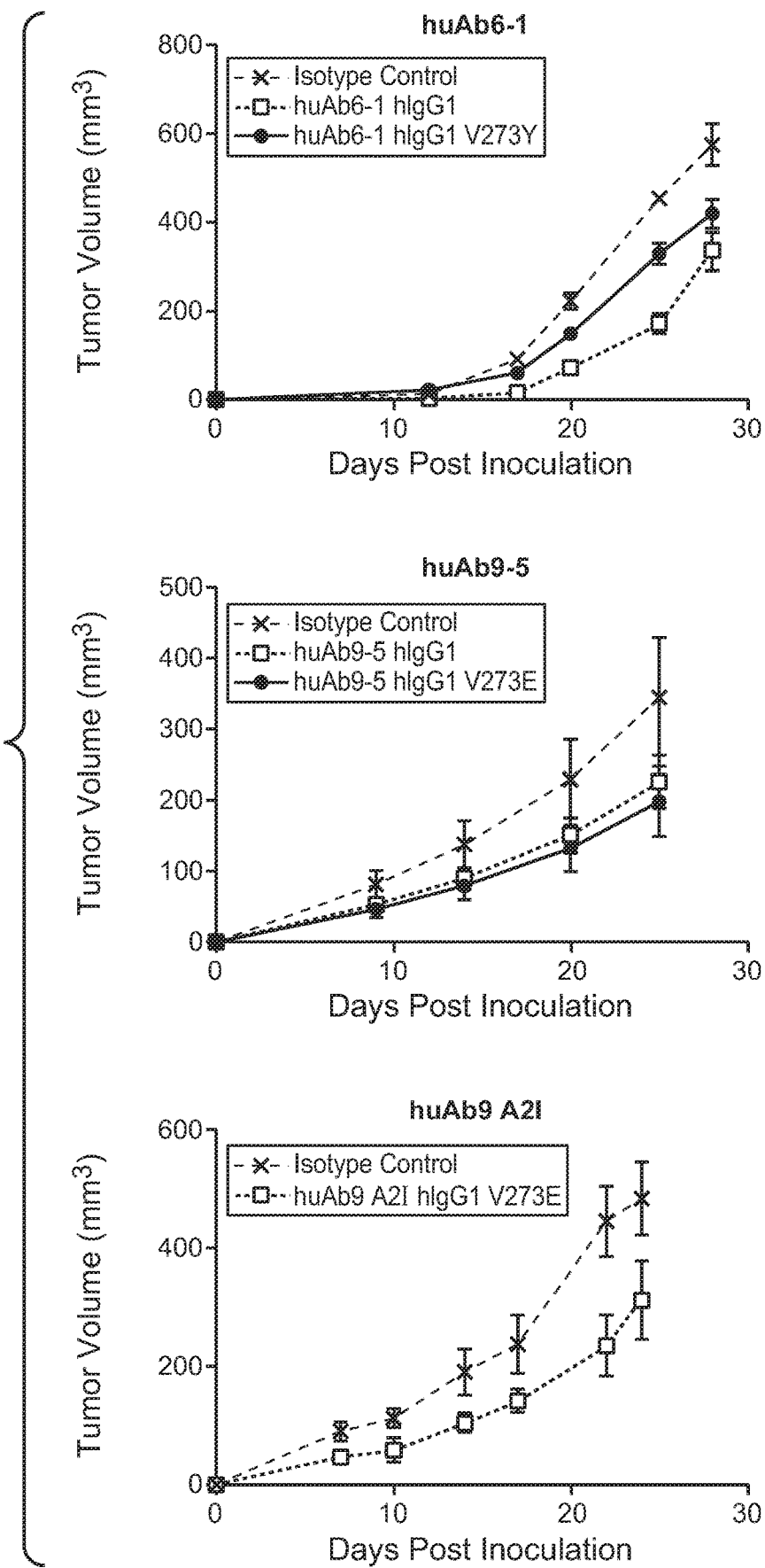
FIG. 11 shows the effect of antibody huAb6-1 (upper), huAb9-5 (middle) or huAb9 A2I (lower) on tumor volume (mm$^3$) in a prophylactic PC3 mouse model.

NSG mice were inoculated subcutaneously with a mixture of PC3 cells (1×10⁶), purified T cells (5×10⁵), and autologous DCs (1×10⁵). A single dose of the anti-CD40 antibodies or control antibodies at 1 mg/kg was injected intraperitoneally immediately after inoculation. Tumor volumes were measured every other day with calipers. Anti-CD40 antibodies including huAb6-1, huAb9-5, huAb9 A2I and their Fc variants V273E or V273Y reduced tumor growth as compared to isotype control antibody in the PC3 model as shown in FIG. 11.

Example 7

Proof-of-Concept Studies In Mouse Syngeneic Tumor Model

Due to the lack of mouse CD40 binding of exemplary anti-CD40 antibodies of the disclosure, evaluation of pharmacologic effects in mouse was performed using a murine CD40 agonist antibody 1C10 muIgG$_1$. In analogy to the huIgG$_1$ Fc V273E mutation discussed above, 1C10 with murine IgG$_1$ (muIgG$_1$) Fc demonstrated strong binding to muFcγRIIB and minimal binding to muFcγRI and muFcγRIV, the functional equivalent to human FcγRIII. Similar to the anti-CD40 antibodies of the disclosure, 1C10 muIgG$_1$ demonstrated potency in stimulating mouse splenic B cell activation in vitro and in vivo. Therefore, anti-murine CD40 antibody 1C10 with murine IgG$_1$ constant region was used as a proof of concept molecule to explore potential clinical development paths, which included using intratumoral delivery or combination therapy with co-administration of an anti-PD-1 antibody.

8.7.1. Intratumoral Administration

A CT26 syngeneic model in which mice harbored bilateral subcutaneous tumors was used to investigate intratumoral administration. Viable cells (1×10⁵) per mouse were inoculated subcutaneously into the right and left hind flanks of female Balb/c mice on Day 0. Animals were randomized into groups on Day 12 with ten mice per group. The mean tumor volume of the right flank at initiation of dosing was about 85 mm³. Three animals from each group were sacrificed 24 hr after the first dose for assessment of serum ALT. The remaining animals were monitored for growth of both tumors. Tumor volume was determined twice weekly. Measurements of the length (L), width (W) and height (H) of the tumor were taken via electronic caliper and the volume was calculated according to the following equation: L×W×H/2. Antibody dosing began immediately following randomization.

Figure 12:
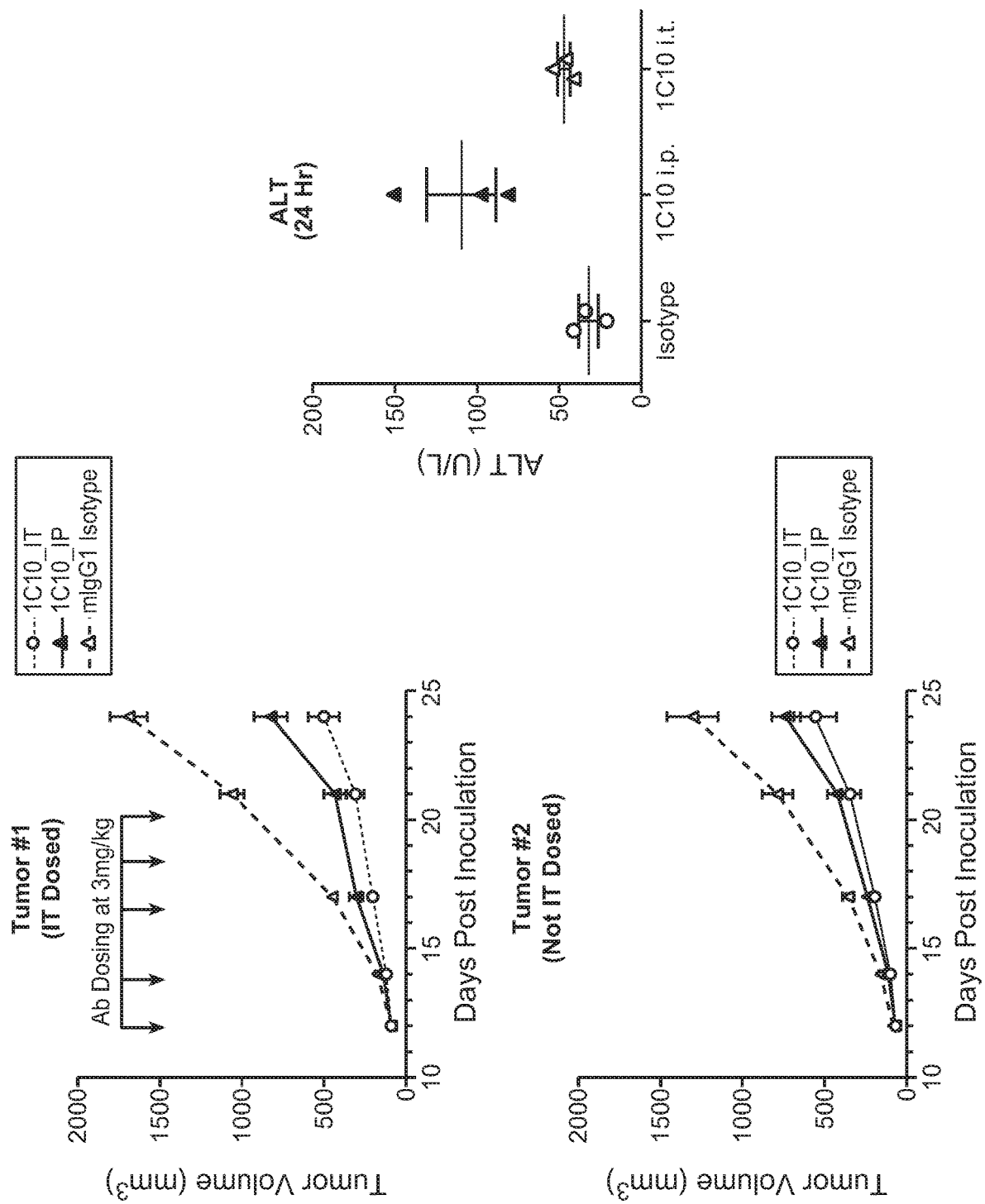
FIG. 12 shows in vivo effects following intratumoral (IT) or intraperitoneal (IP) delivery of anti-CD40 antibody 1C10, or mIgG1 isotype, in a mouse model carrying bilaterally established CT26 syngeneic tumors. IT dosing was administered to one tumor at one flank, with no injection to the tumor at the other flank.

When anti-CD40 antibody 1C10 was directly injected into one tumor (3 mg/kg, 2 to 3 times a week), the growth of tumors at both the injected site ("IT dosed") as well as at a distal site ("Not IT dosed") was reduced, suggesting the establishment of systemic anti-tumor immunity (FIG. 12). Liver toxicity was monitored by liver enzyme ALT measured by VetScan (Abaxis Inc., Union City, Calif.). Intratumoral (IT) dosing of anti-CD40 antibody 1C10 incurred lower ALT elevation than systemic intraperitoneal (IP) dosing.

8.7.2. Combination Therapy with Co-Administration of on Anti-PD-1 Antibody

Figure 13:
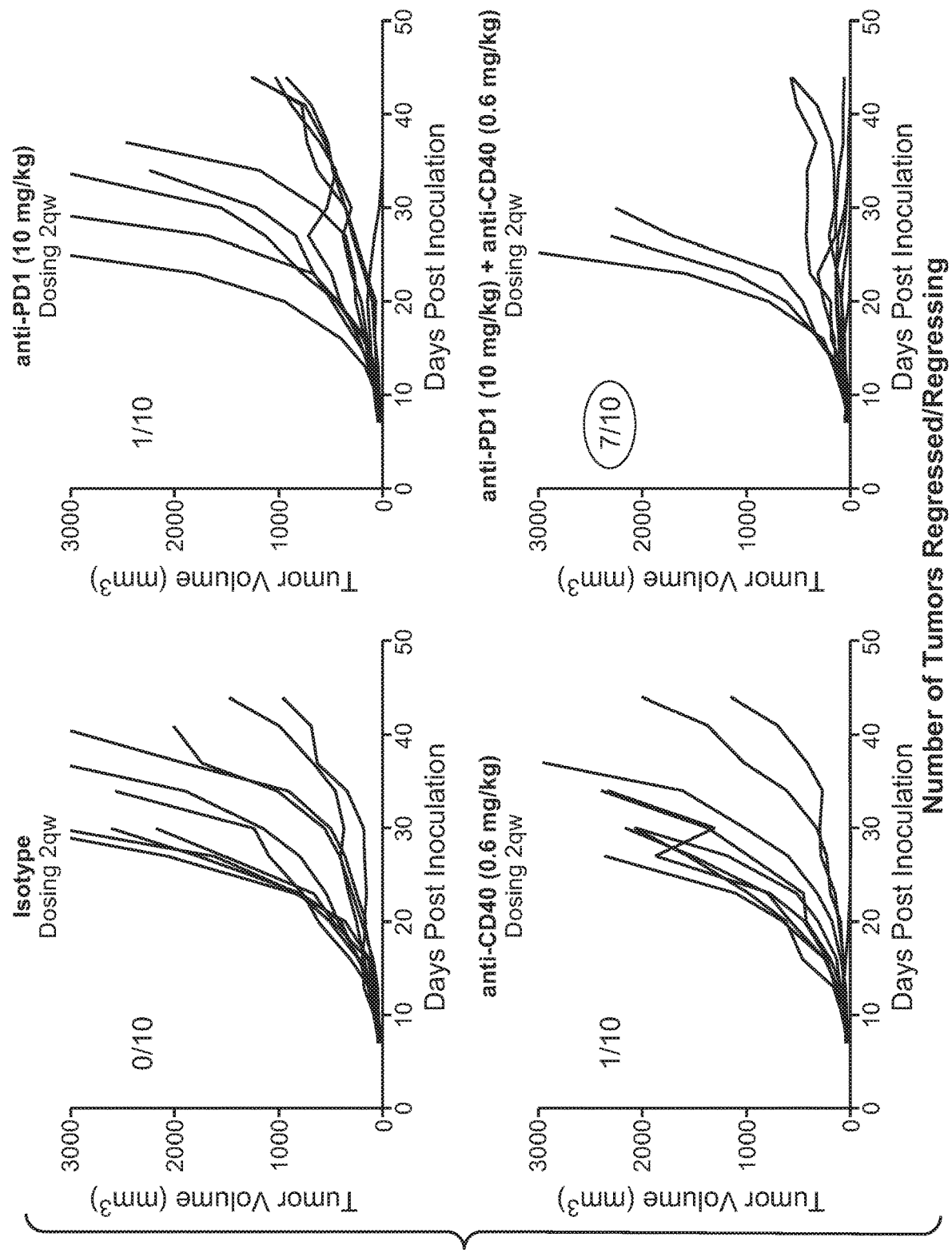
FIG. 13 shows effects on tumor volume (mm$^3$) following dosing two times a week of anti-CD40 antibody 1C10 at 0.6 mg/kg, an anti-PD-1 antibody at 10 mg/kg, or combination treatment of both 1C10 and the anti-PD-1 antibody in a CT26 mouse syngeneic model.

CT26 tumor was established by inoculating 1×10⁵ viable cells per mouse subcutaneously into the right flank of female BALB/c mice on Day 0. Animals were randomized into groups on Day 15. Anti-CD40 antibody 1C10 (0.6 mg/kg) in combination with a proprietary anti-PD1 muIgG$_{2a}$ antibody (10 mg/kg) were dosed IP twice a week in a syngeneic CT26 mouse model. The combined administration regimen exhibited significant anti-tumor activity (7 out of 10 mice showed tumor regression vs. 0 in control and 1 out of 10 in each of anti-PD1 or anti-CD40 treated group), supporting the development of this combination (FIG. 13).

Figure 14:
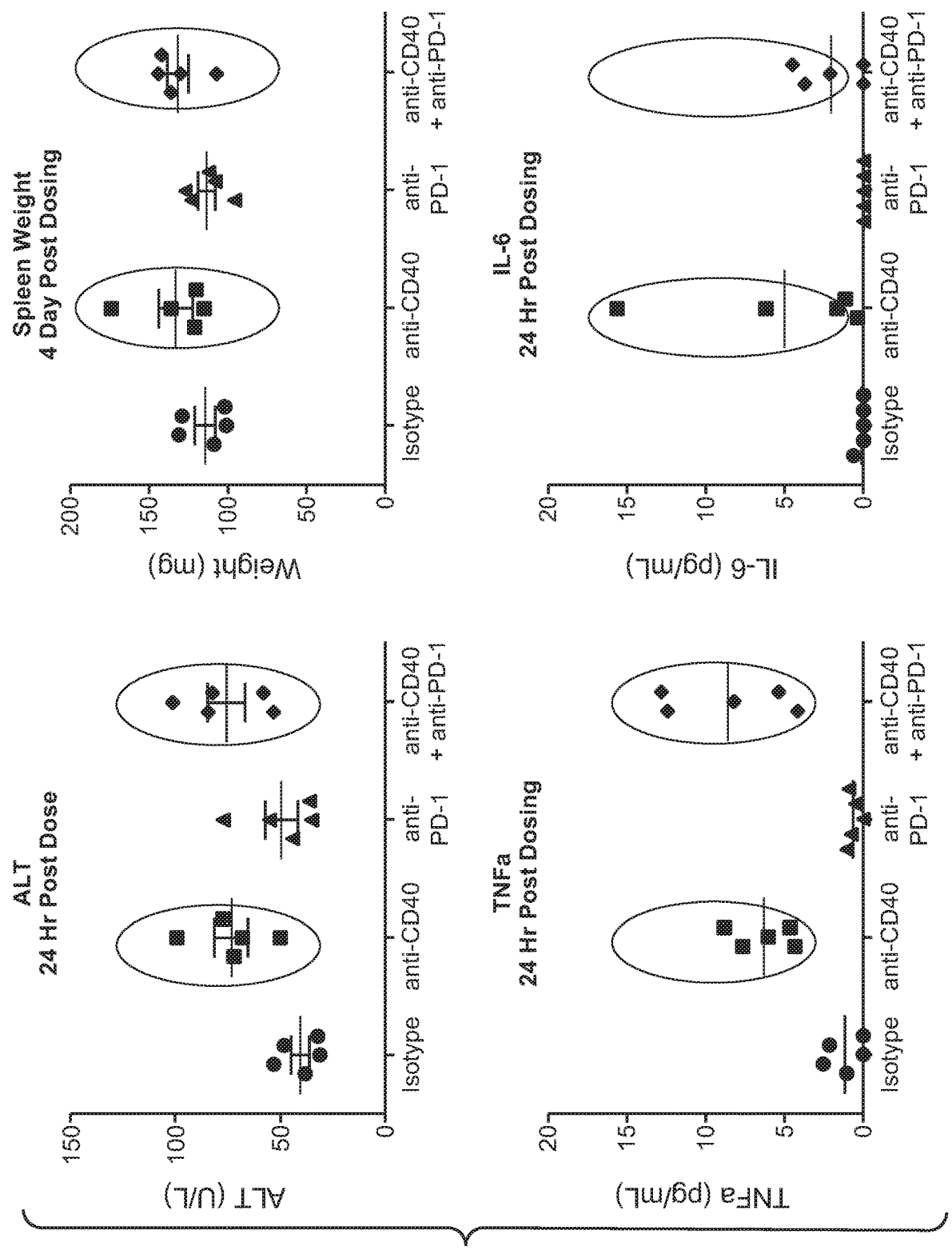
FIG. 14 shows ALT (upper left), TNFα ("TNFa", lower left), or IL-6 (lower right) levels 24 hours after dosing of anti-CD40 antibody 1C10 ("anti-CD40"), anti-PD-1 antibody ("anti-PD-1") or combination treatment ("anti-CD40+ anti-PD-1") in a CT26 mouse syngeneic model. Upper right graph shows spleen weight 4 days post-dosing.

Treatment of anti-CD40 antibody 1C10 was performed at 0.6 mg/kg, which was a sub-therapeutic dose for monotherapy in this model. In some cases, maintaining a level of anti-tumor efficacy at such doses of each monoclonal antibody may afford reduced toxicity, as evidenced, e.g., by liver enzyme levels. In this experiment, the combination treatment did not increase liver enzyme levels, spleen weight, or cytokine levels, such as TNFα or IL-6 (FIG. 14). Liver enzyme levels were measured by VetScan, and cytokine levels were measured with MILLIPLEX Map Mouse Cytokine Kit (EMD Millipore).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An anti-CD40 antibody which comprises (i) a $V_H$ chain comprising three CDRs; and (ii) a $V_L$ chain comprising three CDRs, wherein:

$V_H$ CDR#1 is GYTFTDYYIN; (SEQ ID NO: 7)

$V_H$ CDR#2 is WIFPGSGSVYCNEQFKG; (SEQ ID NO: 17)

$V_H$ CDR#3 is SLGKFAY; (SEQ ID NO: 37)

$V_L$ CDR#1 is KASQSVVTAVA; (SEQ ID NO: 57)

$V_L$ CDR#2 is SASNRYT; (SEQ ID NO: 67) and $V_L$ CDR#3 is QQYSSYPYT. (SEQ ID NO: 87)

2. The anti-CD40 antibody of claim 1 which is or humanized.

3. The anti-CD40 antibody of claim 1 which comprises a $V_H$ chain corresponding to the sequence of SEQ ID NO:113 and a $V_L$ chain corresponding to the sequence of SEQ ID NO: 162.

4. The anti-CD40 antibody of claim 1, which is an $IgG_1$.

5. The anti-CD40 antibody of claim 4, which comprises a variant CH2 region comprising the amino acid substitution V273E or V273Y.

6. The anti-CD40 antibody of claim 4, which comprises a variant Fc region comprising the amino acid substitutions D356E and L358M.

7. The anti-CD40 antibody of claim 4 comprising a kappa light chain constant region.

8. A pharmaceutical composition comprising an anti-CD40 antibody of claim 1, and a pharmaceutically acceptable carrier.

9. The anti-CD40 antibody of claim 1, which is an IgG.

* * * * *

SEQUENCE LISTING

```
<160> NUMBER OF SEQ ID NOS: 200

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Ser Tyr Trp Ile Thr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Gly Tyr Trp Ile Gln
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Thr Phe Thr Asp Tyr Tyr Met Asn
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Asp Tyr Tyr Met Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 5

Gly Tyr Ser Ile Thr Thr Asn Tyr Asn Trp Asn
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Tyr Thr Phe Thr Ser Tyr Trp Met His
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Thr Asp Tyr Tyr Ile Asn
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Tyr Ser Ile Thr Ser Asn Tyr Tyr Trp Asn
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Ser Ile Ser Ser Asn Tyr Tyr Trp Asn
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Tyr Asp Ile Thr Ser Asn Tyr Tyr Trp Asn
1               5                   10

<210> SEQ ID NO 11

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Ile Asn Pro Gly Ser Gly Ser Thr Asn Tyr Asn Glu Lys Phe Lys
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Ile Leu Pro Gly Gly Asp His Thr Lys Tyr Asn Glu Lys Phe Arg
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ile Asn Pro Asn Asn Gly Gly Thr Ser Tyr Asn Gln Lys Phe Lys
1               5                   10                  15

Gly

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Ile Arg Asn Lys Ala Asn Gly Tyr Thr Thr Glu Phe Ser Ala Ser
1               5                   10                  15

Val Lys Gly

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ile Arg His Asp Gly Thr Asn Asn Tyr Asn Pro Ser Leu Lys Asn
1               5                   10                  15

<210> SEQ ID NO 16
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Ile Asp Pro Ser Asn Gly Glu Thr His Tyr Asn Gln Lys Phe Lys
1               5                   10                  15
Asp

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ile Phe Pro Gly Ser Gly Ser Val Tyr Cys Asn Glu Gln Phe Lys
1               5                   10                  15
Gly

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Ile Arg Tyr Asp Gly Ser Asn Asn Tyr Asn Pro Ser Leu Lys Asn
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Ile Asp Pro Ser Asn Gly Glu Thr His Tyr Ala Gln Lys Phe Gln
1               5                   10                  15
Gly

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Ile Phe Pro Gly Ser Gly Ser Val Tyr Ser Asn Glu Gln Phe Lys
1               5                   10                  15
Gly

<210> SEQ ID NO 21
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Tyr Ile Arg Tyr Asp Gly Ser Asn Asn Tyr Asn Pro Ser Leu Lys Ser
 1               5                  10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Ile Arg Tyr Asp Gly Ser Asn Asn Tyr Asn Pro Ser Leu Lys Gly
 1               5                  10                  15

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000
```

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Arg Gly Thr Gly Asp Tyr
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Gly Gly Asp Tyr
1               5

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Gly Gly Leu Gly Arg Gly Thr Tyr Ala Leu Asp Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Gly Gly Leu Arg Gln Gly Trp Tyr Phe Asp Val
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Asp Tyr
1

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 36

Glu Arg Ile Tyr Tyr Ser Gly Ser Thr Tyr Asp Gly Tyr Phe Asp Val
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Leu Gly Lys Phe Ala Tyr
1               5

<210> SEQ ID NO 38

<400> SEQUENCE: 38

000

<210> SEQ ID NO 39

<400> SEQUENCE: 39

000

<210> SEQ ID NO 40
<211> LENGTH: 277
<212> TYPE: PRT
<213> ORGANISM: Homo sapiens

<400> SEQUENCE: 40

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
```

```
            195                 200                 205
Leu Leu Val Leu Val Phe Ile Lys Lys Val Ala Lys Lys Pro Thr Asn
210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Leu Asp Gly Lys Glu Ser Arg Ile Ser
                260                 265                 270

Val Gln Glu Arg Gln
            275

<210> SEQ ID NO 41
<211> LENGTH: 261
<212> TYPE: PRT
<213> ORGANISM: Homo sapiens

<400> SEQUENCE: 41

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 42
```

```
<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Ser Gln Ser Leu Val His Ser Tyr Gly Asn Thr Tyr Leu His
1               5                   10                  15

<210> SEQ ID NO 52
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 52

Arg Ser Ser Gln Ser Leu Val Asn Ser Asn Glu Asn Thr Tyr Leu His
1               5                   10                  15

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ala Ser Gln Asp Ile Ser Asn Tyr Leu Asn
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Asp Ile Arg Asn Tyr Leu Asn
1               5                   10

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ser Ser Gln Ser Leu Glu Asn Ser Tyr Gly Asn Thr Phe Leu Asn
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ala Ser Ser Ser Leu Ser Tyr Met His
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Ala Ser Gln Ser Val Val Thr Ala Val Ala
1               5                   10
```

```
<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ser Ser Gln Ser Leu Glu Asn Thr Asn Gly Asn Thr Phe Leu Asn
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Ser Gln Ser Leu Glu Asn Ser Asn Gly Asn Thr Phe Leu Asn
1               5                   10                  15

<210> SEQ ID NO 60

<400> SEQUENCE: 60

000

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Val Ser Asn Arg Ile Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Val Phe Asn Arg Tyr Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Tyr Thr Ser Arg Leu His Leu
1               5

<210> SEQ ID NO 64
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Thr Ser Arg Leu His Ser
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Val Ser Asn Arg Phe Cys
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Thr Ser Lys Leu Ala Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Ala Ser Asn Arg Tyr Thr
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Val Ser Asn Arg Phe Ser
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69
```

Arg Ile Ser Asn Arg Phe Ser
1               5

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Gln Ser Thr His Val Pro Tyr Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Gln Ser Thr His Val Pro Trp Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Gln Gly Asn Thr Leu Pro Leu Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Gln Gly Lys Thr Leu Pro Trp Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Gln Val Thr His Val Pro Tyr Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 86

Gln Gln Trp Ser Ser Asn Pro Trp Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gln Gln Tyr Ser Ser Tyr Pro Tyr Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Leu Gln Val Thr His Val Pro Phe Thr
1               5

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95
```

```
<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Glu Ile Asn Pro Gly Ser Gly Ser Thr Asn Tyr Asn Glu Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Arg Gly Thr Gly Asp Tyr Trp Gly Gln Gly Thr Thr Leu
            100                 105                 110

Thr Val Ser Ser
        115

<210> SEQ ID NO 102
<211> LENGTH: 114
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 102

Gln Val Gln Leu Gln Gln Ser Gly Ala Glu Leu Met Lys Pro Gly Ala
1               5                   10                  15

Ser Ala Lys Leu Ser Cys Lys Ala Thr Gly Tyr Thr Phe Thr Gly Tyr
            20                  25                  30

Trp Ile Gln Trp Val Lys Gln Arg Pro Gly His Gly Leu Glu Trp Ile
        35                  40                  45

Gly Glu Ile Leu Pro Gly Gly Asp His Thr Lys Tyr Asn Glu Lys Phe
    50                  55                  60

Arg Gly Lys Ala Thr Phe Thr Ser Asp Thr Ser Ser Asn Thr Val Tyr
65                  70                  75                  80

Met Gln Leu Ser Ser Leu Thr Glu Asp Ser Ala Ile Tyr Tyr Cys
                85                  90                  95

Ala Arg Val Gly Gly Asp Tyr Trp Gly Gln Gly Thr Thr Leu Thr Val
            100                 105                 110

Ser Ser

<210> SEQ ID NO 103
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Gly Gly Leu Gly Arg Gly Thr Tyr Ala Leu Asp Tyr Trp
            100                 105                 110

Gly Gln Gly Thr Ser Val Thr Val Ser Ser
        115                 120

<210> SEQ ID NO 104
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Leu Val Gln Pro Gly Gly Ser Leu Ser Leu Ser Cys Ala Ala Ser Gly
1               5                   10                  15

Phe Thr Phe Ser Asp Tyr Tyr Met Ser Trp Val Arg Gln Pro Pro Gly
```

```
                    20                  25                  30

Lys Ala Leu Glu Trp Leu Gly Phe Ile Arg Asn Lys Ala Asn Gly Tyr
                35                  40                  45

Thr Thr Glu Phe Ser Ala Ser Val Lys Gly Arg Phe Thr Ile Ser Arg
            50                  55                  60

Asp Asn Ser Gln Ser Ile Leu Tyr Leu Gln Met Asn Ala Leu Arg Ala
65                  70                  75                  80

Glu Asp Ser Ala Thr Tyr Tyr Cys Ala Arg Tyr Gly Gly Leu Arg Gln
                85                  90                  95

Gly Trp Tyr Phe Asp Val Trp Gly Thr Gly Thr Thr Val Thr Val Ser
                100                 105                 110

Ser
```

<210> SEQ ID NO 105
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Asp Val Gln Leu Gln Glu Ser Gly Pro Gly Leu Val Glu Pro Ser Gln
1               5                   10                  15

Ser Leu Phe Leu Thr Cys Ser Val Thr Gly Tyr Ser Ile Thr Thr Asn
                20                  25                  30

Tyr Asn Trp Asn Trp Ile Arg Gln Phe Pro Gly Asn Lys Leu Glu Trp
                35                  40                  45

Met Gly Tyr Ile Arg His Asp Gly Thr Asn Asn Tyr Asn Pro Ser Leu
            50                  55                  60

Lys Asn Arg Ile Ser Ile Ile Arg Asp Thr Pro Lys Asn Gln Phe Phe
65                  70                  75                  80

Leu Lys Leu Asn Ser Val Thr Thr Glu Asp Thr Ala Ile Tyr Phe Cys
                85                  90                  95

Thr Arg Leu Asp Tyr Trp Gly Gln Gly Thr Ser Val Thr Val Ser Ser
                100                 105                 110
```

<210> SEQ ID NO 106
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Ile Gln Gly Leu Glu Trp Ile
                35                  40                  45

Gly Asn Ile Asp Pro Ser Asn Gly Glu Thr His Tyr Asn Gln Lys Phe
            50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Glu Arg Ile Tyr Tyr Ser Gly Ser Thr Tyr Asp Gly Tyr Phe
                100                 105                 110

Asp Val Trp Gly Thr Gly Thr Thr Val Thr Val Ser Ser
            115                 120                 125

<210> SEQ ID NO 107
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Gln Gln Ser Gly Pro Glu Leu Val Lys Ser Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Val Tyr Cys Asn Glu Gln Phe
    50                  55                  60

Lys Gly Gln Ala Thr Leu Thr Val Asp Arg Ser Ser Ser Thr Ala Tyr
65                  70                  75                  80

Met Leu Leu Ser Ser Leu Thr Ser Glu Asp Ser Ala Val Tyr Phe Cys
                85                  90                  95

Ala Ser Ser Leu Gly Lys Phe Ala Tyr Trp Gly Gln Gly Thr Leu Val
            100                 105                 110

Thr Val Ser Ala
        115

<210> SEQ ID NO 108
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Tyr Trp Asn Trp Ile Arg Gln Phe Pro Gly Asn Lys Leu Glu Trp
        35                  40                  45

Met Gly Tyr Ile Arg Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Leu Asp Tyr Trp Gly Gln Gly Thr Thr Leu Thr Val Ser Ser
            100                 105                 110

<210> SEQ ID NO 109
<211> LENGTH: 112
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 109

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Tyr Trp Asn Trp Ile Arg Gln Phe Pro Gly Asn Lys Leu Glu Trp
        35                  40                  45

Met Gly Tyr Ile Arg Tyr Asp Gly Ser Asn Asn Tyr Asn Pro Ser Leu
50                  55                  60

Lys Asn Arg Ile Ser Ile Thr Arg Asp Thr Ser Lys Asn Gln Phe Phe
65                  70                  75                  80

Leu Arg Leu Asn Ser Val Thr Thr Glu Asp Thr Ala Thr Tyr Tyr Cys
                85                  90                  95

Thr Arg Leu Asp Tyr Trp Gly Gln Gly Thr Thr Leu Thr Val Ser Ser
            100                 105                 110

<210> SEQ ID NO 110
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Asn Ile Asp Pro Ser Asn Gly Glu Thr His Tyr Asn Gln Lys Phe
50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Tyr Tyr Ser Gly Ser Tyr Asp Gly Tyr Phe
            100                 105                 110

Asp Val Trp Gly Gln Gly Thr Thr Val Thr Val Ser Ser
        115                 120                 125

<210> SEQ ID NO 111
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

```
Trp Met His Trp Val Arg Gln Ala Pro Gly Gln Gly Leu Glu Trp Ile
            35                  40                  45

Gly Asn Ile Asp Pro Ser Asn Gly Glu Thr His Tyr Asn Gln Lys Phe
 50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Tyr Tyr Ser Gly Ser Thr Tyr Asp Gly Tyr Phe
            100                 105                 110

Asp Val Trp Gly Gln Gly Thr Thr Val Thr Val Ser Ser
            115                 120                 125
```

<210> SEQ ID NO 112
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Asn Ile Asp Pro Ser Asn Gly Glu Thr His Tyr Ala Gln Lys Phe
 50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Ile Tyr Tyr Ser Gly Ser Thr Tyr Asp Gly Tyr Phe
            100                 105                 110

Asp Val Trp Gly Gln Gly Thr Thr Val Thr Val Ser Ser
            115                 120                 125
```

<210> SEQ ID NO 113
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Ile
            35                  40                  45

Gly Trp Ile Phe Pro Gly Ser Gly Ser Val Tyr Cys Asn Glu Gln Phe
 50                  55                  60

Lys Gly Arg Ala Thr Leu Thr Val Asp Arg Ser Thr Ser Thr Ala Tyr
65                  70                  75                  80
```

```
Met Glu Leu Ser Ser Leu Arg Ser Glu Asp Thr Ala Val Tyr Phe Cys
                85                  90                  95

Ala Ser Ser Leu Gly Lys Phe Ala Tyr Trp Gly Gln Gly Thr Leu Val
            100                 105                 110

Thr Val Ser Ser
        115

<210> SEQ ID NO 114
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Ile
        35                  40                  45

Gly Trp Ile Phe Pro Gly Ser Gly Ser Val Tyr Ser Asn Glu Gln Phe
    50                  55                  60

Lys Gly Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Ser Ser Leu Gly Lys Phe Ala Tyr Trp Gly Gln Gly Thr Leu Val
            100                 105                 110

Thr Val Ser Ser
        115

<210> SEQ ID NO 115
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Gly Leu Glu Trp Ile
        35                  40                  45

Gly Trp Ile Phe Pro Gly Ser Gly Ser Val Tyr Cys Asn Glu Gln Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Leu Gly Lys Phe Ala Tyr Trp Gly Gln Gly Thr Leu Val
            100                 105                 110

Thr Val Ser Ser
        115
```

<210> SEQ ID NO 116
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Asn Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

<210> SEQ ID NO 117
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

<210> SEQ ID NO 118
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Asn

```
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

<210> SEQ ID NO 119
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Glu Ser Gly Gly Gly Leu Val Lys Pro Gly Glu
1               5                   10                  15

Thr Leu Ser Leu Thr Cys Thr Val Ser Gly Tyr Ser Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Gly Arg Val Thr Ile Ser Arg Asp Thr Ser Lys Asn Gln Phe Tyr
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

<210> SEQ ID NO 120
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Gly Arg Val Thr Ile Ser Arg Asp Thr Ser Lys Asn Gln Leu Tyr
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Leu Val Thr Val Ser Ser
```

<210> SEQ ID NO 121
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Glu Val Gln Leu Val Glu Ser Gly Gly Gly Leu Val Lys Pro Gly Glu
1               5                   10                  15

Thr Leu Ile Leu Thr Cys Thr Val Ser Gly Tyr Asp Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Gly Arg Val Thr Ile Ser Arg Asp Thr Ser Lys Asn Gln Phe Tyr
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

<210> SEQ ID NO 122
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Asn Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Leu Val Thr Val Ser Ser
            100                 105                 110

<210> SEQ ID NO 123
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 123

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Tyr Ser Ile Thr Ser Asn
            20                  25                  30

Tyr Tyr Trp Asn Trp Val Arg Gln Ala Pro Gly Lys Gly Leu Glu Trp
            35                  40                  45

Met Gly Tyr Ile Arg Tyr Asp Gly Ser Asn Asn Tyr Asn Pro Ser Leu
 50                  55                  60

Lys Asn Arg Ile Thr Ile Ser Arg Asp Thr Ser Lys Asn Thr Phe Tyr
 65                  70                  75                  80

Leu Gln Met Asn Ser Leu Arg Ala Glu Asp Thr Ala Val Tyr Tyr Cys
            85                  90                  95

Ala Arg Leu Asp Tyr Trp Gly Gln Gly Thr Leu Val Thr Val Ser Ser
            100                 105                 110
```

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Glu Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Ile Thr Ser Asn
            20                  25                  30

Tyr Tyr Trp Asn Trp Ile Arg Gln Pro Pro Gly Lys Gly Leu Glu Trp
```

```
                    35                  40                  45
Met Gly Tyr Ile Arg Tyr Asp Gly Ser Asn Tyr Asn Pro Ser Leu
 50                  55                  60

Lys Asn Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Leu Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 131
```

<211> LENGTH: 441
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn

```
                370                 375                 380
Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly
        435                 440

<210> SEQ ID NO 132
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
                20                  25                  30

Tyr Tyr Trp Asn Trp Ile Arg Gln Pro Pro Gly Lys Gly Leu Glu Trp
            35                  40                  45

Met Gly Tyr Ile Arg Tyr Asp Gly Ser Asn Asn Tyr Asn Pro Ser Leu
        50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Glu Lys Phe Asn Trp
            260                 265                 270

Tyr Val Asp Gly Val Glu Val His Asn Ala Lys Thr Lys Pro Arg Glu
        275                 280                 285
```

```
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Glu Glu
                340                 345                 350
Met Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
                420                 425                 430
Gln Lys Ser Leu Ser Leu Ser Pro Gly Lys
            435                 440

<210> SEQ ID NO 133
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Gln Glu Ser Gly Pro Gly Leu Val Lys Pro Ser Glu
1               5                   10                  15
Thr Leu Ser Leu Thr Cys Thr Val Ser Gly Tyr Ser Ile Thr Ser Asn
            20                  25                  30
Tyr Tyr Trp Asn Trp Ile Arg Gln Pro Pro Gly Lys Gly Leu Glu Trp
        35                  40                  45
Met Gly Tyr Ile Arg Tyr Asp Gly Ser Asn Asn Tyr Asn Pro Ser Leu
    50                  55                  60
Lys Asn Arg Val Thr Ile Ser Arg Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Leu Asp Tyr Trp Gly Gln Gly Thr Thr Val Thr Val Ser Ser
                100                 105                 110
Ala Ser Thr Lys Gly Pro Ser Val Phe Pro Leu Ala Pro Ser Ser Lys
            115                 120                 125
Ser Thr Ser Gly Gly Thr Ala Ala Leu Gly Cys Leu Val Lys Asp Tyr
        130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Gln Thr
            180                 185                 190
Tyr Ile Cys Asn Val Asn His Lys Pro Ser Asn Thr Lys Val Asp Lys
        195                 200                 205
```

Lys Val Glu Pro Lys Ser Cys Asp Lys Thr His Thr Cys Pro Pro Cys
            210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Glu Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 134
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30

Tyr Tyr Trp Asn Trp Ile Arg Gln Pro Pro Gly Lys Gly Leu Glu Trp
        35                  40                  45

Met Gly Tyr Ile Arg Tyr Asp Gly Ser Asn Asn Tyr Asn Pro Ser Leu
    50                  55                  60

Lys Asn Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys

```
            115                 120                 125
Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Tyr Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 135
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asn
            20                  25                  30
```

-continued

```
Tyr Tyr Trp Asn Trp Ile Arg Gln Pro Pro Gly Lys Gly Leu Glu Trp
             35                  40                  45

Met Gly Tyr Ile Arg Tyr Asp Gly Ser Asn Asn Tyr Asn Pro Ser Leu
 50                  55                  60

Lys Asn Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Leu Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Tyr Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
        420                 425                 430

Gln Lys Ser Leu Ser Leu Ser Pro Gly
    435                 440
```

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ala Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Thr
            20                  25                  30

Asn Gly Asn Thr Phe Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

-continued

```
<210> SEQ ID NO 141
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Thr
            20                  25                  30

Asn Gly Asn Thr Phe Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 142
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Thr
            20                  25                  30

Asn Gly Asn Thr Phe Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Val Glu Ala Glu Asp Val Gly Val Tyr Tyr Cys Leu Gln Val
                85                  90                  95

Thr His Val Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu His Trp Tyr Leu Gln Lys Pro Gly Gln Ser
        35                  40                  45

Pro Lys Phe Leu Ile Tyr Lys Val Ser Asn Arg Ile Ser Gly Val Pro
    50                  55                  60

Asp Arg Leu Ser Gly Ser Gly Ser Gly Thr Asp Phe Thr Leu Lys Ile
65                  70                  75                  80

Ser Arg Val Glu Pro Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110

<210> SEQ ID NO 152
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Asn Ser
            20                  25                  30

Asn Glu Asn Thr Tyr Leu His Trp Tyr Leu Gln Lys Pro Gly Gln Ser
        35                  40                  45

Pro Lys Leu Leu Ile Tyr Lys Val Phe Asn Arg Tyr Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Ser
                85                  90                  95

Thr His Val Pro Trp Thr Phe Gly Gly Gly Thr Lys Leu Glu Ile Lys
            100                 105                 110

<210> SEQ ID NO 153
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Pro Leu Ile
            35                  40                  45

Tyr Tyr Thr Ser Arg Leu His Leu Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Ala Gly Thr Lys Leu Glu Leu Lys
            100                 105
```

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Leu Pro Trp
                85                  90                  95

Thr Phe Gly Gly Gly Ser Lys Leu Glu Met Lys
            100                 105
```

<210> SEQ ID NO 155
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Tyr Gly Asn Thr Phe Leu Asn Trp Phe Leu Gln Arg Pro Gly Gln Ser
            35                  40                  45

Pro Gln Leu Leu Ile Tyr Arg Val Ser Asn Arg Phe Cys Gly Val Pro
50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Leu Gly Ile Tyr Phe Cys Leu Gln Val
                85                  90                  95

Thr His Val Pro Tyr Thr Phe Gly Gly Gly Thr Lys Leu Glu Ile Lys
            100                 105                 110

<210> SEQ ID NO 156
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Leu Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105

<210> SEQ ID NO 157
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Leu Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Gly Glu
65                  70                  75                  80

Asp Gly Ala Thr Tyr Tyr Cys Gln Gln Trp Ser Ser Asn Pro Trp Thr
                85                  90                  95

Phe Gly Gly Gly Thr Lys Leu Glu Ile Lys
            100                 105

<210> SEQ ID NO 158
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 158

Asp Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Val Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Ala Leu Thr Ile Arg Thr Met Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 159
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Thr
            20                  25                  30

Asn Gly Asn Thr Phe Leu Asn Trp Phe Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Phe Thr Phe Gly Ser Gly Thr Lys Leu Glu Ile Lys
            100                 105                 110

<210> SEQ ID NO 160
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ala Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Phe Leu Asn Trp Phe Leu Gln Lys Pro Gly Gln Ser
        35                  40                  45

Pro Gln Leu Leu Ile Tyr Arg Ile Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Leu Gln Val
                 85                  90                  95

Thr His Val Pro Phe Thr Phe Gly Ser Gly Thr Lys Leu Glu Ile Lys
            100                 105                 110

<210> SEQ ID NO 161
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Gln Leu Thr Gln Ser Pro Ser Phe Leu Ser Ala Ser Val Gly
 1               5                  10                  15

Asp Arg Val Thr Ile Thr Cys Ser Ala Ser Ser Ser Leu Ser Tyr Met
                20                  25                  30

His Trp Tyr Gln Gln Lys Pro Gly Lys Ser Pro Lys Arg Trp Ile Tyr
            35                  40                  45

Asp Thr Ser Lys Leu Ala Ser Gly Val Pro Ser Arg Phe Ser Gly Ser
 50                  55                  60

Gly Ser Gly Thr Glu Tyr Thr Leu Thr Ile Ser Ser Leu Gln Pro Glu
 65                  70                  75                  80

Asp Phe Ala Thr Tyr Tyr Cys Gln Gln Trp Ser Ser Asn Pro Trp Thr
                 85                  90                  95

Phe Gly Gly Gly Thr Lys Val Glu Ile Lys
            100                 105

<210> SEQ ID NO 162
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Ser Val Val Thr Ala
                20                  25                  30

Val Ala Trp Tyr Gln Gln Lys Pro Gly Lys Ser Pro Lys Leu Leu Ile
            35                  40                  45

Tyr Ser Ala Ser Asn Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Ser Ser Tyr Pro Tyr
                 85                  90                  95

Thr Phe Gly Gly Gly Thr Lys Val Glu Ile Lys
            100                 105

<210> SEQ ID NO 163
<211> LENGTH: 112
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 163

Asp Ala Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Thr
            20                  25                  30

Asn Gly Asn Thr Phe Leu Asn Trp Phe Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Leu Gln Val
                85                  90                  95

Thr His Val Pro Phe Thr Phe Gly Gln Gly Thr Lys Leu Glu Ile Lys
            100                 105                 110

<210> SEQ ID NO 164
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Ala Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Thr
            20                  25                  30

Asn Gly Asn Thr Phe Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Phe Thr Phe Gly Gln Gly Thr Lys Leu Glu Ile Lys
            100                 105                 110

<210> SEQ ID NO 165
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ala Val Met Thr Gln Thr Pro Leu Ser Leu Ser Val Thr Glu Gly
1               5                   10                  15

Gln Pro Ala Ser Ile Ser Cys Arg Ser Ser Gln Ser Leu Glu Asn Thr
            20                  25                  30

Asn Gly Asn Thr Phe Leu Asn Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

```
                 50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Val
                     85                  90                  95

Thr His Val Pro Phe Thr Phe Gly Gln Gly Thr Lys Leu Glu Ile Lys
                100                 105                 110

<210> SEQ ID NO 166
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ala Val Met Thr Gln Thr Pro Leu Ser Leu Ala Val Leu Pro Gly
 1               5                  10                  15

Gln Pro Ala Ser Ile Ser Cys Arg Ser Ser Gln Ser Leu Glu Asn Thr
                20                  25                  30

Asn Gly Asn Thr Phe Leu Asn Trp Tyr Leu Gln Lys Pro Gly Gln Ser
                35                  40                  45

Pro Gln Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Val
                     85                  90                  95

Thr His Val Pro Phe Thr Phe Gly Gln Gly Thr Lys Leu Glu Ile Lys
                100                 105                 110

<210> SEQ ID NO 167
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Leu Glu Asn Thr
                20                  25                  30

Asn Gly Asn Thr Phe Leu Asn Trp Tyr Gln Gln Lys Pro Gly Lys Ala
                35                  40                  45

Pro Lys Leu Leu Ile Tyr Arg Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Leu Gln Val
                     85                  90                  95

Thr His Val Pro Phe Thr Phe Gly Gln Gly Thr Lys Val Glu Ile Lys
                100                 105                 110

<210> SEQ ID NO 168
<211> LENGTH: 112
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 168

Asp Ala Val Met Thr Gln Ser Pro Leu Ser Leu Pro Val Thr Leu Gly
1               5                   10                  15

Glu Pro Ala Ser Ile Ser Cys Arg Ser Ser Gln Ser Leu Glu Asn Thr
            20                  25                  30

Asn Gly Asn Thr Phe Leu Asn Trp Phe Gln Gln Lys Pro Gly Gln Ser
        35                  40                  45

Pro Arg Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Val
                85                  90                  95

Thr His Val Pro Phe Thr Phe Gly Gln Gly Thr Lys Leu Glu Ile Lys
            100                 105                 110

<210> SEQ ID NO 169
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ala Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Glu Asn Thr
            20                  25                  30

Asn Gly Asn Thr Phe Leu Asn Trp Phe Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Leu Gln Val
                85                  90                  95

Thr His Val Pro Phe Thr Phe Gly Gln Gly Thr Lys Leu Glu Ile Lys
            100                 105                 110

<210> SEQ ID NO 170
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Asn Thr
            20                  25                  30

Asn Gly Asn Thr Phe Leu Asn Trp Tyr Leu Gln Lys Pro Gly Gln Ser
        35                  40                  45
```

```
Pro Gln Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Val
                 85                  90                  95

Thr His Val Pro Phe Thr Phe Gly Gln Gly Thr Lys Leu Glu Ile Lys
            100                 105                 110

<210> SEQ ID NO 171
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Val Val Met Thr Gln Thr Pro Leu Ser Leu Ser Val Thr Pro Gly
  1               5                  10                  15

Gln Pro Ala Ser Ile Ser Cys Arg Ser Ser Gln Ser Leu Glu Asn Thr
                 20                  25                  30

Asn Gly Asn Thr Phe Leu Asn Trp Tyr Leu Gln Lys Pro Gly Gln Ser
            35                  40                  45

Pro Gln Leu Leu Ile Tyr Arg Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Val
                 85                  90                  95

Thr His Val Pro Phe Thr Phe Gly Gln Gly Thr Lys Leu Glu Ile Lys
            100                 105                 110

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000
```

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205
```

Cys Asn Val Asp His Lys Pro Ser Asn Thr Lys Val Asp Lys Thr Val
            210                 215                 220
Glu Arg Lys Cys Cys Val Glu Cys Pro Pro Cys Pro Ala Pro Pro Val
225                 230                 235                 240
Ala Gly Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
            260                 265                 270
His Glu Asp Pro Glu Val Gln Phe Asn Trp Tyr Val Asp Gly Val Glu
            275                 280                 285
Val His Asn Ala Lys Thr Lys Pro Arg Glu Glu Gln Phe Asn Ser Thr
            290                 295                 300
Phe Arg Val Val Ser Val Leu Thr Val Val His Gln Asp Trp Leu Asn
305                 310                 315                 320
Gly Lys Glu Tyr Lys Cys Lys Val Ser Asn Lys Gly Leu Pro Ala Pro
            325                 330                 335
Ile Glu Lys Thr Ile Ser Lys Thr Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Met Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly Lys
    450

<210> SEQ ID NO 182
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Tyr Ser Trp
            20                  25                  30
Leu Ala Trp Tyr Gln Gln Lys Pro Gly Lys Ala Pro Asn Leu Leu Ile
        35                  40                  45
Tyr Thr Ala Ser Thr Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ile Phe Pro Leu
            85                  90                  95
Thr Phe Gly Gly Gly Thr Lys Val Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

```
<210> SEQ ID NO 191
<400> SEQUENCE: 191
000

<210> SEQ ID NO 192
<400> SEQUENCE: 192
000

<210> SEQ ID NO 193
<400> SEQUENCE: 193
000

<210> SEQ ID NO 194
<400> SEQUENCE: 194
000

<210> SEQ ID NO 195
<400> SEQUENCE: 195
000

<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
000

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Gly Gly Gly Ser Gly Gly Gly Ser Gly Gly Gly Gly Ser
1               5                   10                  15
```